US010584158B2

(12) United States Patent
Valdes et al.

(10) Patent No.: US 10,584,158 B2
(45) Date of Patent: Mar. 10, 2020

(54) IMMUNOSUPPRESSIVE TGF-β SIGNAL CONVERTER

(71) Applicant: Baylor College of Medicine, Houston, TX (US)

(72) Inventors: Juan Fernando Vera Valdes, Bellaire, TX (US); Cliona M. Rooney, Bellaire, TX (US); Ann Marie Leen, Bellaire, TX (US); Norihiro Watanabe, Houston, TX (US)

(73) Assignee: Baylor College of Medicine, Houston, TX (US)

( * ) Notice: Subject to any disclaimer, the term of this patent is extended or adjusted under 35 U.S.C. 154(b) by 386 days.

(21) Appl. No.: 14/785,248

(22) PCT Filed: Apr. 17, 2014

(86) PCT No.: PCT/US2014/034570
§ 371 (c)(1),
(2) Date: Oct. 16, 2015

(87) PCT Pub. No.: WO2014/172584
PCT Pub. Date: Oct. 23, 2014

(65) Prior Publication Data
US 2016/0075755 A1 Mar. 17, 2016

Related U.S. Application Data

(60) Provisional application No. 61/812,917, filed on Apr. 17, 2013.

(51) Int. Cl.
*C07K 14/705* (2006.01)
*C07K 14/71* (2006.01)
*A61K 38/17* (2006.01)
*A61K 45/06* (2006.01)
*A61N 5/10* (2006.01)

(52) U.S. Cl.
CPC ............ *C07K 14/71* (2013.01); *A61K 38/179* (2013.01); *A61K 38/1774* (2013.01); *A61K 45/06* (2013.01); *A61N 5/10* (2013.01); *C07K 14/70596* (2013.01)

(58) Field of Classification Search
None
See application file for complete search history.

(56) References Cited

FOREIGN PATENT DOCUMENTS

| JP | 2011-515493 A | 5/2011 |
|---|---|---|
| WO | 2009120874 A2 | 10/2009 |
| WO | 20120138858 A1 | 10/2012 |

OTHER PUBLICATIONS

Persson et al (Journal of Biological Chemistry, 1997, 21187-21194.*

Nakazawa et al. "PiggyBac-mediated Cancer Immunotyherapy Using EBV-specific Cytotoxic T-cells Expressing HER2-specific Chimeric Antigen Receptor" Molecular Therapy, Dec. 2011, vol. 19, No. 12, pp. 2133-2143.

Persson et al., "Transforming Growth Factor (TGF-BETA)—Specific Signaling by Chimeric TGF-BETA Type I I Receptor with Intracellular Domain of Activin Type I I B Receptor", Journal of Biological Chemistry, American Society for Biochemistry and Molecular Biology, US, Aug. 22, 1997 (Aug. 22, 1997), vol. 272. No. 34, pp. 21187-21194.

Wieser et al., "Signaling Activity of Transforming Growth Factor SS Type II Receptors Lacking Specific Domains in the Cytoplasmic Region", Molecular and Cellular Biology, American Society for Microbiology, Washington, US, vol. 13, No. 12, Dec. 1, 1993 (Dec. 1, 1993), pp. 7239-7247.

Zhang et al., "Inhibition of TGF-[beta] signaling in genetically engineered tumor antigen-reactive T cells significantly enhances tumor treatment efficacy", Gene Therapy, vol. 20, No. 5. Sep. 13, 2012 (Sep. 13, 2012), pp. 575-580.

Geng et al., "TGF-Beta Suppresses VEGFA-Mediated Angiogenesis in Colon Cancer Metastasis", PLOS ONE, Mar. 25, 2013 (Mar. 25, 2013), vol. 8, No. 3, p. e59918.

Wilkie et al., "Selective Expansion of Chimeric Antigen Receptor-targeted T-cells with Potent Effector Function using Interleukin-4", Journal of Biological Chemistry, Jun. 18, 2010 (Jun. 18, 2010), vol. 285. No. 33, pp. 25538-25544.

Watanabe et al,"Transgenic Expression of a Novel Immunosuppressive Signal Converter on T Cells", Molecular Therapy, May 1, 2013 (May 1, 2013), vol. 21, Supplement 1, pp. S153-S153.

Leen et al., "Reversal of Tumor Immune Inhibition Using a Chimeric Cytokine Receptor", Molecular Therapy, Mar. 20, 2014 (Mar. 20, 2014), vol. 22. No. 6, pp. 1211-1220.

O'Neill, Luke A. J. et al; "The Family of Five: TIR-Domain-Containing Adaptors in Toll-Like Receptor Signalling", Nature Reviews/Immunology; May 2007; vol. 7; 353-364.

Boesen, Christian C., et al: "The 1.1 A Crystal Structure of Human TGF-B Type II Receptor Ligand Binding Domain"; Structure, vol. 10, 913-919, Jul. 2002.

Godfrey III, James I., et al; "Isolated Toll-like Receptor Transmembrane Domains are Capable of Oligomerization"; PLOS ONE; vol. 7, Issue 11, Nov. 2012.

Groppe, Jay, et al; "Cooperative Assembly of TGF-B Superfamily Signaling Complexes is Mediated by Two Disparate Mechanisms and Distinct Modes of Receptor Binding"; Molecular Cell 29, p. 157-168, Feb. 1, 2008.

Hinck, Andrew P., "Structural Studies of the TGF-Bs and their Receptors—Insights into Evolution of the TGF-B Superfamily" EEBS Letters Journal Homepage; FEBS Letter 586 (2012) 1860-1870.

(Continued)

*Primary Examiner* — Michael D Pak
(74) *Attorney, Agent, or Firm* — Norton Rose Fulbright US LLP

(57) ABSTRACT

Embodiments of the disclosure concern cell therapy methods and compositions utilizing cells expressing at least a chimeric TGFβ receptor including the exodomain of a TGFβII receptor and an endodomain that is not from TGFβ receptor, thereby converting the negative signal of TGFβ for T cell proliferation into a T cell activation signal. In at least certain aspects, cells harboring the chimeric TGFβ receptor also harbor one or more chimeric antigen receptors.

3 Claims, 27 Drawing Sheets
Specification includes a Sequence Listing.

(56) References Cited

OTHER PUBLICATIONS

Moresco, Eva Marie Y, et al; Toll-like Receptors; Current Biology vol. 21, No. 13.
Schwarz, Katrin; et al; Role of Toll-Like Receptors in Costimulting Cytotoxic T Cell Responses; Eur. J. Immunol. 2003.33: 1465-1470.
Akira, Shizou, et al; Toll-like Receptors: Critical Proteins Linking Innate and Acquired Immunity; Dept. Of Host Defense, Research Institute for Microbial Diseases; Osaka University; 2001 Nature Publising Group; Aug. 2001, vol. 2, No. 8.
Vinay and Kwon, "Immunotherapy of Cancer with 4-1BB", Molecular Cancer Therapeutics, vol. 11, No. 5, May 1, 2012 (May 1, 2012), pp. 1062-1070.
"Principles of Immunophenotyping" Atlas of Hematopathology; 2013 Elsevier Inc.

\* cited by examiner weekly antigen stimulation and administration of 5 ng/ml of TGFβ1, <u>No</u> IL2 administration

SEQUENCE LISTING

```
<160> NUMBER OF SEQ ID NOS: 6

<210> SEQ ID NO 1
<211> LENGTH: 22
<212> TYPE: PRT
<213> ORGANISM: Homo sapiens

<400> SEQUENCE: 1

Met Gly Arg Gly Leu Leu Arg Gly Leu Trp Pro Leu His Ile Val Leu
1               5                   10                  15

Trp Thr Arg Ile Ala Ser
            20

<210> SEQ ID NO 2
<211> LENGTH: 144
<212> TYPE: PRT
<213> ORGANISM: Homo sapiens

<400> SEQUENCE: 2

Thr Ile Pro Pro His Val Gln Lys Ser Val Asn Asn Asp Met Ile Val
1               5                   10                  15

Thr Asp Asn Asn Gly Ala Val Lys Phe Pro Gln Leu Cys Lys Phe Cys
            20                  25                  30

Asp Val Arg Phe Ser Thr Cys Asp Asn Gln Lys Ser Cys Met Ser Asn
        35                  40                  45

Cys Ser Ile Thr Ser Ile Cys Glu Lys Pro Gln Glu Val Cys Val Ala
    50                  55                  60

Val Trp Arg Lys Asn Asp Glu Asn Ile Thr Leu Glu Thr Val Cys His
65                  70                  75                  80

Asp Pro Lys Leu Pro Tyr His Asp Phe Ile Leu Glu Asp Ala Ala Ser
                85                  90                  95

Pro Lys Cys Ile Met Lys Glu Lys Lys Pro Gly Glu Thr Phe Phe
            100                 105                 110

Met Cys Ser Cys Ser Ser Asp Glu Cys Asn Asp Asn Ile Ile Phe Ser
        115                 120                 125

Glu Glu Tyr Asn Thr Ser Asn Pro Asp Leu Leu Leu Val Ile Phe Gln
    130                 135                 140

<210> SEQ ID NO 3
```

<211> LENGTH: 4704
<212> TYPE: DNA
<213> ORGANISM: Homo sapiens

<400> SEQUENCE: 3

| | | | | | |
|---|---|---|---|---|---|
| ggagagggag | aaggctctcg | ggcggagaga | ggtcctgccc | agctgttggc | gaggagtttc | 60 |
| ctgtttcccc | cgcagcgctg | agttgaagtt | gagtgagtca | ctcgcgcgca | cggagcgacg | 120 |
| acaccccgc | gcgtgcaccc | gctcgggaca | ggagccggac | tcctgtgcag | cttccctcgg | 180 |
| ccgccggggg | cctccccgcg | cctcgccggc | ctccaggccc | cctcctggct | ggcgagcggg | 240 |
| cgccacatct | ggcccgcaca | tctgcgctgc | cggcccggcg | cggggtccgg | agagggcgcg | 300 |
| gcgcggaggc | gcagccaggg | gtccgggaag | gcgccgtccg | ctgcgctggg | ggctcggtct | 360 |
| atgacgagca | gcggggtctg | ccatgggtcg | ggggctgctc | aggggcctgt | ggccgctgca | 420 |
| catcgtcctg | tggacgcgta | tcgccagcac | gatcccaccg | cacgttcaga | agtcggatgt | 480 |
| ggaaatggag | gcccagaaag | atgaaatcat | ctgccccagc | tgtaatagga | ctgcccatcc | 540 |
| actgagacat | attaataacg | acatgatagt | cactgacaac | aacggtgcag | tcaagtttcc | 600 |
| acaactgtgt | aaattttgtg | atgtgagatt | ttccacctgt | gacaaccaga | aatcctgcat | 660 |
| gagcaactgc | agcatcacct | ccatctgtga | aagccacag | gaagtctgtg | tggctgtatg | 720 |
| gagaaagaat | gacgagaaca | taacactaga | gacagtttgc | catgacccca | agctccccta | 780 |
| ccatgacttt | attctggaag | atgctgcttc | tccaaagtgc | attatgaagg | aaaaaaaaaa | 840 |
| gcctggtgag | actttcttca | tgtgttcctg | tagctctgat | gagtgcaatg | acaacatcat | 900 |
| cttctcagaa | gaatataaca | ccagcaatcc | tgacttgttg | ctagtcatat | ttcaagtgac | 960 |
| aggcatcagc | ctcctgccac | cactgggagt | tgccatatct | gtcatcatca | tcttctactg | 1020 |
| ctaccgcgtt | aaccggcagc | agaagctgag | ttcaacctgg | gaaaccggca | agacgcggaa | 1080 |
| gctcatggag | ttcagcgagc | actgtgccat | catcctggaa | gatgaccgct | ctgacatcag | 1140 |
| ctccacgtgt | gccaacaaca | tcaaccacaa | cacagagctg | ctgccattg | agctggacac | 1200 |
| cctggtgggg | aaaggtcgct | tgctgaggt | ctataaggcc | aagctgaagc | agaacacttc | 1260 |
| agagcagttt | gagacagtgg | cagtcaagat | ctttccctat | gaggagtatg | cctcttggaa | 1320 |
| gacagagaag | gacatcttct | cagacatcaa | tctgaagcat | gagaacatac | tccagttcct | 1380 |
| gacggctgag | gagcggaaga | cggagttggg | gaaacaatac | tggctgatca | ccgccttcca | 1440 |
| cgccaagggc | aacctacagg | agtacctgac | gcggcatgtc | atcagctggg | aggacctgcg | 1500 |
| caagctgggc | agctccctcg | cccgggggat | tgctcacctc | cacagtgatc | acactccatg | 1560 |
| tgggaggccc | aagatgccca | tcgtgcacag | ggaccctcaag | agctccaata | tcctcgtgaa | 1620 |
| gaacgaccta | acctgctgcc | tgtgtgactt | tgggcttttcc | ctgcgtctgg | accctactct | 1680 |
| gtctgtggat | gacctggcta | acagtgggca | ggtgggaact | gcaagataca | tggctccaga | 1740 |
| agtcctagaa | tccaggatga | atttggaaa | tgttgagtcc | ttcaagcaga | ccgatgtcta | 1800 |
| ctccatggct | ctggtgctct | gggaaatgac | atctcgctgt | aatgcagtgg | agaagtaaa | 1860 |
| agattatgag | cctccatttg | gttccaaggt | gcgggagcac | cctgtgtcg | aaagcatgaa | 1920 |
| ggacaacgtg | ttgagagatc | gagggcgacc | agaaattccc | agcttctggc | tcaaccacca | 1980 |
| gggcatccag | atggtgtgtg | agacgttgac | tgagtgctgg | gaccacgacc | cagaggcccg | 2040 |
| tctcacagcc | cagtgtgtgg | cagaacgctt | cagtgagctg | gagcatctgg | acaggctctc | 2100 |
| ggggaggagc | tgctcggagg | agaagattcc | tgaagacgc | tccctaaaca | ctaccaaata | 2160 |
| gctcttctgg | ggcaggctgg | gccatgtcca | agaggctgc | ccctctcacc | aaagaacaga | 2220 |

```
ggcagcagga agctgcccct gaactgatgc ttcctggaaa accaaggggg tcactcccct    2280
ccctgtaagc tgtggggata agcagaaaca acagcagcag ggagtgggtg acatagagca    2340
ttctatgcct ttgacattgt cataggataa gctgtgttag cacttcctca ggaaatgaga    2400 ttgatttttta caatagccaa taacatttgc actttattaa tgcctgtata taaatatgaa    2460
tagctatgtt ttatatatat atatatatat ctatatatgt ctatagctct atatatatag    2520
ccataccttg aaaagagaca aggaaaaaca tcaaatattc ccaggaaatt ggttttattg    2580
gagaactcca gaaccaagca gagaaggaag ggacccatga cagcattagc atttgacaat    2640
cacacatgca gtggttctct gactgtaaaa cagtgaactt tgcatgagga aagaggctcc    2700
atgtctcaca gccagctatg accacattgc acttgctttt gcaaaataat cattccctgc    2760
ctagcacttc tcttctggcc atggaactaa gtacagtggc actgtttgag gaccagtgtt    2820 cccgggggttc ctgtgtgccc ttatttctcc tggacttttc atttaagctc caagccccaa    2880
atctgggggg ctagtttaga aactctccct caacctagtt tagaaactct accccatctt    2940
taataccttg aatgttttga accccacttt ttaccttcat gggttgcaga aaaatcagaa    3000
cagatgtccc catccatgcg attgccccac catctactaa tgaaaaattg ttctttttttt    3060 catctttccc ctgcacttat gttactattc tctgctccca gccttcatcc ttttctaaaa    3120
aggagcaaat tctcactcta ggctttatcg tgtttacttt tcattacac ttgacttgat    3180 tttctagttt tctatacaaa caccaatggg ttccatcttt ctgggctcct gattgctcaa    3240
gcacagtttg gcctgatgaa gaggatttca actacacaat actatcattg tcaggactat    3300
gacctcaggc actctaaaca tatgttttgt ttggtcagca cagcgtttca aaaagtgaag    3360
ccactttata aatatttgga gatttttgcag gaaaatctgg atccccaggt aaggatagca    3420 gatggtttttc agttatctcc agtccacgtt cacaaaatgt gaaggtgtgg agacacttac    3480
aaagctgcct cacttctcac tgtaaacatt agctctttcc actgcctacc tggaccccag    3540
tctaggaatt aaatctgcac ctaaccaagg tcccttgtaa gaaatgtcca ttcaagcagt    3600
cattctctgg gtatataata tgattttgac taccttatct ggtgttaaga tttgaagttg    3660
gccttttatt ggactaaagg ggaactcctt taagggtctc agttagccca gtttctttt    3720 gcttatatgt taatagtttt acccctctgca ttggagagag gagtgcttta ctccaagaag    3780
ctttcctcat ggttaccgtt ctctccatca tgccagcctt ctcaaccttt gcagaaatta    3840
ctagagagga tttgaatgtg ggacacaaag gtcccatttg cagttagaaa atttgtgtcc    3900
acaaggacaa gaacaaagta tgagctttaa aactccatag gaaacttgtt aatcaacaaa    3960
gaagtgttaa tgctgcaagt aatctctttt ttaaaacttt ttgaagctac ttattttcag    4020
ccaaatagga atattagaga gggactggta gtgagaatat cagctctgtt tggatggtgg    4080
aaggtctcat tttattgaga ttttttaagat acatgcaaag gtttggaaat agaacctcta    4140
ggcaccctcc tcagtgtggg tgggctgaga gttaaagaca gtgtggctgc agtagcatag    4200
aggcgcctag aaattccact tgcaccgtag ggcatgctga taccatccca atagctgttg    4260
cccattgacc tctagtggtg agtttctaga atactggtcc attcatgaga tattcaagat    4320
tcaagagtat tctcacttct gggttatcag cataaactgg aatgtagtgt cagaggatac    4380
tgtggcttgt tttgtttatg ttttttttttc ttattcaaga aaaagacca aggaataaca    4440 ttctgtagtt cctaaaaata ctgactttt tcactactat acataaaggg aaagttttat    4500
tcttttatgg aacacttcag ctgtactcat gtattaaaat aggaatgtga atgctatata    4560
```

-continued

```
ctctttttat atcaaaagtc tcaagcactt atttttattc tatgcattgt ttgtcttttta    4620 cataaataaa atgtttatta gattgaataa agcaaaatac tcaggtgagc atcctgcctc    4680
ctgttcccat tcctagtagc taaa                                            4704
```

<210> SEQ ID NO 4
<211> LENGTH: 592
<212> TYPE: PRT
<213> ORGANISM: Homo sapiens

<400> SEQUENCE: 4

```
Met Gly Arg Gly Leu Leu Arg Gly Leu Trp Pro Leu His Ile Val Leu
1               5                   10                  15

Trp Thr Arg Ile Ala Ser Thr Ile Pro Pro His Val Gln Lys Ser Asp
            20                  25                  30

Val Glu Met Glu Ala Gln Lys Asp Glu Ile Ile Cys Pro Ser Cys Asn
        35                  40                  45

Arg Thr Ala His Pro Leu Arg His Ile Asn Asn Asp Met Ile Val Thr
    50                  55                  60

Asp Asn Asn Gly Ala Val Lys Phe Pro Gln Leu Cys Lys Phe Cys Asp
65                  70                  75                  80

Val Arg Phe Ser Thr Cys Asp Asn Gln Lys Ser Cys Met Ser Asn Cys
                85                  90                  95

Ser Ile Thr Ser Ile Cys Glu Lys Pro Gln Glu Val Cys Val Ala Val
            100                 105                 110

Trp Arg Lys Asn Asp Glu Asn Ile Thr Leu Glu Thr Val Cys His Asp
        115                 120                 125

Pro Lys Leu Pro Tyr His Asp Phe Ile Leu Glu Asp Ala Ala Ser Pro
    130                 135                 140

Lys Cys Ile Met Lys Glu Lys Lys Lys Pro Gly Glu Thr Phe Phe Met
145                 150                 155                 160

Cys Ser Cys Ser Ser Asp Glu Cys Asn Asp Asn Ile Ile Phe Ser Glu
                165                 170                 175

Glu Tyr Asn Thr Ser Asn Pro Asp Leu Leu Leu Val Ile Phe Gln Val
            180                 185                 190

Thr Gly Ile Ser Leu Leu Pro Pro Leu Gly Val Ala Ile Ser Val Ile
        195                 200                 205

Ile Ile Phe Tyr Cys Tyr Arg Val Asn Arg Gln Gln Lys Leu Ser Ser
    210                 215                 220

Thr Trp Glu Thr Gly Lys Thr Arg Lys Leu Met Glu Phe Ser Glu His
225                 230                 235                 240

Cys Ala Ile Ile Leu Glu Asp Asp Arg Ser Asp Ile Ser Ser Thr Cys
                245                 250                 255

Ala Asn Asn Ile Asn His Asn Thr Glu Leu Leu Pro Ile Glu Leu Asp
            260                 265                 270

Thr Leu Val Gly Lys Gly Arg Phe Ala Glu Val Tyr Lys Ala Lys Leu
        275                 280                 285

Lys Gln Asn Thr Ser Glu Gln Phe Glu Thr Val Ala Val Lys Ile Phe
    290                 295                 300

Pro Tyr Glu Glu Tyr Ala Ser Trp Lys Thr Glu Lys Asp Ile Phe Ser
305                 310                 315                 320

Asp Ile Asn Leu Lys His Glu Asn Ile Leu Gln Phe Leu Thr Ala Glu
                325                 330                 335

Glu Arg Lys Thr Glu Leu Gly Lys Gln Tyr Trp Leu Ile Thr Ala Phe
            340                 345                 350
```

His Ala Lys Gly Asn Leu Gln Glu Tyr Leu Thr Arg His Val Ile Ser
            355                 360                 365

Trp Glu Asp Leu Arg Lys Leu Gly Ser Ser Leu Ala Arg Gly Ile Ala
        370                 375                 380

His Leu His Ser Asp His Thr Pro Cys Gly Arg Pro Lys Met Pro Ile
385                 390                 395                 400

Val His Arg Asp Leu Lys Ser Ser Asn Ile Leu Val Lys Asn Asp Leu
                405                 410                 415

Thr Cys Cys Leu Cys Asp Phe Gly Leu Ser Leu Arg Leu Asp Pro Thr
            420                 425                 430

Leu Ser Val Asp Asp Leu Ala Asn Ser Gly Gln Val Gly Thr Ala Arg
        435                 440                 445

Tyr Met Ala Pro Glu Val Leu Glu Ser Arg Met Asn Leu Glu Asn Val
    450                 455                 460

Glu Ser Phe Lys Gln Thr Asp Val Tyr Ser Met Ala Leu Val Leu Trp
465                 470                 475                 480

Glu Met Thr Ser Arg Cys Asn Ala Val Gly Glu Val Lys Asp Tyr Glu
                485                 490                 495

Pro Pro Phe Gly Ser Lys Val Arg Glu His Pro Cys Val Glu Ser Met
            500                 505                 510

Lys Asp Asn Val Leu Arg Asp Arg Gly Arg Pro Glu Ile Pro Ser Phe
        515                 520                 525

Trp Leu Asn His Gln Gly Ile Gln Met Val Cys Glu Thr Leu Thr Glu
    530                 535                 540

Cys Trp Asp His Asp Pro Glu Ala Arg Leu Thr Ala Gln Cys Val Ala
545                 550                 555                 560

Glu Arg Phe Ser Glu Leu Glu His Leu Asp Arg Leu Ser Gly Arg Ser
                565                 570                 575

Cys Ser Glu Glu Lys Ile Pro Glu Asp Gly Ser Leu Asn Thr Thr Lys
            580                 585                 590

<210> SEQ ID NO 5
<211> LENGTH: 3811
<212> TYPE: DNA
<213> ORGANISM: Homo sapiens

<400> SEQUENCE: 5
acagggccac tgctgctcac agaagcagtg aggatgatgc aggatgatg tctgcctcgc        60 gcctggctgg gactctgatc ccagccatgg ccttcctctc ctgcgtgaga ccagaaagct      120
gggagccctg cgtggagact tggccctaaa ccacacagaa gagctggcat gaaacccaga      180
gctttcagac tccggagcct cagcccttca ccccgattcc attgcttctt gctaaatgct      240
gccgttttat cacggaggtg gttcctaata ttacttatca atgcatggag ctgaatttct      300
acaaaatccc cgacaacctc cccttctcaa ccaagaacct ggacctgagc tttaatcccc      360
tgaggcattt aggcagctat agcttcttca gtttcccaga actgcaggtg ctggatttat      420
ccaggtgtga atccagaca attgaagatg ggcatatca gagcctaagc cacctctcta       480
ccttaatatt gacaggaaac cccatccaga gtttagccct gggagccttt tctggactat      540
caagtttaca gaagctggtg gctgtggaga caaatctagc atctctagag aacttcccca      600
ttggacatct caaaactttg aaagaactta atgtggctca caatcttatc caatctttca      660
aattacctga gtattttctc aatctgacca atctagagca cttggacctt ccagcaaca      720 agattcaaag tatttattgc acagacttgc gggttctaca tcaaatgccc ctactcaatc      780

```
tctctttaga cctgtccctg aaccctatga actttatcca accaggtgca tttaagaaa    840
ttaggcttca taagctgact ttaagaaata attttgatag tttaaatgta atgaaaactt    900
gtattcaagg tctggctggt ttagaagtcc atcgtttggt tctgggagaa tttagaaatg    960
aaggaaactt ggaaaagttt gacaaatctg ctctagaggg cctgtgcaat ttgaccattg   1020
aagaattccg attagcatac ttagactact acctcgatga tattattgac ttatttaatt   1080
gtttgacaaa tgtttcttca ttttccctgg tgagtgtgac tattgaaagg gtaaaagact   1140
tttcttataa tttcggatgg caacatttag aattagttaa ctgtaaattt ggacagtttc   1200
ccacattgaa actcaaatct ctcaaaaggc ttactttcac ttccaacaaa ggtgggaatg   1260
cttttcaga agttgatcta ccaagccttg agtttctaga tctcagtaga aatggcttga   1320
gtttcaaagg ttgctgttct caaagtgatt ttgggacaac cagcctaaag tatttagatc   1380
tgagcttcaa tggtgttatt accatgagtt caaacttctt gggcttagaa caactagaac   1440
atctggattt ccagcattcc aatttgaaac aaatgagtga gttttcagta ttcctatcac   1500
tcagaaacct catttacctt gacatttctc atactcacac cagagttgct ttcaatggca   1560
tcttcaatgg cttgtccagt ctcgaagtct tgaaaatggc tggcaattct ttccaggaaa   1620
acttccttcc agatatcttc acagagctga gaaacttgac cttcctggac ctctctcagt   1680
gtcaactgga gcagttgtct ccaacagcat ttaactcact ctccagtctt caggtactaa   1740
atatgagcca caacaacttc ttttcattgg atacgtttcc ttataagtgt ctgaactccc   1800
tccaggttct tgattacagt ctcaatcaca taatgacttc caaaaaacag gaactacagc   1860
attttccaag tagtctagct ttcttaaatc ttactcagaa tgactttgct tgtacttgtg   1920
aacaccagag tttcctgcaa tggatcaagg accagaggca gctcttggtg aagttgaac    1980
gaatggaatg tgcaacacct tcagataagc agggcatgcc tgtgctgagt ttgaatatca   2040
cctgtcagat gaataagacc atcattggtg tgtcggtcct cagtgtgctt gtagtatctg   2100
ttgtagcagt tctggtctat aagttctatt ttcacctgat gcttcttgct ggctgcataa   2160
agtatggtag aggtgaaaac atctatgatg cctttgttat ctactcaagc caggatgagg   2220
actgggtaag gaatgagcta gtaaagaatt tagaagaagg ggtgcctcca tttcagctct   2280
gccttcacta cagagacttt attcccggtg tggccattgc tgccaacatc atccatgaag   2340
gtttccataa aagccgaaag gtgattgttg tggtgtccca gcacttcatc cagagccgct   2400
ggtgtatctt tgaatatgag attgctcaga cctggcagtt tctgagcagt cgtgctggta   2460
tcatcttcat tgtcctgcag aaggtggaga gacccctgct caggcagcag gtggagctgt   2520
accgccttct cagcaggaac acttacctgg agtgggagga cagtgtcctg gggcggcaca   2580
tcttctggag acgactcaga aaagccctgc tggatggtaa atcatggaat ccagaaggaa   2640
cagtgggtac aggatgcaat tggcaggaag caacatctat ctgaagagga aaaataaaaa   2700
cctcctgagg catttcttgc ccagctgggt ccaacacttg ttcagttaat aagtattaaa   2760
tgctgccaca tgtcaggcct tatgctaagg gtgagtaatt ccatggtgca ctagatatgc   2820
agggctgcta atctcaagga gcttccagtg cagagggaat aaatgctaga ctaaaataca   2880
gagtcttcca ggtgggcatt tcaaccaact cagtcaagga acccatgaca aagaaagtca   2940
tttcaactct tacctcatca agttgaataa agacagagaa aacagaaaga gacattgttc   3000
ttttcctgag tcttttgaat ggaaattgta ttatgttata gccatcataa aaccatttg    3060
gtagttttga ctgaactggg tgttcacttt ttccttttg attgaataca atttaaattc   3120
```

```
tacttgatga ctgcagtcgt caaggggctc ctgatgcaag atgccccttc cattttaagt    3180
ctgtctcctt acagaggtta aagtctaatg gctaattcct aaggaaacct gattaacaca    3240
tgctcacaac catcctggtc attctcgaac atgttctatt ttttaactaa tcacccctga    3300
tatattttta ttttatata tccagttttc attttttac gtcttgccta taagctaata    3360
tcataaataa ggttgtttaa gacgtgcttc aaatatccat attaaccact attttcaag    3420
gaagtatgga aaagtacact ctgtcacttt gtcactcgat gtcattccaa agttattgcc    3480
tactaagtaa tgactgtcat gaaagcagca ttgaaataat ttgtttaaag ggggcactct    3540
tttaaacggg aagaaaattt ccgcttcctg gtcttatcat ggacaatttg ggctataggc    3600
atgaaggaag tgggattacc tcaggaagtc accttttctt gattccagaa acatatgggc    3660
tgataaaccc ggggtgacct catgaaatga gttgcagcag atgtttattt ttttcagaac    3720
aagtgatgtt tgatggacct atgaatctat ttagggagac acagatggct gggatccctc    3780
ccctgtaccc ttctcactga caggagaact a                                  3811
```

<210> SEQ ID NO 6
<211> LENGTH: 799
<212> TYPE: PRT
<213> ORGANISM: Homo sapiens

<400> SEQUENCE: 6

```
Met Glu Leu Asn Phe Tyr Lys Ile Pro Asp Asn Leu Pro Phe Ser Thr
 1               5                   10                  15

Lys Asn Leu Asp Leu Ser Phe Asn Pro Leu Arg His Leu Gly Ser Tyr
                20                  25                  30

Ser Phe Phe Ser Phe Pro Glu Leu Gln Val Leu Asp Leu Ser Arg Cys
            35                  40                  45

Glu Ile Gln Thr Ile Glu Asp Gly Ala Tyr Gln Ser Leu Ser His Leu
        50                  55                  60

Ser Thr Leu Ile Leu Thr Gly Asn Pro Ile Gln Ser Leu Ala Leu Gly
65                  70                  75                  80

Ala Phe Ser Gly Leu Ser Ser Leu Gln Lys Leu Val Ala Val Glu Thr
                85                  90                  95

Asn Leu Ala Ser Leu Glu Asn Phe Pro Ile Gly His Leu Lys Thr Leu
            100                 105                 110

Lys Glu Leu Asn Val Ala His Asn Leu Ile Gln Ser Phe Lys Leu Pro
        115                 120                 125

Glu Tyr Phe Ser Asn Leu Thr Asn Leu Glu His Leu Asp Leu Ser Ser
    130                 135                 140

Asn Lys Ile Gln Ser Ile Tyr Cys Thr Asp Leu Arg Val Leu His Gln
145                 150                 155                 160

Met Pro Leu Leu Asn Leu Ser Leu Asp Leu Ser Leu Asn Pro Met Asn
                165                 170                 175

Phe Ile Gln Pro Gly Ala Phe Lys Glu Ile Arg Leu His Lys Leu Thr
            180                 185                 190

Leu Arg Asn Asn Phe Asp Ser Leu Asn Val Met Lys Thr Cys Ile Gln
        195                 200                 205

Gly Leu Ala Gly Leu Glu Val His Arg Leu Val Leu Gly Glu Phe Arg
    210                 215                 220

Asn Glu Gly Asn Leu Glu Lys Phe Asp Lys Ser Ala Leu Glu Gly Leu
225                 230                 235                 240

Cys Asn Leu Thr Ile Glu Glu Phe Arg Leu Ala Tyr Leu Asp Tyr Tyr
                245                 250                 255
```

-continued

```
Leu Asp Asp Ile Ile Asp Leu Phe Asn Cys Leu Thr Asn Val Ser Ser
            260                 265                 270

Phe Ser Leu Val Ser Val Thr Ile Glu Arg Val Lys Asp Phe Ser Tyr
        275                 280                 285

Asn Phe Gly Trp Gln His Leu Glu Leu Val Asn Cys Lys Phe Gly Gln
        290                 295                 300

Phe Pro Thr Leu Lys Leu Lys Ser Leu Lys Arg Leu Thr Phe Thr Ser
305                 310                 315                 320

Asn Lys Gly Gly Asn Ala Phe Ser Glu Val Asp Leu Pro Ser Leu Glu
                325                 330                 335

Phe Leu Asp Leu Ser Arg Asn Gly Leu Ser Phe Lys Gly Cys Cys Ser
            340                 345                 350

Gln Ser Asp Phe Gly Thr Thr Ser Leu Lys Tyr Leu Asp Leu Ser Phe
        355                 360                 365

Asn Gly Val Ile Thr Met Ser Ser Asn Phe Leu Gly Leu Glu Gln Leu
        370                 375                 380

Glu His Leu Asp Phe Gln His Ser Asn Leu Lys Gln Met Ser Glu Phe
385                 390                 395                 400

Ser Val Phe Leu Ser Leu Arg Asn Leu Ile Tyr Leu Asp Ile Ser His
                405                 410                 415

Thr His Thr Arg Val Ala Phe Asn Gly Ile Phe Asn Gly Leu Ser Ser
            420                 425                 430

Leu Glu Val Leu Lys Met Ala Gly Asn Ser Phe Gln Glu Asn Phe Leu
        435                 440                 445

Pro Asp Ile Phe Thr Glu Leu Arg Asn Leu Thr Phe Leu Asp Leu Ser
        450                 455                 460

Gln Cys Gln Leu Glu Gln Leu Ser Pro Thr Ala Phe Asn Ser Leu Ser
465                 470                 475                 480

Ser Leu Gln Val Leu Asn Met Ser His Asn Asn Phe Phe Ser Leu Asp
                485                 490                 495

Thr Phe Pro Tyr Lys Cys Leu Asn Ser Leu Gln Val Leu Asp Tyr Ser
            500                 505                 510

Leu Asn His Ile Met Thr Ser Lys Lys Gln Glu Leu Gln His Phe Pro
        515                 520                 525

Ser Ser Leu Ala Phe Leu Asn Leu Thr Gln Asn Asp Phe Ala Cys Thr
        530                 535                 540

Cys Glu His Gln Ser Phe Leu Gln Trp Ile Lys Asp Gln Arg Gln Leu
545                 550                 555                 560

Leu Val Glu Val Glu Arg Met Glu Cys Ala Thr Pro Ser Asp Lys Gln
                565                 570                 575

Gly Met Pro Val Leu Ser Leu Asn Ile Thr Cys Gln Met Asn Lys Thr
            580                 585                 590

Ile Ile Gly Val Ser Val Leu Ser Val Leu Val Val Ser Val Val Ala
        595                 600                 605

Val Leu Val Tyr Lys Phe Tyr Phe His Leu Met Leu Leu Ala Gly Cys
        610                 615                 620

Ile Lys Tyr Gly Arg Gly Glu Asn Ile Tyr Asp Ala Phe Val Ile Tyr
625                 630                 635                 640

Ser Ser Gln Asp Glu Asp Trp Val Arg Asn Glu Leu Val Lys Asn Leu
                645                 650                 655

Glu Glu Gly Val Pro Pro Phe Gln Leu Cys Leu His Tyr Arg Asp Phe
            660                 665                 670
```

-continued

```
Ile Pro Gly Val Ala Ile Ala Ala Asn Ile Ile His Glu Gly Phe His
        675                 680                 685
Lys Ser Arg Lys Val Ile Val Val Ser Gln His Phe Ile Gln Ser
    690                 695                 700
Arg Trp Cys Ile Phe Glu Tyr Glu Ile Ala Gln Thr Trp Gln Phe Leu
705                 710                 715                 720
Ser Ser Arg Ala Gly Ile Ile Phe Ile Val Leu Gln Lys Val Glu Lys
                725                 730                 735
Thr Leu Leu Arg Gln Gln Val Glu Leu Tyr Arg Leu Leu Ser Arg Asn
                740                 745                 750
Thr Tyr Leu Glu Trp Glu Asp Ser Val Leu Gly Arg His Ile Phe Trp
        755                 760                 765
Arg Arg Leu Arg Lys Ala Leu Leu Asp Gly Lys Ser Trp Asn Pro Glu
    770                 775                 780
Gly Thr Val Gly Thr Gly Cys Asn Trp Gln Glu Ala Thr Ser Ile
785                 790                 795
```

US 10,584,158 B2

IMMUNOSUPPRESSIVE TGF-β SIGNAL CONVERTER

This application is a national phase application under 35 U.S.C. § 371 that claims priority to International Application No. PCT/US2014/034670 filed Apr. 17, 2014, which claims priority to U.S. Provisional Patent Application Ser. No. 61/812,917, filed Apr. 17, 2013, all of which are incorporated by reference herein in their entirety.

STATEMENT REGARDING FEDERALLY SPONSORED RESEARCH OR DEVELOPMENT

This invention was made with government support under W81XWH-11-1-0625 awarded by the Department of Defense. The government has certain rights in the invention.

TECHNICAL FIELD

Embodiments of the disclosure encompass at least the fields of immunology, cell biology, molecular biology, and medicine, including cancer medicine.

BACKGROUND

Transforming growth factor beta (TGFβ) has been demonstrated to play an important role in the regulation of the immune response, primarily through its suppressive function towards cells of the immune system. TGFβ is a suppressor of antigen-specific T cell proliferation at least through reduction of the cell-cycle rate, as opposed to induction of apoptosis. In particular, TGFβ acts on cytotoxic T lymphocytes (CTLs) to specifically inhibit the expression of at least five cytolytic gene products: perforin, granzyme A, granzyme B, Fas ligand, and interferon gamma that are important for CTL-mediated tumor cytotoxicity (Thomas and Massagué, 2005).

BRIEF SUMMARY

Embodiments of the disclosure include methods and compositions for cancer therapy. In particular embodiments, there are methods and compositions related to cell therapy for cancer. Although particular embodiments may be useful for any cancer, in specific embodiments the methods and compositions are particularly effective against cancers that secrete TGFβ or that reside in a tumor microenvironment (including tumor stroma) that releases TGFβ. Exemplary cancers that are suitable for treatment with the compositions and methods disclosed herein include but are not limited to cancers of the prostate, breast, melanoma, pancreatic, lung, brain, colon, esophageal, liver, kidney, testicular, ovarian, cervical, gall bladder, thyroid, anal, endometrial, bladder, pituitary gland, leukemia, lymphoma, stomach, and spleen.

Aspects of the disclosure utilize cells that are modified to express one or more non-native molecules that render the cells effective against cancers that secrete TGFβ. The cells may be utilized for adoptive cell therapy, in specific embodiments. In particular aspects, the cells are T cells, NK cells, NKT cells, cytotoxic T lymphocytes, antigen-specific T cells, including tumor- or pathogen (such as viral or bacterial)-specific T cells, T cells having αβ T cell receptors (TCR), T cells that comprise at least one chimeric antigen receptor, and so forth. Cells may be genetically engineered to be effective in the presence of TGFβ, and in addition may or may not have other non-naturally occurring genetic modifications. In addition to the chimeric TGFβ receptor, the cells may express other non-native molecules. In particular embodiments, the non-native molecules are cell surface receptors. The molecules may be a chimeric antigen receptor (CAR) specific for a tumor cell surface molecule or αβ TCRs, for example. In certain aspects, a cell may employ one or more chimeric antigen receptors and a chimeric TGFβ receptor.

In embodiments of the disclosure, the cells of the disclosure convert the normally inhibitory signal from TGFβ into an activation stimulus for T cells by utilizing a chimeric TGFβ receptor that employs an extracellular receptor for TGFβ on the cell surface linked to an endodomain from another entity that is capable of an activation signal. In particular embodiments, T cells modified with such chimeric receptors have increased potency compared to cells that lack such chimeric receptors. Specific embodiments of the disclosure employ a chimeric TGFβ receptor expressing the exodomain of TGFβRII linked to an endodomain from another molecule. In specific embodiments the exodomain and the endodomain are linked through a transmembrane domain, and in certain cases the transmembrane domain is the naturally occurring transmembrane domain for the selected endodomain. Although the receptor for TGFβ can be part or all of any one of TGFβ receptor 1, TGFβ receptor 2, or TGFβ receptor 3, in specific embodiments it comprises the TGFβ receptor 2 isoform of the receptor. In specific embodiments, the endodomain comprises the endodomain of the exemplary toll-like receptor (TLR) 4, although others such as TLR1, TLR2, TLR3, TLR4, TLR5, TLR6, TLR7, TLR8, TLR9, CD28, 4-1BB, OX40, CD3zeta, CD40, CD27, or a combination thereof, may be employed, for example. In specific embodiments, the chimeric cytokine receptor is labeled, such as with GFP, mOrange, blue fluorescent protein, and so forth.

In certain aspects of the disclosure, the cell that comprises a chimeric TGFβ receptor also comprises a chimeric antigen receptor. The chimeric antigen receptor (CAR) may be of any kind, but in specific embodiments the CAR targets the cancer that also secretes the TGFβ molecule. Exemplary CARs include at least CARs specific for any one or more of the following: EphA2, HER2, GD2, Glypican-3, 5T4, 8H9, $α_vβ_6$ integrin, B cell maturation antigen (BCMA) B7-H3, B7-H6, CAIX, CA9, CD19, CD20, CD22, kappa light chain, CD30, CD33, CD38, CD44, CD44v6, CD44v7/8, CD70, CD123, CD138, CD171, CEA, CSPG4, EGFR, EGFRvIII, EGP2, EGP40, EPCAM, ERBB3, ERBB4, ErbB3/4, FAP, FAR, FBP, fetal AchR, Folate Receptor α, GD2, GD3, HLA-AI MAGE A1, HLA-A2, IL11Ra, IL13Ra2, KDR, Lambda, Lewis-Y, MCSP, Mesothelin, Muc1, Muc16, NCAM, NKG2D ligands, NY-ESO-1, PRAME, PSCA, PSC1, PSMA, ROR1, Sp17, SURVIVIN, TAG72, TEM1, TEM8, VEGRR2, carcinoembryonic antigen, HMW-MAA, VEGF receptors, and/or other exemplary antigens that are present with in the extracelluar matrix of tumors, such as oncofetal variants of fibronectin, tenascin, or necrotic regions of tumors and other tumor-associated antigens or actionable mutations that are identified through genomic analysis and or differential expression studies of tumors, for example, or a combination thereof. The cells of the disclosure may have more than one CAR, and a CAR may have more than one scFv specific for different antigens.

In certain aspects of the disclosure, the cell that comprises (such as expresses) a chimeric TGFβ receptor also comprises (such as expresses) an antigen-specific receptor. The antigen may be a tumor antigen or a pathogen antigen, including viral or bacterial, for example.

Exemplary tumor antigens include at least the following: carcinoembryonic antigen (CEA) for bowel cancers; CA-125 for ovarian cancer; MUC-1 or epithelial tumor antigen (ETA) or CA15-3 for breast cancer; tyrosinase or melanoma-associated antigen (MAGE) for malignant melanoma; and abnormal products of ras, p53 for a variety of types of tumors; alphafetoprotein for hepatoma, ovarian, or testicular cancer; beta subunit of hCG for men with testicular cancer; prostate specific antigen for prostate cancer; beta 2 microglobulin for multiple myelom and in some lymphomas; CA19-9 for colorectal, bile duct, and pancreatic cancer; chromogranin A for lung and prostate cancer; TA90 for melanoma, soft tissue sarcomas, and breast, colon, and lung cancer. Examples of tumor antigens are known in the art, for example in Cheever et al., 2009, which is incorporated by reference herein in its entirety. Specific examples of tumor antigens include at least CEA, gp100, mesothelin, TRP1, CD40, EGFP, Her2, TCR alpha, trp2, MUC1, cdr2, ras, GITR, WT1, MUC1, LMP2, HPV E6 E7, EGFRvIII, HER-2/neu, MAGE A3, p53 nonmutant, NY-ESO-1, PSMA, GD2, Melan A/MART1, Ras mutant, gp 100, p53 mutant, Proteinase3 (PR1), bcr-abl, Tyrosinase, Survivin, PSA, hTERT, EphA2, PAP, ML-IAP, AFP, EpCAM, ERG (TM-PRSS2 ETS fusion gene), NA17, PAX3, ALK, Androgen receptor, Cyclin B1, Polysialic acid, MYCN, RhoC, TRP-2, GD3, Fucosyl GM1, Mesothelin, PSCA, MAGE A1, sLe(a), CYP1B1, PLAC1, GM3, BORIS, Tn, GloboH, ETV6-AML, NY-BR-1, RGS5, SART3, STn, Carbonic anhydrase IX, PAX5, OY-TES1, Sperm protein 17, LCK, HMWMAA, AKAP-4, SSX2, XAGE 1, B7H3, Legumain, Tie 2, Page4, VEGFR2, MAD-CT-1, FAP, PDGFR-β, MAD-CT-2, and Fos-related antigen 1, for example.

Specific viruses for which an antigen receptor T cell may be directed includes one selected from the group consisting of EBV, CMV, Adenovirus, BK virus, HHV6, RSV, Influenza, Parainfluenza, Bocavirus, Coronavirus, LCMV, Mumps, Measles, Metapneumovirus, Parvovirus B, Rotavirus, West Nile Virus, JC, HHV7, and a combination thereof. In some cases, the virus is EBV and the antigen is selected from the group consisting of EBNA1, LMP2, and BZLF1; the virus may be CMV and the antigen may be selected from the group consisting of IE1 and pp65; the virus may be Adv and the antigen may be selected from the group consisting of Hexon and penton; the virus may be BK virus and the antigen may be selected from the group consisting of LT and VP-1; the virus may be HHV6 and the antigen may be selected from the group consisting of U14, U11, U71, U54, and U90; the virus may be RSV and the antigen may be selected from the group consisting of N and F; the virus may be Influenza and the antigen may be selected from the group consisting of MP1 and NP1.

In embodiments of the disclosure, there is transgenic expression of a novel immunosuppressive signal converter on T cells. The signal converter changes the normally inhibitory action of TGFβ on an immune effector cell into a stimulatory signal for the cell through the use of the chimeric TGFβ receptor that has the TGFβ exodomain linked to an endodomain that is not from TGFβ receptor and provides an activation signal.

In embodiments of the disclosure, there is a polynucleotide comprising a nucleotide sequence encoding a chimeric TGFβ receptor, wherein the receptor comprises an exodomain of TGFβ receptor and a non-TGFβ receptor endodomain. In specific embodiments, the endodomain comprises an endodomain of an immune stimulant protein, or functional fragment thereof, wherein the endodomain or fragment thereof is from toll-like receptor (TLR)1, TLR2, TLR3, TLR4, TLR5, TLR6, TLR7, TLR8, TLR9, CD28, 41BB, 41BB, OX40, CD40, CD27, or a combination thereof. In specific cases, the endodomain is from toll-like receptor (TLR) 4. In particular embodiments, the polynucleotide further comprises a polynucleotide sequence that encodes a chimeric antigen receptor (CAR) or an αβ T cell receptor (TCR). In some embodiments, the expression of the chimeric TGFβ receptor and the expression of the CAR and/or αβ TCR are under control of the same or different regulatory element or elements.

In embodiments wherein one or more polynucleotides are utilized, the polynucleotide may be further defined as an expression construct or vector, and the vector may be a viral vector (such as a retroviral vector, lentiviral vector, adenoviral vector, or adeno-associated viral vector) or a non-viral vector, such as plasmid or RNA, including mRNA.

In certain embodiments, provided herein are one or more cells that comprise a polynucleotide as provided herein. Such cells may be, for example, T cells, natural killer (NK) cells, natural killer T (NKT) cells, antigen-specific T cells, or T cells comprising an αβTCR, or CTLs. In a specific embodiment, the antigen-specific T cells are further defined as tumor-specific T cells or pathogen-specific T cells. In specific cases, the TGFβ receptor comprises part or all of TGFβ receptor II. In some cases, the antigen-specificity of the antigen-specific T cells is natural, whereas in certain cases, the antigen-specificity of the antigen-specific T cells is recombinantly generated. In particular cases, the cell is an antigen-specific T cell, and/or comprises an αβ TCR, which may be native to the T cell or is an engineered molecule. In particular aspects, the antigen-specific T cell is further defined as a tumor-specific T cell or pathogen-specific T cell. In some cases, the antigen-specificity of the antigen-specific T cell is natural, whereas in certain cases, the antigen-specificity of the antigen-specific T cell is recombinantly generated. In some cases, the αβ TCR on the cell is natural, whereas in other cases the αβ TCR on the cell is recombinantly generated; the αβ TCR may be selected for, such as from a library.

In embodiments of the disclosure, there are one or more cells, comprising a first polynucleotide that encodes a chimeric TGFβ receptor, wherein the chimeric TGFβ receptor comprises an exodomain of TGFβ receptor and a non-TGFβ receptor endodomain; and a second polynucleotide that encodes a CAR and/or a αβ TCR. In some cases, the first and second expression construct are the same or different molecule. The antigen-specific T cell may be a tumor-specific T cell receptor or a pathogen-specific T cell receptor. The CAR may be specific for an antigen such as one of the following: PSCA, HER2, CD19, CD20, CD22, Kappa or light chain, CD30, CD33, CD123, CD38, ROR1, ErbB3/4, EGFR, EGFRvIII, EphA2, FAP, carcinoembryonic antigen, EGP2, EGP40, mesothelin, TAG72, PSMA, NKG2D ligands, B7-H6, IL-13 receptor α2, IL-11 receptor R α, MUC1, MUC16, CA9, GD2, GD3, HMW-MAA, CD171, Lewis Y, G250/CAIX, HLA-AI MAGE A1, HLA-A2 NY-ESO-1, PSC1, folate receptor-α, CD44v7/8, 8H9, NCAM, VEGF receptors, 5T4, Fetal AchR, NKG2D ligands, CD44v6, TEM1, TEM8 or a combination thereof.

In some embodiments, provided herein are one or more cells, defined as: 1) being an antigen-specific T cell, and/or a cell comprising a CAR, and/or a cell comprising an αβ T cell receptor; and 2) comprising a chimeric TGFβ receptor, wherein the receptor comprises an exodomain of TGFβ receptor and a non-TGFβ receptor endodomain. In specific embodiments, the cell is autologous with respect to a recipient of said cell. In some cases, the cell is allogenic with respect to a recipient of said cell.

In embodiments of the disclosure, provided herein is a method of treating and/or preventing cancer in an individual, comprising the step of delivering a therapeutically effective amount of a plurality of cells as provided herein to the individual, wherein the individual has a cancer that has cells that secrete TGFβ and/or the cancer has a microenvironment that produces TGFβ. Although in some cases the cancer may be of any kind, in specific cases, the cancer is prostate, breast, melanoma, pancreatic, lung, brain, colon, esophageal, liver, kidney, testicular, ovarian, cervical, gall bladder, thyroid, anal, endometrial, bladder, pituitary gland, leukemia, lymphoma, stomach, spleen, or myeloma. In specific embodiments, the cells are delivered intravenously, intraperitoneally, intratumorally, intrathecally, and/or transrectally. In some embodiments, exposure of TGFβ to the cell protects or enhances the anti-tumor activity of the cell. In particular aspects, the individual is provided with another cancer therapy, such as surgery, chemotherapy, immunotherapy, hormone therapy, radiation, or a combination thereof. In certain embodiments, the cells are allogenic or autologous to said individual. In some aspects, the methods of the disclosure further comprise the step of obtaining peripheral blood mononuclear cells (PBMCs) from the individual or from another individual. In specific embodiments, the method comprises the step of obtaining T cells from the PBMCs and modifying the T cells to comprise a polynucleotide comprising a nucleotide sequence encoding a chimeric TGFβ receptor, wherein the receptor comprises an exodomain of TGFβ receptor and a non-TGFβ receptor endodomain. In embodiments of the disclosure, the cells are provided to the individual more than once. In specific cases, when the cells are provided more than once and the cells comprise a CAR specific for a particular tumor antigen, upon one or more subsequent deliveries the cells comprise a CAR specific for a different tumor antigen.

In an embodiment of the disclosure, there is a method of converting a T cell-inhibitory cytokine signal into a T cell-stimulatory signal, comprising the step of exposing the inhibitory cytokine to a receptor on a T cell, said receptor having an exodomain and an endodomain that is not naturally linked to the exodomain, wherein the exodomain is capable of binding the inhibitory cytokine and the endodomain provides a stimulatory signal to the T cell, wherein the exodomain and the endodomain pair as homodimers. In specific embodiment, the cytokine is TGFβ or VEGF.

In an embodiment of the disclosure, there is a method of converting a T cell-inhibitory cytokine signal into a T cell-stimulatory signal, comprising the step of exposing the inhibitory cytokine to a receptor on a T cell, said receptor having an exodomain and an endodomain that is not naturally linked to the exodomain, wherein the exodomain is capable of binding the inhibitory cytokine and the endodomain provides a stimulatory signal to the T cell, wherein the inhibitory cytokine is not IL4 or IL7 or both. In specific embodiments, the cytokine is TGFβ or VEGF.

Embodiments of the disclosure provide improvements in activity of cells for adoptive transfer therapy in vivo in the presence of cancer cells that secrete the inhibitor TGFβ.

In an embodiment of the disclosure, there is a kit comprising a polynucleotides or polypeptides as described herein and/or a cell or cells as described herein.

The foregoing has outlined the features and technical advantages of the present disclosure in order that the detailed description of the disclosure that follows may be better understood. Additional features and advantages of the disclosure will be described hereinafter which form the subject of the claims of the disclosure. It should be appreciated by those skilled in the art that the conception and specific embodiment disclosed may be readily utilized as a basis for modifying or designing other structures for carrying out the same purposes of the present disclosure. It should also be realized by those skilled in the art that such equivalent constructions do not depart from the spirit and scope of the disclosure as set forth in the appended claims. The novel features which are believed to be characteristic of the disclosure, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present disclosure.

BRIEF DESCRIPTION OF THE DRAWINGS

For a more complete understanding of the present disclosure, reference is now made to the following descriptions taken in conjunction with the accompanying drawing, in which.

DETAILED DESCRIPTION

Figure 1:
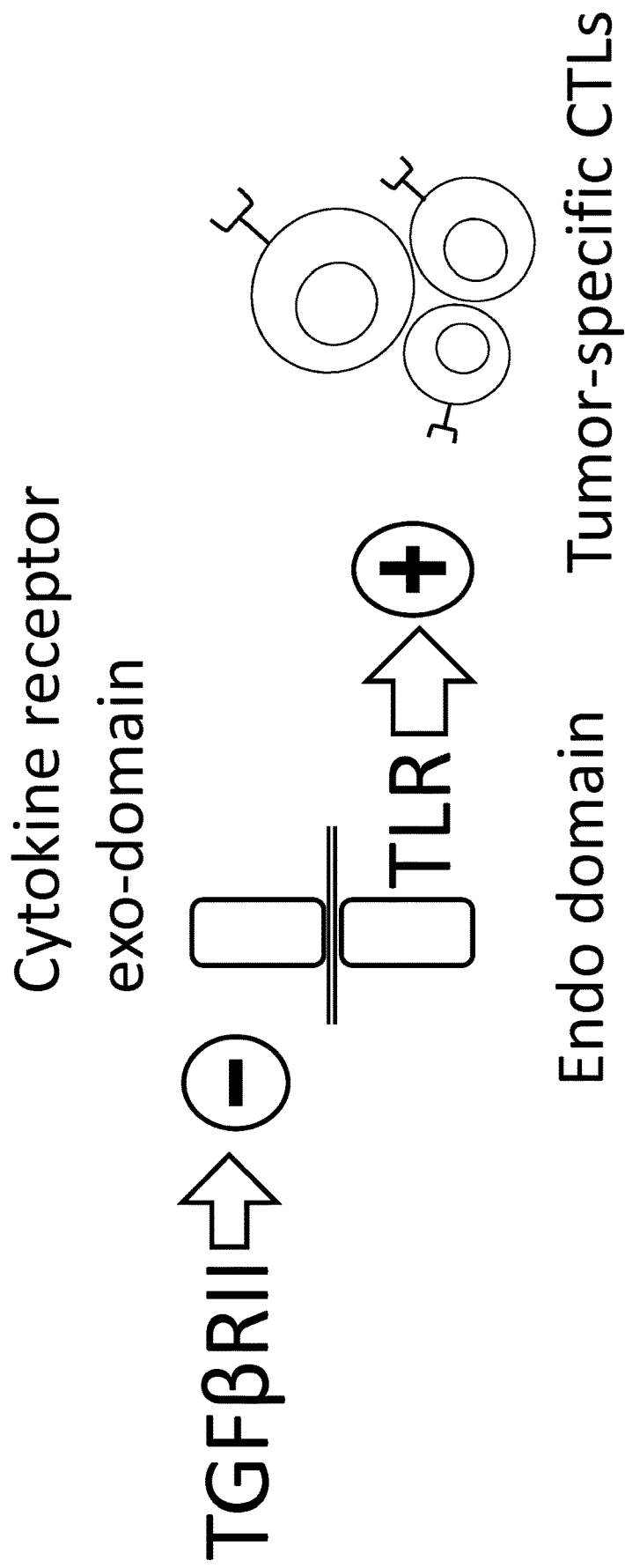
FIG. 1 illustrates an exemplary embodiment of arming T cells to withstand the inhibitory tumor microenvironment.

The words "a" and "an" when used in the present specification in concert with the word comprising, including the claims, denote "one or more." Some embodiments of the disclosure may consist of or consist essentially of one or more elements, method steps, and/or methods of the disclosure. It is contemplated that any method or composition described herein can be implemented with respect to any other method or composition described herein embodiments which are disclosed and still obtain a like or similar result without departing from the spirit and scope of the disclosure.

Embodiments of the present disclosure encompass cells for adoptive cell transfer that have been modified to switch an inhibitory signal that suppresses immune cell proliferation to a stimulatory signal that enhances immune cell proliferation and, at least in some cases, anti-tumor activity. In particular embodiments, immune cells of the disclosure are equipped with receptors that are designed to bind to inhibitory molecules but transmit a positive signal rather than a suppressive one. That is, the cells transform a "brake" signal (such as TGFβ) into an "accelerator" signal to improve the anti-tumor effects of the respective immune cells.

The cells, in certain embodiments, comprise a chimeric cytokine receptor that encompasses a chimera of a TGFβ exodomain (for example) with an endodomain that is from another molecule such that binding of TGFβ to the exodomain causes the endodomain to stimulate activity of the T cell. The cells may or may not have other traits, natural and/or genetically engineered by man, including receptors for other molecules, including at least αβTCR, antigen-specific receptors (including tumor-specific receptors), and/or chimeric antigen receptors, for example.

I. Chimeric Cytokine Receptors

In embodiments of the disclosure, there are compositions that comprise chimeric cytokine receptors that bind to a Th2 or immunosuppressive cytokine (TGFβ is an example) but induce immune stimulatory signaling instead of immunosuppression, resulting in the maintenance of a Th1 (effector) phenotype, proliferation and cytotoxic profile. The receptors as polypeptides and nucleotides that encode them are encompassed in the disclosure.

Embodiments of the disclosure include polypeptides (and the polynucleotides that encode them) that comprise an exodomain of a receptor for an immunosuppressive cytokine fused with an endodomain of an immunostimulatory molecule. In specific embodiments, the exodomain of TGFβR is fused with one or more stimulatory endodomains including for example TLR1, TLR2, TLR3, TLR4, TLR5, TLR6, TLR7, TLR8, TLR9, CD28, 4-1BB, OX40, or combinations of any of the foregoing. Cells harboring such chimeric cytokine receptors protect tumor-reactive immune cells from immunosuppressive cytokines such as TGFβ.

In certain embodiments, provided herein are chimeric TGFβ receptors that include only the exodomain of TGFβ receptor or a TGFβ-binding fragment thereof.

The chimeric TGFβ receptor, in certain embodiments, comprises the exodomain of the TGFβ receptor. Any isoform of the natural TGFβ receptor may be used for its exodomain, including TGFβ receptor 1, TGFβ receptor 2, and TGFβ receptor 3. In particular embodiments, the exodomain for TGFβ receptor 2 is employed in compositions (including expression constructs and cells, for example) of the disclosure. Exemplary nucleotide sequences encoding TGFβ receptor 2 include GenBank® Accession Nos. NM_001024847.2 (SEQ ID NO:3) (polypeptide is NP_001020018; SEQ ID NO:4) or NM_003242.5 (polypeptide is NM_003242). An example of an endodomain is TLR4, and an exemplary sequence for TLR4 is at GenBank® Accession No. U88880 (SEQ ID NO:5) (polypeptide is AAC34135; SEQ ID NO:6).

Polynucleotides for the receptor may include a nucleotide sequence encoding the signal peptide of TGFβ receptor, in specific embodiments. In a certain embodiment, the signal peptide is as follows (amino acid position 1-22 from TGFβ_receptor 2): MGRGLLRGLWPLHIVLWTRIAS (SEQ ID NO:1). In a specific embodiment, the exodomain (which may be referred to as the extracellular domain) includes amino acid position 23-166 from TGFβ receptor 2 as shown in SEQ ID NO:2: TIPPHVQKSVNND-MIVTDNNGAVKFPQLCKFCDVRFSTCDNQKSCM-SNCSITSICEKPQE VCVAVWRKNDENITLETVCHDP-KLPYHDFILEDAASPKCIMKEKKKPGETFFMCSCSSD ECNDNIIFSEEYNTSNPDLLLVIFQ (SEQ ID NO:2). In other specific embodiments, the exodomain is from TGFβ receptor 1, TGFβ receptor 3, or from any other TGFβ receptor or variant thereof.

The disclosure encompasses polynucleotides and polypeptides for the chimeric TGFβ receptors and cells that harbor them. The disclosure includes use of the chimeric TGFβ receptors in methods of treating cancers that secrete TGFβ or that are in a tumor environment that provides TGFβ. The chimeric TGFβ receptors may be used in conjunction on cells that also include one or more CARs.

In particular embodiments, the chimeric TGFβ receptor of the disclosure comprises an endodomain that is not from the endogenous TGFβ receptor. The endodomain may be of any kind so long as it imparts an activation signal to the immune effector cell in which it resides upon binding of TGFβ to the chimeric TGFβ receptor exodomain, e.g., causes T cells that express the chimeric TGFβ receptor to proliferate in the presence of TGFβ. Exemplary endodomains include, for example, an immune stimulant endodomain or fragment thereof from one or more of TLR1, TLR2, TLR3, TLR4, TLR5, TLR6, TLR7, TLR8, TLR9, CD28, 4-1BB, OX40, CD3zeta, CD40, CD27, or a combination thereof.

In embodiments of the disclosure, the chimeric TGFβ receptor may also include a transmembrane domain between the exodomain and endodomain. The transmembrane domain may come from any source, although in specific embodiments it is from the same molecule as the endodomain. In particular embodiments, the chimeric receptor comprises the exodomain of the TGFβ receptor, an endodomain of an immunostimulatory molecule and a transmembrane domain; in particular aspects the transmembrane domain is from the same molecule as the immunostimulatory molecule. In specific embodiments, the chimeric TGFβ receptor comprises a transmembrane domain and one or more additional amino acids (such as one, two, three, four, five, or more additional amino acids (aa)) from the same molecule as the transmembrane domain (TM). An exemplary pattern for the chimeric TGFβ receptor is as follows:

TGFβR exodomain-1, 2, 3, or more aa from TM-TM-non-TGFβR endodomain

In certain embodiments, the exodomain may not include the entire exodomain but instead comprise an epitope and, in some cases, a spacer connected to the endodomain.

II. Host Cells Comprising Chimeric Cytokine Receptors

In embodiments of the disclosure, cells are employed for therapy. The cells encompassed in the disclosure may be immune cells, such as immune effector cells that encompass a T cell, including a cytotoxic T cell (also known as TC, Cytotoxic T Lymphocyte, CTL, T-Killer cell, cytolytic T cell, CD8+ T-cells or killer T cell); NK cells; NKT cells; and other immune cells that can elicit an effector function. In specific embodiments, cells that incorporate the receptors of the disclosure exhibit a bystander effect at the tumor microenvironment at least by depleting inhibitory cytokines from the tumor microenvironment, for example.

As used herein, the terms "cell," "cell line," and "cell culture" may be used interchangeably. All of these terms also include their progeny, which is any and all subsequent generations. It is understood that all progeny may not be identical due to deliberate or inadvertent mutations. In the context of expressing a heterologous nucleic acid sequence, "host cell" refers to a eukaryotic cell that is capable of replicating a vector and/or expressing a heterologous gene encoded by a vector. A host cell can, and has been, used as a recipient for vectors. A host cell may be "transfected" or "transformed," which refers to a process by which exogenous nucleic acid is transferred or introduced into the host cell. A transformed cell includes the primary subject cell and its progeny. As used herein, the terms "engineered" and "recombinant" cells or host cells are intended to refer to a cell into which an exogenous nucleic acid sequence, such as, for example, a vector, has been introduced. Therefore, recombinant cells are distinguishable from naturally occurring cells which do not contain an introduced recombinant nucleic acid.

In certain embodiments, it is contemplated that RNAs or proteinaceous sequences may be co-expressed with other selected RNAs or proteinaceous sequences in the same cell, such as the same CTL. Co-expression may be achieved by co transfecting or co-transducing the CTL with two or more distinct recombinant vectors. Alternatively, a single recombinant vector may be constructed to include multiple distinct coding regions for RNAs, which could then be expressed in CTLs transfected or transduced with the single vector.

Some vectors may employ control sequences that allow it to be replicated and/or expressed in both prokaryotic and eukaryotic cells. One of skill in the art would further understand the conditions under which to incubate all of the above described host cells to maintain them and to permit replication of a vector. Also understood and known are techniques and conditions that would allow large-scale production of vectors, as well as production of the nucleic acids encoded by vectors and their cognate polypeptides, proteins, or peptides.

The cells can be autologous cells, syngeneic cells, allogenic cells and even in some cases, xenogeneic cells, in relation to the individual that receives them.

In many situations one may wish to be able to kill the modified cells, where one wishes to terminate the treatment, the cells become neoplastic, in research where the absence of the cells after their presence is of interest, or other event. For this purpose one can provide for the expression of certain gene products in which one can kill the modified cells under controlled conditions, such as inducible suicide genes.

A. Additional Cellular Characteristics

In addition to the cell comprising a chimeric cytokine receptor, the cell may have one or more other characteristics that are useful for cellular immunotherapy. Such additional characteristics may be inherent to the cell or may be a part of the cell following genetic manipulation by man. There may be more than one characteristic in addition to the chimeric TGFβ receptor. In specific embodiments, in addition to the cell having a chimeric TGFβ receptor, the cell may have a chimeric antigen receptor (CAR), an αβ T cell receptor, and/or an antigen-specific receptor, such as a tumor-specific receptor.

In one embodiment, the host cell is a T-cell comprising one or more chimeric TGFβ receptors and comprising one or more of an engineered αβTCR receptor, a native receptor specific for a tumor antigen, or a CAR; in each case, the additional modification may target a tumor antigen of choice.

Naturally occurring T-cell receptors comprise two subunits, an α-subunit and a β-subunit, each of which is a unique protein produced by recombination event in each T-cell's genome, and libraries of TCRs may be screened for their selectivity to particular target antigens, including tumor antigens. An "engineered TCR" refers to a natural TCR, which has a high-avidity and reactivity toward target antigens that is selected, cloned, and/or subsequently introduced into a population of T-cells used for adoptive immunotherapy. In contrast to engineered TCRs, CARs are engineered to bind target antigens in an MHC-independent manner. In particular embodiments, a CAR comprises an extracellular binding domain including, but not limited to, an antibody or antigen binding fragment thereof; a transmembrane domain; one or more intracellular costimulatory signaling domains and a primary signaling domain.

In embodiments wherein T cell receptors are generated in cells that express or will express a chimeric cytokine receptor, in specific embodiments the methods use exposure of peripheral mononuclear blood cells with libraries of mixture of peptide from a tumor antigen (see PCT/US2013/025342, which is incorporated by reference herein in its entirety).

In certain embodiments of the disclosure, there are immune effector cells that include the chimeric TGFβ receptor and also that are modified to comprise at least one CAR that allows bypass of tumor immune escape mechanisms that are due to abnormalities in protein-antigen processing and presentation.

In particular cases, the cells include a CAR that is chimeric, non-natural and engineered at least in part by the hand of man. In particular cases, the engineered CAR has one, two, three, four, or more components, and in some embodiments the one or more components facilitate targeting or binding of the cell (such as a T lymphocyte) to the tumor antigen-comprising cancer cell. In specific embodiments, the CAR comprises a part of an antibody for the tumor antigen, part or all of a cytoplasmic signaling domain, and/or part or all of one or more co-stimulatory molecules, for example endodomains of co-stimulatory molecules. In specific embodiments, the antibody is a single-chain variable fragment (scFv). In certain aspects the antibody is directed at target antigens on the cell surface of cancer cells that secrete TGFβ, for example. In certain embodiments, a cytoplasmic signaling domain, such as those derived from the T cell receptor zeta-chain, is employed as at least part of the chimeric receptor in order to produce stimulatory signals for T lymphocyte proliferation and effector function following engagement of the chimeric receptor with the target antigen. Examples include, but are not limited to, endodomains from co-stimulatory molecules such as CD27, CD28, 4-1BB, and OX40. In particular embodiments, co-stimulatory molecules are employed to enhance the activation, proliferation, and cytotoxicity of T cells produced by the CAR after antigen engagement. In specific embodiments, the co-stimulatory molecules are CD28, OX40, and 4-1BB.

The CAR may be first generation, second generation, or third generation (CAR in which signaling is provided by CD3ξ together with co-stimulation provided by CD28 and a tumor necrosis factor receptor (TNFr), such as 4-1BB or OX40), for example. The CAR may be specific for PSCA, HER2, CD19, CD20, CD22, Kappa or light chain, CD30, CD33, CD123, CD38, ROR1, ErbB2, ErbB3/4, EGFR, EGFRvIII, EphA2, FAP, carcinoembryonic antigen, EGP2, EGP40, mesothelin, TAG72, PSMA, NKG2D ligands, B7-H6, IL-13 receptor α2, IL-11 receptor α, MUC1, MUC16, CA9, GD2, GD3, HMW-MAA, CD171, Lewis Y, G250/CAIX, HLA-AI MAGE A1, HLA-A2 NY-ESO-1, PSC1, folate receptor-α, CD44v7/8, 8H9, NCAM, VEGF receptors, 5T4, Fetal AchR, NKG2D ligands, CD44v6, TEM1, TEM8, viral-associated antigens expressed by the tumor, or other tumor-associated antigens that are identified through genomic analysis and or differential expression studies of tumors. A single cell may have multiple CARs, including CARs that target different tumor antigens.

In particular embodiments the CAR is encoded on an expression vector that may or may not also encode the chimeric TGFβ receptor. The vector may be bicistronic, in particular embodiments. When present on the same expression construct, the CAR coding sequence may be configured 5' or 3' to the chimeric TGFβ receptor coding sequence. The expression of the CAR and the chimeric TGFβ receptor may be under the direction of the same or different regulatory sequences.

B. Introduction of Constructs into Host Cells

Expression vectors that encode the chimeric cytokine receptor and optionally comprise at least one CAR, αβTCR, and/or antigen-specific receptor can be introduced as one or more DNA molecules or constructs, where there may be at least one marker that will allow for selection of host cells that contain the construct(s). The constructs can be prepared in conventional ways, where the genes and regulatory regions may be isolated, as appropriate, ligated, cloned in an appropriate cloning host, analyzed by restriction or sequencing, or other convenient means. Particularly, using PCR, individual fragments including all or portions of a functional unit may be isolated, where one or more mutations may be introduced using "primer repair", ligation, in vitro mutagenesis, etc., as appropriate. The construct(s) once completed and demonstrated to have the appropriate sequences may then be introduced into the CTL by any convenient means. The construct(s) may be integrated and packaged into non-replicating, defective viral genomes like Adenovirus, Adeno-associated virus (AAV), or Herpes simplex virus (HSV) or others, including retroviral vectors, for infection or transduction into cells. The constructs may include viral sequences for transfection, if desired. Alternatively, the construct may be introduced by fusion, electroporation, biolistics, transfection, lipofection, or the like. The host cells may be grown and expanded in culture before introduction of the construct(s), followed by the appropriate treatment for introduction of the construct(s) and integration of the construct(s). The cells are then expanded and screened by virtue of a marker present in the construct. Various markers that may be used successfully include hprt, neomycin resistance, thymidine kinase, hygromycin resistance, etc.

In some instances, one may have a target site for homologous recombination, where it is desired that a construct be integrated at a particular locus. For example,) can knock-out an endogenous gene and replace it (at the same locus or elsewhere) with the gene encoded for by the construct using materials and methods as are known in the art for homologous recombination. For homologous recombination, one may use either .OMEGA. or O-vectors. See, for example, Thomas and Capecchi, Cell (1987) 51, 503-512; Mansour, et al., Nature (1988) 336, 348-352; and Joyner, et al., Nature (1989) 338, 153-156.

The constructs may be introduced as a single DNA molecule encoding at least the chimeric TGFβ receptor and optional CAR(s), or different DNA molecules having one or more genes. The constructs may be introduced simultaneously or consecutively, each with the same or different markers.

Vectors containing useful elements such as bacterial or yeast origins of replication, selectable and/or amplifiable markers, promoter/enhancer elements for expression in pro-karyotes or eukaryotes, etc. that may be used to prepare stocks of construct DNAs and for carrying out transfections are well known in the art, and many are commercially available.

III. Polynucleotides Encoding Chimeric Cytokine Receptors

The present disclosure also encompasses a composition comprising a nucleic acid sequence encoding a chimeric cytokine receptor as defined above and cells harboring the nucleic acid sequence. The nucleic acid molecule is a recombinant nucleic acid molecule, in particular aspects, and it may be synthetic. It may comprise DNA, RNA as well as PNA (peptide nucleic acid) and it may be a hybrid thereof.

It is evident to the person skilled in the art that one or more regulatory sequences may be added to the nucleic acid molecule comprised in the composition of the disclosure. For example, promoters, transcriptional enhancers and/or sequences that allow for induced expression of the polynucleotide of the disclosure may be employed. A suitable inducible system is for example tetracycline-regulated gene expression as described, e.g., by Gossen and Bujard (Proc. Natl. Acad. Sci. USA 89 (1992), 5547-5551) and Gossen et al. (Trends Biotech. 12 (1994), 58-62), or a dexamethasone-inducible gene expression system as described, e.g. by Crook (1989) EMBO J. 8, 513-519.

In certain embodiments, the chimeric TGFβ receptor is expressed constitutively by the cell or vector. In other embodiments, expression of the chimeric TGFβ receptor is under the control of an inducible promoter, e.g., a promoter that is inducible by TGFβ or by another molecule present in the tumor microenvironment.

Furthermore, it is envisaged for further purposes that nucleic acid molecules may contain, for example, thioester bonds and/or nucleotide analogues. The modifications may be useful for the stabilization of the nucleic acid molecule against endo- and/or exonucleases in the cell. The nucleic acid molecules may be transcribed by an appropriate vector comprising a chimeric gene that allows for the transcription of said nucleic acid molecule in the cell. In this respect, it is also to be understood that such polynucleotides can be used for "gene targeting" or "gene therapeutic" approaches. In another embodiment the nucleic acid molecules are labeled. Methods for the detection of nucleic acids are well known in the art, e.g., Southern and Northern blotting, PCR or primer extension. This embodiment may be useful for screening methods for verifying successful introduction of the nucleic acid molecules described above during gene therapy approaches.

The nucleic acid molecule(s) may be a recombinantly produced chimeric nucleic acid molecule comprising any of the aforementioned nucleic acid molecules either alone or in combination. In specific aspects, the nucleic acid molecule is part of a vector.

The present disclosure therefore also relates to a composition comprising a vector comprising the nucleic acid molecule described in the present disclosure.

Many suitable vectors are known to those skilled in molecular biology, the choice of which would depend on the function desired and include plasmids, cosmids, viruses, bacteriophages and other vectors used conventionally in genetic engineering. Methods that are well known to those skilled in the art can be used to construct various plasmids and vectors; see, for example, the techniques described in Sambrook et al. (1989) and Ausubel, Current Protocols in Molecular Biology, Green Publishing Associates and Wiley Interscience, N.Y. (1989), (1994). Alternatively, the polynucleotides and vectors of the disclosure can be reconstituted into liposomes for delivery to target cells. A cloning vector may be used to isolate individual sequences of DNA. Relevant sequences can be transferred into expression vectors where expression of a particular polypeptide is required. Typical cloning vectors include pBluescript SK, pGEM, pUC9, pBR322 and pGBT9. Typical expression vectors include pTRE, pCAL-n-EK, pESP-1, pOP13CAT.

In specific embodiments, there is a vector that comprises a nucleic acid sequence that is a regulatory sequence operably linked to the nucleic acid sequence encoding a chimeric cytokine receptor construct defined herein. Such regulatory sequences (control elements) are known to the artisan and may include a promoter, a splice cassette, translation initiation codon, translation and insertion site for introducing an insert into the vector. In specific embodiments, the nucleic acid molecule is operatively linked to said expression control sequences allowing expression in eukaryotic or prokaryotic cells.

It is envisaged that a vector is an expression vector comprising the nucleic acid molecule encoding a chimeric cytokine receptor construct defined herein. In specific aspects, the vector is a viral vector, such as a lentiviral vector. Lentiviral vectors are commercially available, including from Clontech (Mountain View, Calif.) or GeneCopoeia (Rockville, Md.), for example.

The term "regulatory sequence" refers to DNA sequences that are necessary to effect the expression of coding sequences to which they are ligated. The nature of such control sequences differs depending upon the host organism. In prokaryotes, control sequences generally include promoters, ribosomal binding sites, and terminators. In eukaryotes generally control sequences include promoters, terminators and, in some instances, enhancers, transactivators or transcription factors. The term "control sequence" is intended to include, at a minimum, all components the presence of which are necessary for expression, and may also include additional advantageous components.

The term "operably linked" refers to a juxtaposition wherein the components so described are in a relationship permitting them to function in their intended manner. A control sequence "operably linked" to a coding sequence is ligated in such a way that expression of the coding sequence is achieved under conditions compatible with the control sequences. In case the control sequence is a promoter, it is obvious for a skilled person that double-stranded nucleic acid is preferably used.

Thus, the recited vector is an expression vector, in certain embodiments. An "expression vector" is a construct that can be used to transform a selected host and provides for expression of a coding sequence in the selected host. Expression vectors can for instance be cloning vectors, binary vectors or integrating vectors. Expression comprises transcription of the nucleic acid molecule preferably into a translatable mRNA. Regulatory elements ensuring expression in prokaryotes and/or eukaryotic cells are well known to those skilled in the art. In the case of eukaryotic cells they comprise normally promoters ensuring initiation of transcription and optionally poly-A signals ensuring termination of transcription and stabilization of the transcript. Possible regulatory elements permitting expression in prokaryotic host cells comprise, e.g., the $P_L$, lac, trp or tac promoter in E. coli, and examples of regulatory elements permitting expression in eukaryotic host cells are the AOX1 or GAL1 promoter in yeast or the CMV-, SV40-, RSV-promoter (Rous sarcoma virus), CMV-enhancer, SV40-enhancer or a globin intron in mammalian and other animal cells.

Beside elements that are responsible for the initiation of transcription such regulatory elements may also comprise transcription termination signals, such as the SV40-poly-A site or the tk-poly-A site, downstream of the polynucleotide. Furthermore, depending on the expression system used leader sequences capable of directing the polypeptide to a cellular compartment or secreting it into the medium may be added to the coding sequence of the recited nucleic acid sequence and are well known in the art. The leader sequence(s) is (are) assembled in appropriate phase with translation, initiation and termination sequences, and preferably, a leader sequence capable of directing secretion of translated protein, or a portion thereof, into the periplasmic space or extracellular medium. Optionally, the heterologous sequence can encode a fusion protein including an N-terminal identification peptide imparting desired characteristics, e.g., stabilization or simplified purification of expressed recombinant product; see supra. In this context, suitable expression vectors are known in the art such as Okayama-Berg cDNA expression vector pcDV1 (Pharmacia), pEF-Neo, pCDM8, pRc/CMV, pcDNA1, pcDNA3 (Invitrogen), pEF-DHFR and pEF-ADA, (Raum et al. Cancer Immunol Immunother (2001) 50(3), 141-150) or pSPORT1 (GIBCO BRL).

In some embodiments, the expression control sequences are eukaryotic promoter systems in vectors capable of transforming of transfecting eukaryotic host cells, but control sequences for prokaryotic hosts may also be used. Once the vector has been incorporated into the appropriate host, the host is maintained under conditions suitable for high level expression of the nucleotide sequences, and as desired, the collection and purification of the polypeptide of the disclosure may follow.

Additional regulatory elements may include transcriptional as well as translational enhancers. Advantageously, the above-described vectors of the disclosure comprises a selectable and/or scorable marker. Selectable marker genes useful for the selection of transformed cells are well known to those skilled in the art and comprise, for example, antimetabolite resistance as the basis of selection for dhfr, which confers resistance to methotrexate (Reiss, Plant Physiol. (Life-Sci. Adv.) 13 (1994), 143-149); npt, which confers resistance to the aminoglycosides neomycin, kanamycin and paromycin (Herrera-Estrella, EMBO J. 2 (1983), 987-995) and hygro, which confers resistance to hygromycin (Marsh, Gene 32 (1984), 481-485). Additional selectable genes have been described, namely trpB, which allows cells to utilize indole in place of tryptophan; hisD, which allows cells to utilize histinol in place of histidine (Hartman, Proc. Natl. Acad. Sci. USA 85 (1988), 8047); mannose-6-phosphate isomerase which allows cells to utilize mannose (WO 94/20627) and ODC (ornithine decarboxylase) which confers resistance to the ornithine decarboxylase inhibitor, 2-(difluoromethyl)-DL-ornithine, DEMO (McConlogue, 1987, In: Current Communications in Molecular Biology, Cold Spring Harbor Laboratory ed.) or deaminase from *Aspergillus teneus* which confers resistance to Blasticidin S (Tamura, Biosci. Biotechnol. Biochem. 59 (1995), 2336-2338).

Useful scorable markers are also known to those skilled in the art and are commercially available. Advantageously, said marker is a gene encoding luciferase (Giacomin, Pl. Sci. 116 (1996), 59-72; Scikantha, J. Bact. 178 (1996), 121), green fluorescent protein (Gerdes, FEBS Lett. 389 (1996), 44-47) or β-glucuronidase (Jefferson, EMBO J. 6 (1987), 3901-3907). This embodiment is particularly useful for simple and rapid screening of cells, tissues and organisms containing a recited vector.

As described above, the recited nucleic acid molecule can be used in a cell, alone, or as part of a vector to express the encoded polypeptide in cells. The nucleic acid molecules or vectors containing the DNA sequence(s) encoding any one of the above described chimeric cytokine receptor constructs is introduced into the cells that in turn produce the polypeptide of interest. The recited nucleic acid molecules and vectors may be designed for direct introduction or for introduction via liposomes, or viral vectors (e.g., adenoviral, retroviral) into a cell. In certain embodiments, the cells are T-cells, CAR T-cells, NK cells, NKT-cells, MS Cs, neuronal stem cells, or hematopoietic stem cells, for example.

In accordance with the above, the present disclosure relates to methods to derive vectors, particularly plasmids, cosmids, viruses and bacteriophages used conventionally in genetic engineering that comprise a nucleic acid molecule encoding the polypeptide sequence of a chimeric cytokine receptor construct defined herein. In particular embodiments, the vector is an expression vector and/or a gene transfer or targeting vector. Expression vectors derived from viruses such as retroviruses, vaccinia virus, adeno-associated virus, herpes viruses, or bovine papilloma virus, may be used for delivery of the recited polynucleotides or vector into targeted cell populations. Methods which are well known to those skilled in the art can be used to construct recombinant vectors; see, for example, the techniques described in Sambrook et al. (loc cit.), Ausubel (1989, loc cit.) or other standard text books. Alternatively, the recited nucleic acid molecules and vectors can be reconstituted into liposomes for delivery to target cells. The vectors containing the nucleic acid molecules of the disclosure can be transferred into the host cell by well-known methods, which vary depending on the type of cellular host. For example, calcium chloride transfection is commonly utilized for prokaryotic cells, whereas calcium phosphate treatment or electroporation may be used for other cellular hosts; see Sambrook, supra.

IV. Pharmaceutical Compositions

In accordance with this disclosure, the term "pharmaceutical composition" relates to a composition for administration to an individual and encompasses compositions of cells for immunotherapy. In specific embodiments, the cells for immunotherapy are engineered to express at least a chimeric cytokine receptor. In certain embodiments, the cells comprise one or more additional modifications, such as one or more receptors, including receptors for tumor antigens.

In a particular embodiment, the pharmaceutical composition comprises a composition for parenteral, transdermal, intraluminal, intra-arterial, intrathecal or intravenous administration or for direct injection into a cancer. It is in particular envisaged that said pharmaceutical composition is administered to the individual via infusion or injection. Administration of the suitable compositions may be effected by different ways, e.g., by intravenous, subcutaneous, intraperitoneal, intramuscular, topical or intradermal administration.

The pharmaceutical composition of the present disclosure may further comprise a pharmaceutically acceptable carrier. Examples of suitable pharmaceutical carriers are well known in the art and include phosphate buffered saline solutions, water, emulsions, such as oil/water emulsions, various types of wetting agents, sterile solutions, etc. Compositions comprising such carriers can be formulated by well-known conventional methods. These pharmaceutical compositions can be administered to the subject at a suitable dose.

The dosage regimen will be determined by the attending physician and clinical factors. As is well known in the medical arts, dosages for any one patient depends upon many factors, including the patient's size, body surface area, age, the particular compound to be administered, sex, time and route of administration, general health, and other drugs being administered concurrently. A particular dosage for administration might be in the range of between $5 \times 10^6$ per m2 and $3 \times 10^8$ per m2.

The compositions of the disclosure may be administered locally or systemically. The compositions provided herein, e.g., cells expressing the constructs provided herein, may, in certain embodiments, be administered parenterally, e.g., intravenous, intraarterial, intrathecal, subdermal or intramuscular administration. In certain other embodiments, DNA encoding the constructs provided herein may be administered directly to the target site, e.g., by biolistic delivery to an internal or external target site or by catheter to a site in an artery. In a preferred embodiment, the pharmaceutical composition is administered subcutaneously and in an even more preferred embodiment intravenously. Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishes, electrolyte replenishers (such as those based on Ringer's dextrose), and the like. Preservatives and other additives may also be present such as, for example, antimicrobials, anti-oxidants, chelating agents, and inert gases and the like. In addition, the pharmaceutical composition of the present disclosure might comprise proteinaceous carriers, like, e.g., serum albumin or immunoglobulin, preferably of human origin. It is envisaged that the pharmaceutical composition of the disclosure might comprise, in addition to the proteinaceous chimeric cytokine receptor constructs or nucleic acid molecules or vectors encoding the same (as described in this disclosure), further biologically active agents, depending on the intended use of the pharmaceutical composition. In specific embodiments, the cells are infused intravenously in 10% DMSO, 40% saline and 50% human serum albumin.

V. Therapeutic Uses of Chimeric Cytokine Receptors and Host T-Cells Comprising Chimeric Cytokine Receptors In various embodiments chimeric cytokine receptor constructs, nucleic acid sequences, vectors, and/or host cells, as contemplated herein and/or pharmaceutical compositions comprising the same are used for the prevention, treatment or amelioration of a cancerous disease, such as a tumorous disease. In particular embodiments, the pharmaceutical composition of the present disclosure may be particularly useful in preventing, ameliorating and/or treating cancer, including solid tumors, for example. In certain cases, the cancer has a tumor antigen.

As used herein "treatment" or "treating," includes any beneficial or desirable effect on the symptoms or pathology of a disease or pathological condition, and may include even minimal reductions in one or more measurable markers of the disease or condition being treated, e.g., cancer. Treatment can involve optionally either the reduction or amelioration of symptoms of the disease or condition, or the delaying of the progression of the disease or condition. "Treatment" does not necessarily indicate complete eradication or cure of the disease or condition, or associated symptoms thereof.

As used herein, "prevent," and similar words such as "prevented," "preventing" etc., indicate an approach for preventing, inhibiting, or reducing the likelihood of the occurrence or recurrence of, a disease or condition, e.g., cancer. It also refers to delaying the onset or recurrence of a disease or condition or delaying the occurrence or recurrence of the symptoms of a disease or condition. As used herein, "prevention" and similar words also includes reducing the intensity, effect, symptoms and/or burden of a disease or condition prior to onset or recurrence of the disease or condition.

In particular embodiments, the present invention contemplates, in part, cells, chimeric cytokine receptor construct, nucleic acid molecules and vectors that can administered either alone or in any combination using standard vectors and/or gene delivery systems, and in at least some aspects, together with a pharmaceutically acceptable carrier or excipient. In certain embodiments, subsequent to administration, said nucleic acid molecules or vectors may be stably integrated into the genome of the subject.

In specific embodiments, viral vectors may be used that are specific for certain cells or tissues and persist in said cells. Suitable pharmaceutical carriers and excipients are well known in the art. The compositions prepared according to the disclosure can be used for the prevention or treatment or delaying the above identified diseases.

Furthermore, the disclosure relates to a method for the prevention, treatment or amelioration of a tumorous disease comprising the step of administering to a subject in need thereof an effective amount of cells harboring the chimeric cytokine receptor molecule, a nucleic acid sequence, a vector, as contemplated herein and/or produced by a process as contemplated herein.

Possible indications for administration of the composition (s) of the exemplary chimeric cytokine receptor-comprising cells are cancerous diseases, including tumorous diseases, including breast, prostate, lung, and colon cancers or epithelial cancers/carcinomas such as breast cancer, colon cancer, prostate cancer, head and neck cancer, skin cancer, cancers of the genito-urinary tract, e.g. ovarian cancer, endometrial cancer, cervix cancer and kidney cancer, lung cancer, gastric cancer, cancer of the small intestine, liver cancer, pancreas cancer, gall bladder cancer, cancers of the bile duct, esophagus cancer, cancer of the salivary glands and cancer of the thyroid gland. The administration of the composition(s) of the disclosure is useful for all stages and types of cancer, including for minimal residual disease, early cancer, advanced cancer, and/or metastatic cancer and/or refractory cancer, for example.

The disclosure further encompasses co-administration protocols with other compounds, e.g. bispecific antibody constructs, targeted toxins or other compounds, which act via immune cells. The clinical regimen for co-administration of the inventive compound(s) may encompass co-administration at the same time, before or after the administration of the other component. Particular combination therapies include the use of a chemotherapeutic agent (e.g., a chemotherapeutic agent listed in Section VII.A. below), radiation, surgery, hormone therapy, or other types of immunotherapy, in combination with the chimeric TGFβ receptor-expressing cells provided herein.

Embodiments relate to a kit comprising a chimeric cytokine receptor construct as defined above, a nucleic acid sequence as defined above, a vector as defined above and/or a host as defined above. It is also contemplated that the kit of this disclosure comprises a pharmaceutical composition as described herein above, either alone or in combination with further medicaments to be administered to an individual in need of medical treatment or intervention.

By way of illustration, cancer patients or patients susceptible to cancer or suspected of having cancer may be treated as follows. Cells modified as described herein may be administered to the individual and retained for extended periods of time. The individual may receive one or more administrations of the cells, and the timing of separations of administrations may be on the order of days, weeks, months, or years. In specific embodiments, multiple administrations occur within weeks or months of each other, such as 1, 2, 3, 4, 5, 6, 7, 8, 9, 10, 11, 12, or more weeks or months. In some embodiments, the genetically modified cells are encapsulated to inhibit immune recognition and placed at the site of the tumor. In cases where cells are provided to the individual following tumor recurrence after initially treating with cells of the disclosure, the cells may be altered such that they recognize a different target tumor antigen. For example, when initial rounds include cells that harbor the chimeric cytokine receptor and another receptor specific for a particular antigen, upon subsequent rounds (including upon tumor recurrence, if it occurs) may utilize a receptor for a different particular antigen.

In particular cases the individual is provided with effective amounts of the therapeutic cells that encompass a chimeric TGFβ receptor and, optionally, 2) a CAR, αβ TCR, and/or antigen-specific receptor. The cells may be delivered at the same time or at different times from one or more other cancer therapies. The cells and the other cancer therapy may be delivered in the same or separate formulations. The cells and the other cancer therapy may be provided to the individual in separate delivery routes. The cells and/or the other cancer therapy may be delivered by injection at a tumor site or intravenously or orally, for example. Routine delivery routes for such compositions are known in the art.

The cells that have been modified with the construct(s) are then grown in culture under selective conditions and cells that are selected as having the construct may then be expanded and further analyzed, using, for example; the polymerase chain reaction for determining the presence of the construct in the host cells. Once the modified host cells have been identified, they may then be used as planned, e.g., expanded in culture or introduced into a host organism.

Depending upon the nature of the cells, the cells may be introduced into a host organism, e.g., a mammal, in a wide variety of ways. The cells may be introduced at the site of the tumor, in specific embodiments, although in alternative embodiments the cells hone to the cancer or are modified to hone to the cancer. The number of cells that are employed will depend upon a number of circumstances, the purpose for the introduction, the lifetime of the cells, the protocol to be used, for example, the number of administrations, the ability of the cells to multiply, the stability of the recombinant construct, and the like. The cells may be applied as a dispersion, generally being injected at or near the site of interest. The cells may be in a physiologically-acceptable medium.

The DNA introduction need not result in integration in every case. In some situations, transient maintenance of the DNA introduced may be sufficient. In this way, one could have a short term effect, where cells could be introduced into the host and then turned on after a predetermined time, for example, after the cells have been able to home to a particular site.

The cells may be administered as desired. In certain embodiments, the regimen parameters may be modulated using various protocols. In specific embodiments, the route or number or timing of administration, the life of the cells, and/or the number of cells present, may be varied. The number of administrations may depend upon the factors described above, for example, at least in part.

It should be appreciated that the system is subject to many variables, such as the cellular response to the ligand, the efficiency of expression and, as appropriate, the level of secretion, the activity of the expression product, the particular need of the individual, which may vary with time and circumstances, the rate of loss of the cellular activity as a result of loss of cells or expression activity of individual cells, and the like. Therefore, it is expected that for each individual patient, even if there were universal cells that could be administered to the population at large, each patient would be monitored for the proper dosage for the individual, and such practices of monitoring a patient are routine in the art.

In specific embodiments, there is a screening assay employed as part of, or not as part of, methods of the disclosure. For example, in certain embodiments, a biopsy is taken and the level of TGFβ production is assessed so as to determine whether the construct would work in the individual from which the biopsy is taken. In specific embodiments, the assay method identified cancers that detectably express TGFβ or a certain level of TGFβ.

VI. Kits of the Invention

Any of the compositions described herein may be comprised in a kit. In a non-limiting example, chimeric cytokine receptor-expressing cells for use in cell therapy and/or the reagents to generate one or more cells for use in cell therapy that harbors recombinant expression vectors may be comprised in a kit. The kit components are provided in suitable container means.

Some components of the kits may be packaged either in aqueous media or in lyophilized form. The container means of the kits will generally include at least one vial, test tube, flask, bottle, syringe or other container means, into which a component may be placed, and preferably, suitably aliquoted. Where there are more than one component in the kit, the kit also will generally contain a second, third or other additional container into which the additional components may be separately placed. However, various combinations of components may be comprised in a vial. The kits of the present disclosure also will typically include a means for containing the components in close confinement for commercial sale. Such containers may include injection or blow molded plastic containers into which the desired vials are retained.

When the components of the kit are provided in one and/or more liquid solutions, the liquid solution is an aqueous solution, with a sterile aqueous solution being particularly useful. In some cases, the container means may itself be a syringe, pipette, and/or other such like apparatus, from which the formulation may be applied to an infected area of the body, injected into an animal, and/or even applied to and/or mixed with the other components of the kit.

However, the components of the kit may be provided as dried powder(s). When reagents and/or components are provided as a dry powder, the powder can be reconstituted by the addition of a suitable solvent. It is envisioned that the solvent may also be provided in another container means. The kits may also comprise a second container means for containing a sterile, pharmaceutically acceptable buffer and/or other diluent.

In particular embodiments of the disclosure, cells that are to be used for cell therapy are provided in a kit, and in some cases the cells are essentially the sole component of the kit. The kit may comprise reagents and materials to make the desired cell. In specific embodiments, the reagents and materials include primers for amplifying desired sequences, nucleotides, suitable buffers or buffer reagents, salt, and so forth, and in some cases the reagents include vectors and/or DNA that encodes a chimeric cytokine receptor as described herein and/or regulatory elements therefor.

In particular embodiments, there are one or more apparatuses in the kit suitable for extracting one or more samples from an individual and/or for delivering cells to an individual. The apparatus may be a syringe, scalpel, and so forth.

In some cases of the disclosure, the kit, in addition to cell therapy embodiments, also includes a second cancer therapy, such as chemotherapy, hormone therapy, and/or another immunotherapy, for example. The kit(s) may be tailored to a particular cancer for an individual and comprise respective second cancer therapies for the individual.

VII. Combination Therapy

In certain embodiments of the disclosure, methods of the present disclosure for clinical aspects are combined with other agents effective in the treatment of hyperproliferative disease, such as anti-cancer agents. An "anti-cancer" agent is capable of negatively affecting cancer in a subject, for example, by killing cancer cells, inducing apoptosis in cancer cells, reducing the growth rate of cancer cells, reducing the incidence or number of metastases, reducing tumor size, inhibiting tumor growth, reducing the blood supply to a tumor or cancer cells, promoting an immune response against cancer cells or a tumor, preventing or inhibiting the progression of cancer, or increasing the lifespan of a subject with cancer. More generally, these other compositions would be provided in a combined amount effective to kill or inhibit proliferation of the cell. This process may involve contacting the cancer cells with the expression construct and the agent(s) or multiple factor(s) at the same time. This may be achieved by contacting the cell with a single composition or pharmacological formulation that includes both agents, or by contacting the cell with two distinct compositions or formulations, at the same time, wherein one composition includes the expression construct and the other includes the second agent(s).

Tumor cell resistance to chemotherapy and radiotherapy agents represents a major problem in clinical oncology. One goal of current cancer research is to find ways to improve the efficacy of chemo- and radiotherapy by combining it with other therapy. In the context of the present disclosure, it is contemplated that the cell therapy could be used similarly in conjunction with chemotherapeutic, radiotherapeutic, and/or immunotherapeutic intervention.

Alternatively, the present inventive cell therapy may precede or follow the other agent treatment by intervals ranging from minutes to weeks. In embodiments where the other agent and present disclosure are applied separately to the individual, one would generally ensure that a significant period of time did not expire between the time of each delivery, such that the agent and inventive therapy would still be able to exert an advantageously combined effect on the cell. In such instances, it is contemplated that one may contact the cell with both modalities within about 12-24 h of each other and, more preferably, within about 6-12 h of each other. In some situations, it may be desirable to extend the time period for treatment significantly, however, where several d (2, 3, 4, 5, 6 or 7) to several wk (1, 2, 3, 4, 5, 6, 7 or 8) lapse between the respective administrations.

Various combinations may be employed, present disclosure is "A" and the secondary agent, such as radio- or chemotherapy, is "B":

```
A/B/A  B/A/B  B/B/A  A/A/B  A/B/B  B/A/A  A/B/B/B  B/A/B/B
B/B/B/A  B/B/A/B  A/A/B/B  A/B/A/B  A/B/B/A  B/B/A/A
B/A/B/A  B/A/A/B  A/A/A/B  B/A/A/A  A/B/A/A  A/A/B/A
```

It is expected that the treatment cycles would be repeated as necessary. It also is contemplated that various standard therapies, as well as surgical intervention, may be applied in combination with the inventive cell therapy.

A. Chemotherapy

Cancer therapies also include a variety of combination therapies with both chemical and radiation based treatments. Combination anti-cancer agents include, for example, acivicin; aclarubicin; acodazole hydrochloride; acronine; adozelesin; aldesleukin; altretamine; ambomycin; ametantrone acetate; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; celecoxib (COX-2 inhibitor); chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; ilmofosine; iproplatin; irinotecan; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; taxotere; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride; 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; doxorubicin; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imatinib (e.g., GLEEVEC®), imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mitoguazone; mitolactol; mitomycin analogues; mitonafide; mitotoxin fibroblast growth factor-saporin; mitoxantrone; mofarotene; molgramostim; Erbitux, human chorionic gonadotrophin; monophosphoryl lipid A+myobacterium cell wall sk; mopidamol; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin: neridronic acid; nilutamide; nisamycin; nitric oxide modulators; nitroxide antioxidant; nitrullyn; oblimersen (GENASENSE®); O.sup.6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stipiamide; stromelysin inhibitors; sulfinosine; superactive vasoactive intestinal peptide antagonist; suradista; suramin; swainsonine; tallimustine; tamoxifen methiodide; tauromustine; tazarotene; tecogalan sodium; tegafur; tellurapyrylium; telomerase inhibitors; temoporfin; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; velaresol; veramine; verdins; verteporfin; vinorelbine; vinxaltine; vitaxin; vorozole; zanoterone; zeniplatin; zilascorb; and zinostatin stimalamer, or any analog or derivative variant of the foregoing and also combinations thereof.

In specific embodiments, chemotherapy for the individual is employed in conjunction with the disclosure, for example before, during and/or after administration of the disclosure.

B. Radiotherapy

Other factors that cause DNA damage and have been used extensively include what are commonly known as γ-rays, X-rays, and/or the directed delivery of radioisotopes to tumor cells. Other forms of DNA damaging factors are also contemplated such as microwaves and UV-irradiation. It is most likely that all of these factors effect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

The terms "contacted" and "exposed," when applied to a cell, are used herein to describe the process by which a therapeutic construct and a chemotherapeutic or radiotherapeutic agent are delivered to a target cell or are placed in direct juxtaposition with the target cell. To achieve cell killing or stasis, both agents are delivered to a cell in a combined amount effective to kill the cell or prevent it from dividing.

C. Immunotherapy

Immunotherapeutics generally rely on the use of immune effector cells and molecules to target and destroy cancer cells, and immunotherapeutics other than the chimeric cytokine-expressing cells of the disclosure may be used, in certain embodiments. The immune effector may be, for example, an antibody specific for some marker on the surface of a tumor cell. The antibody alone may serve as an effector of therapy or it may recruit other cells to actually effect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

Immunotherapy other than the inventive therapy described herein could thus be used as part of a combined therapy, in conjunction with the present cell therapy. The general approach for combined therapy is discussed below. Generally, the tumor cell must bear some marker that is amenable to targeting, i.e., is not present on the majority of other cells. Many tumor markers exist and any of these may be suitable for targeting in the context of the present disclosure. Common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155.

In certain other embodiments, the immunotherapy comprises use of an antibody against DLL4, Notch, or a Wnt pathway protein, for example.

D. Genes

In yet another embodiment, the secondary treatment is a gene therapy in which a therapeutic polynucleotide is administered before, after, or at the same time as the present disclosure clinical embodiments. A variety of expression products are encompassed within the disclosure, including inducers of cellular proliferation, inhibitors of cellular proliferation, or regulators of programmed cell death.

E. Surgery

Approximately 60% of persons with cancer will undergo surgery of some type, which includes preventative, diagnostic or staging, curative and palliative surgery. Curative surgery is a cancer treatment that may be used in conjunction with other therapies, such as the treatment of the present disclosure, chemotherapy, radiotherapy, hormonal therapy, gene therapy, immunotherapy and/or alternative therapies.

Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and miscopically controlled surgery (Mohs' surgery). It is further contemplated that the present disclosure may be used in conjunction with removal of superficial cancers, precancers, or incidental amounts of normal tissue.

Upon excision of part of all of cancerous cells, tissue, or tumor, a cavity may be formed in the body. Treatment may be accomplished by perfusion, direct injection or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

F. Other Agents

It is contemplated that other agents may be used in combination with the present disclosure to improve the therapeutic efficacy of treatment. These additional agents include immunomodulatory agents, agents that affect the upregulation of cell surface receptors and GAP junctions, cytostatic and differentiation agents, inhibitors of cell adhesion, or agents that increase the sensitivity of the hyperproliferative cells to apoptotic inducers. Immunomodulatory agents include tumor necrosis factor; interferon alpha, beta, and gamma; IL-2 and other cytokines; F42K and other cytokine analogs; or MIP-1, MP-theta, MCP-1, RANTES, and other chemokines. It is further contemplated that the upregulation of cell surface receptors or their ligands such as Fas/Fas ligand, DR4 or DR5/TRAIL would potentiate the apoptotic inducing abililties of the present disclosure by establishment of an autocrine or paracrine effect on hyperproliferative cells. Increases intercellular signaling by elevating the number of GAP junctions would increase the anti-hyperproliferative effects on the neighboring hyperproliferative cell population. In other embodiments, cytostatic or differentiation agents can be used in combination with the present disclosure to improve the anti-hyperproliferative efficacy of the treatments Inhibitors of cell adhesion are contemplated to improve the efficacy of the present disclosure. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with the present disclosure to improve the treatment efficacy.

EXAMPLES

The following examples are included to demonstrate preferred embodiments of the disclosure. It should be appreciated by those of skill in the art that the techniques disclosed in the examples that follow represent techniques discovered by the inventor to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1

Exemplary Embodiments of the Disclosure

Figure 2:
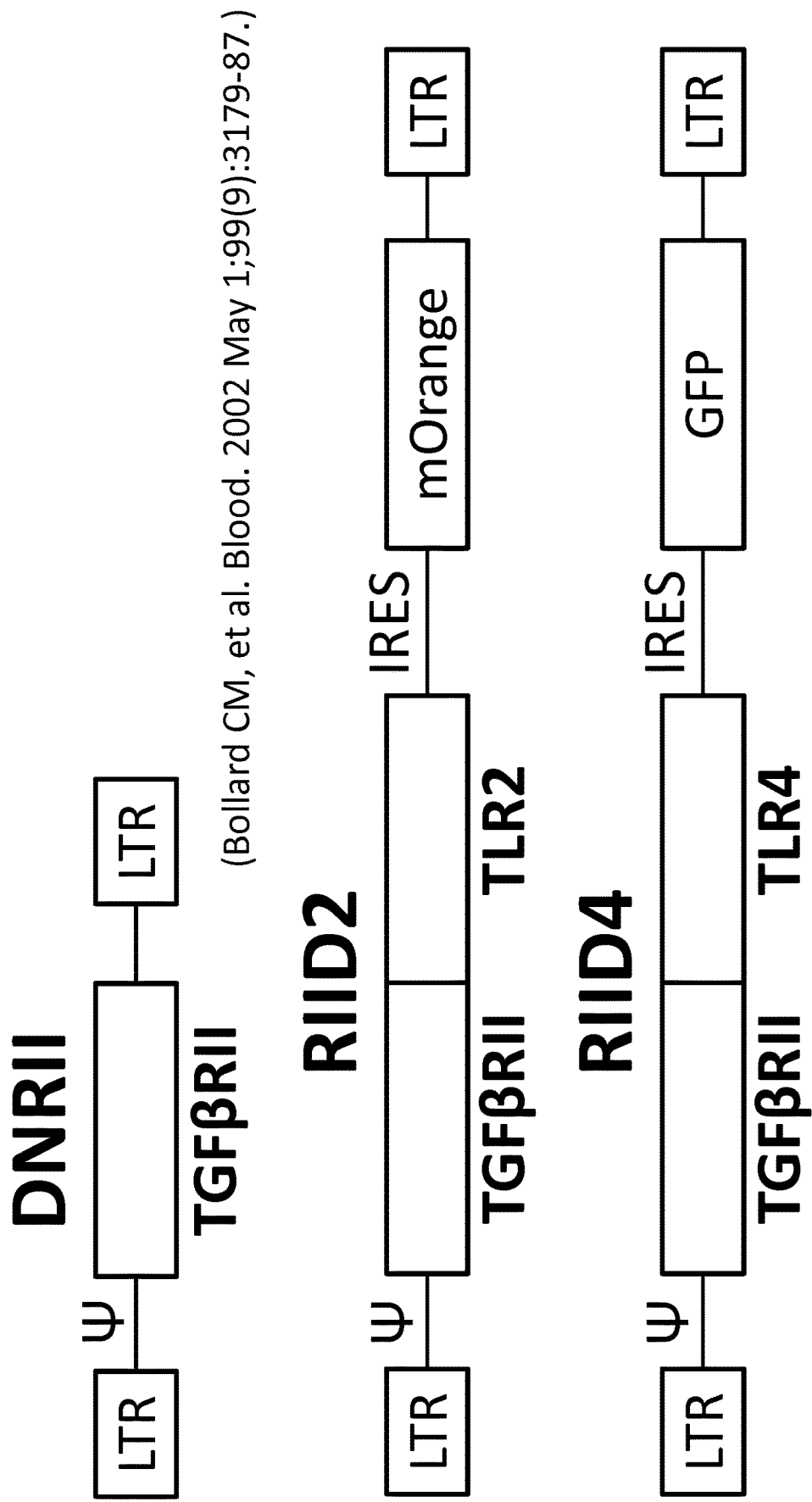
FIG. 2 provides exemplary retroviral vector maps of the control DNRII, RIID2 and RIID4.

FIG. 1 illustrates an exemplary method to arm T cells to overcome the inhibitory tumor microenvironment. The method permits conversion of an inhibitory signal from TGFβ into a positive signal for proliferation of tumor-specific CTLs (for example). The conversion location occurs at a receptor for TGFb wherein the receptor employs the cytokine receptor exodomain with an endodomain that transmits the signal instead as a positive one. FIG. 2 provides exemplary vectors suitable for the disclosure by encoding chimeric TGFβ receptors, including one that employs a TLR2 endodomain (RIID2) or one that employs a TLR4 endodomain (referred to herein as RIID4). A control is shown that is a dominant negative receptor including the TGFβ receptor exodomain with no endodomain. Although any type of vector may include the expression construct, retroviral vectors were employed.

Figure 3:
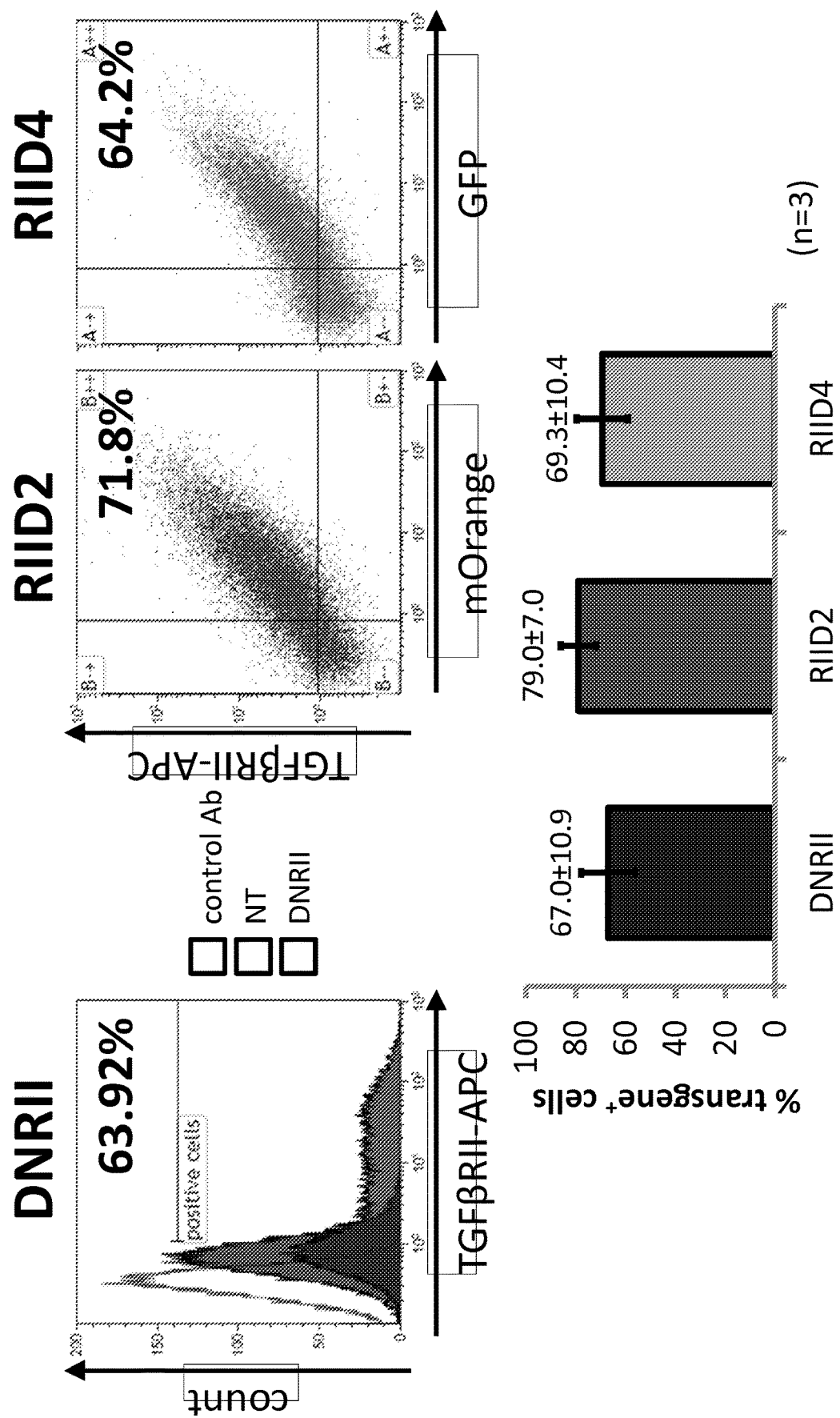
FIG. 3 shows generation of DNRII, RIID2 and RIID4 transgenic T cells.

FIG. 3 demonstrates generation of the DNRII control and exemplary chimeric TGFβ receptors of RIID2 and RIID4. The flow cytometry images demonstrate the percentage of cells expressing the particular chimeric receptors (FIG. 3).

Figure 4A:
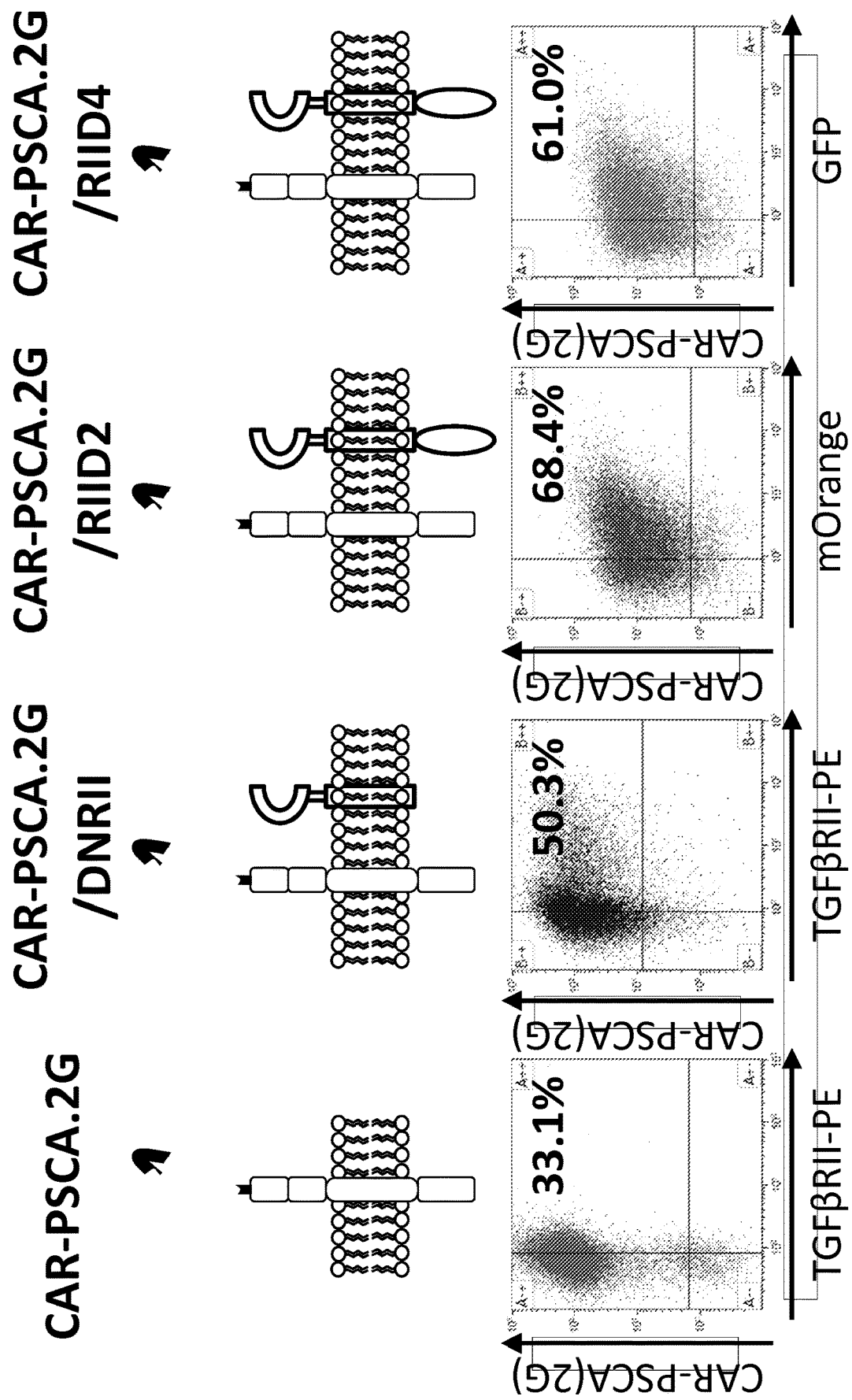
FIGS. 4A-4B demonstrate determination of co-expression of DNRII, RIID2 and RIID4 with CAR-PSCA.2G.
Figure 4B:
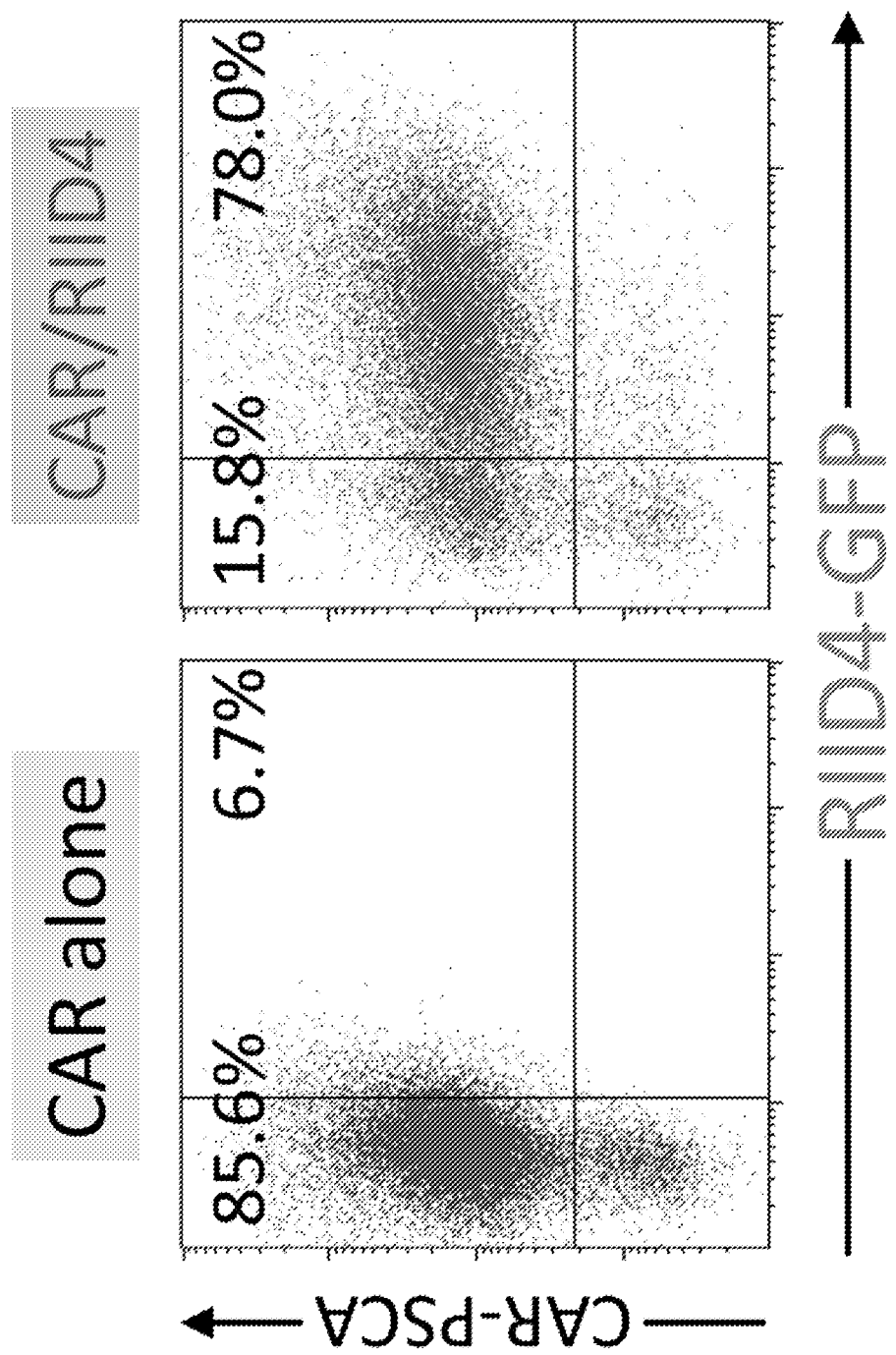

FIG. 4A demonstrates co-expression of the dominant negative control DNRII and the exemplary chimeric TGFβ receptors of RIID2 (labeled with mOrange) and RIID4 (labeled with GFP) with an exemplary second generation chimeric antigen receptor (CAR) specific for PSCA. FIG. 4B further demonstrates that RIID4 can be expressed on second generation CAR-PSCA T cells.

Figure 5:
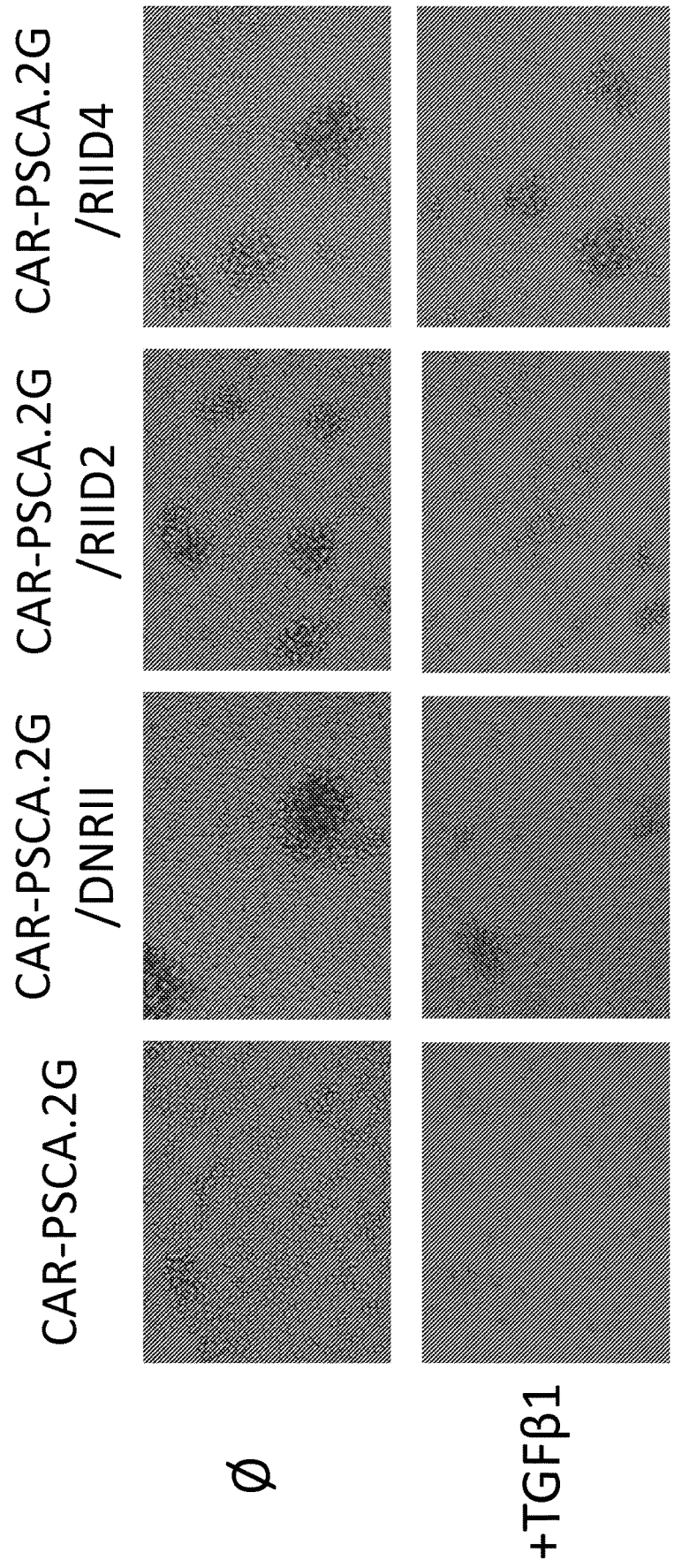
FIG. 5 demonstrates whether RIID2 and RIID4 protect CAR-modified T cells exposed to TGFβ.

FIG. 5 shows that RIID2 and RIID4 protect CAR-modified T cells exposed to TGFβ. T cells that are in a healthy environment and proliferating are visualized under a microscope as clusters of cells (weekly antigen stimulation and administration of 5 ng/ml of TGFβ1; no IL2 administration). FIG. 5 shows that although control DNRII and RIID2 show some clustering of the cells in the presence of TGFβ1, the RIID4 cells are nearly indistinguishable when comparing the absence and presence of TGFβ1.

Figure 6A:
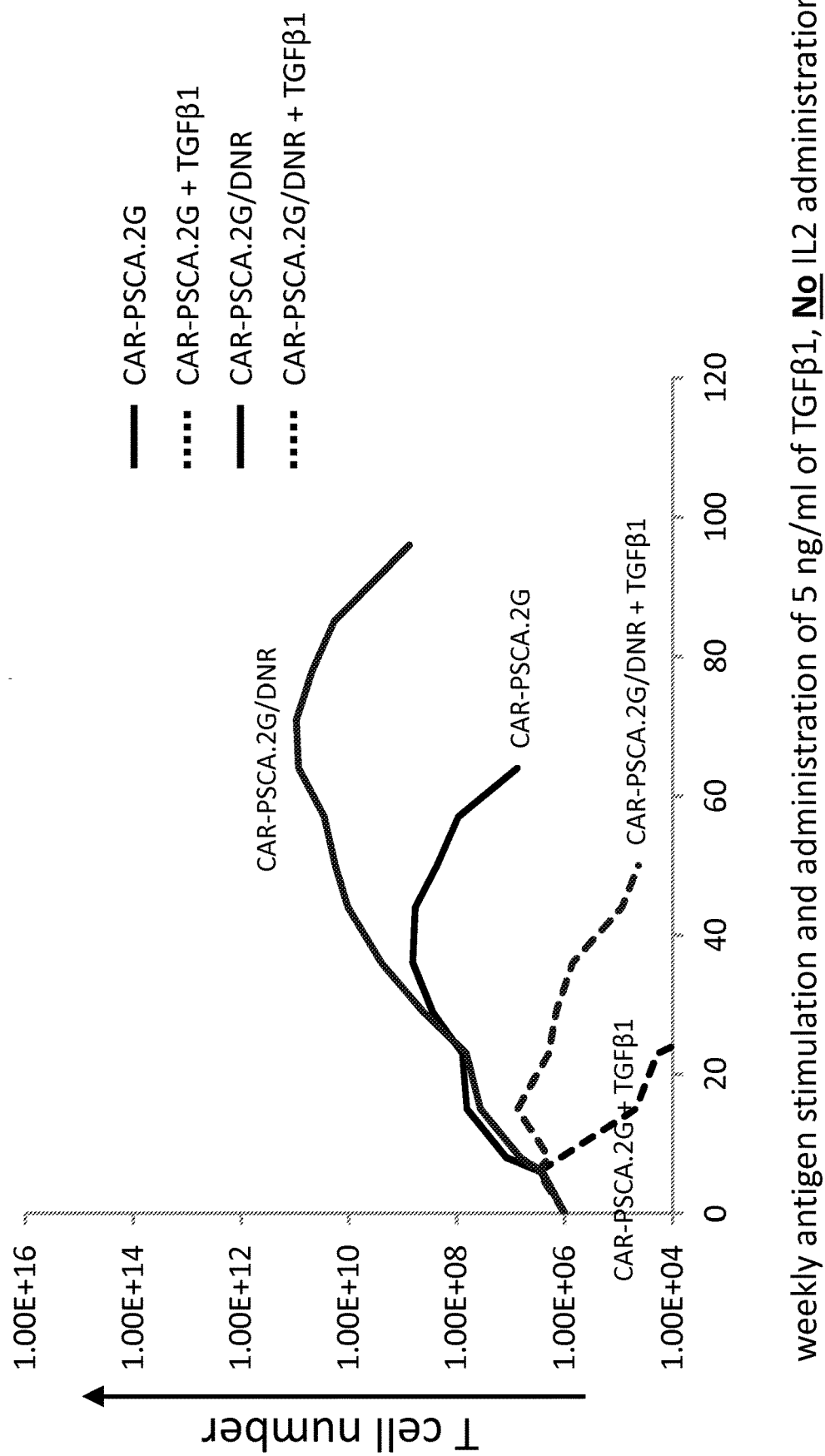
FIGS. 6A-6C show whether in suppressive conditions RIID2- and RIID4-modified T cells are protected.
Figure 6B:
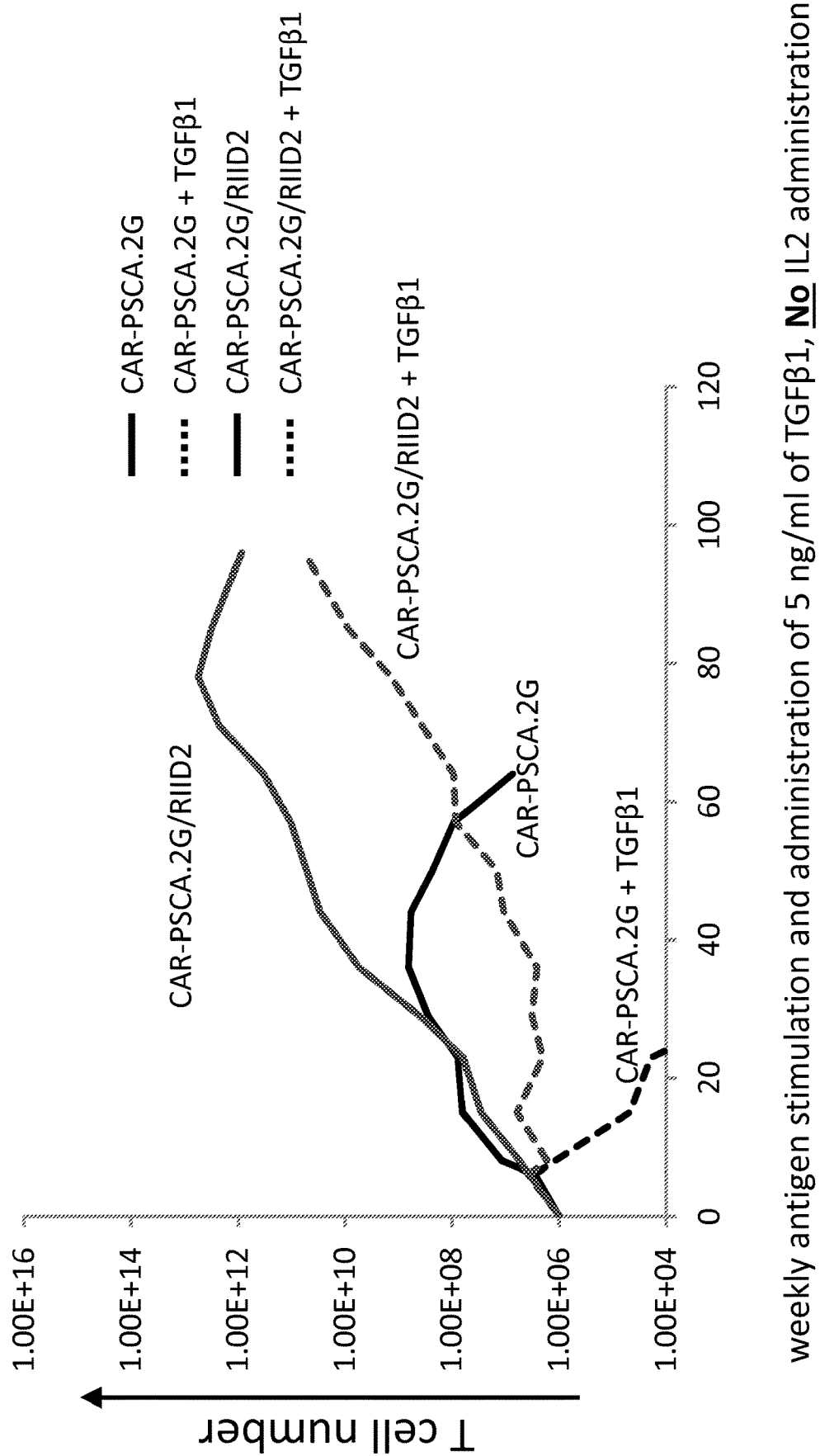
Figure 6C:
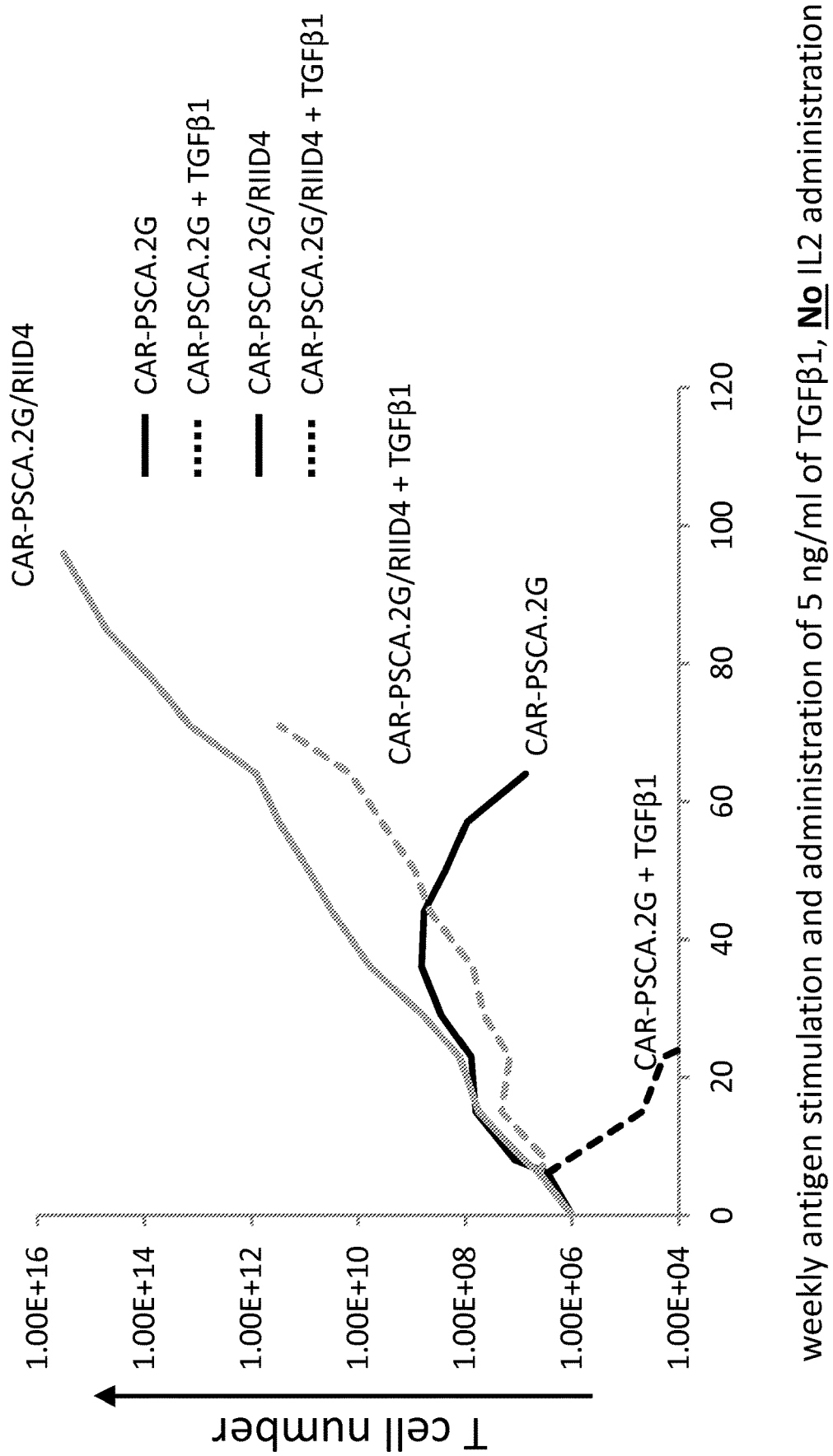

FIGS. 6A through 6C show that in suppressive conditions RIID2- and RIID4-modified T cells are protected in the presence of TGFβ. FIG. 6A demonstrates that in control cells harboring only a CAR, T cell proliferation decreases, particularly fast in the presence of TGFβ1. In the presence of the dominant negative receptor DNR, a decrease in proliferation occurs at a later time. In FIG. 6B, the presence of the chimeric TGFβ receptor RIID2 enhances proliferation, even in the presence of TGFβ. Even after almost 100 days, the cells proliferate in the presence of TGFβ. FIG. 6C also shows that in the presence of the chimeric TGFβ receptor RIID4 enhances proliferation, even in the presence of TGFβ.

Figure 7:
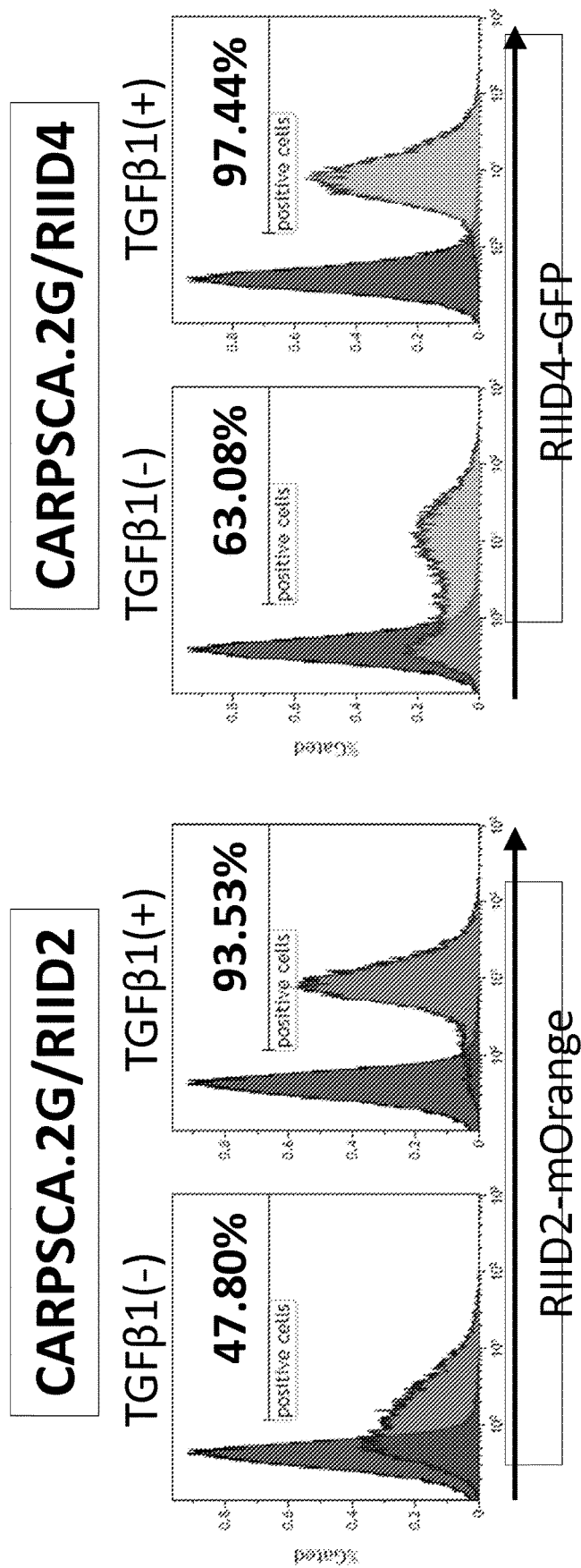
FIG. 7 shows administration of TGFβ1 selects RIID2 and RIID4-transducted T cells.
Figure 8:
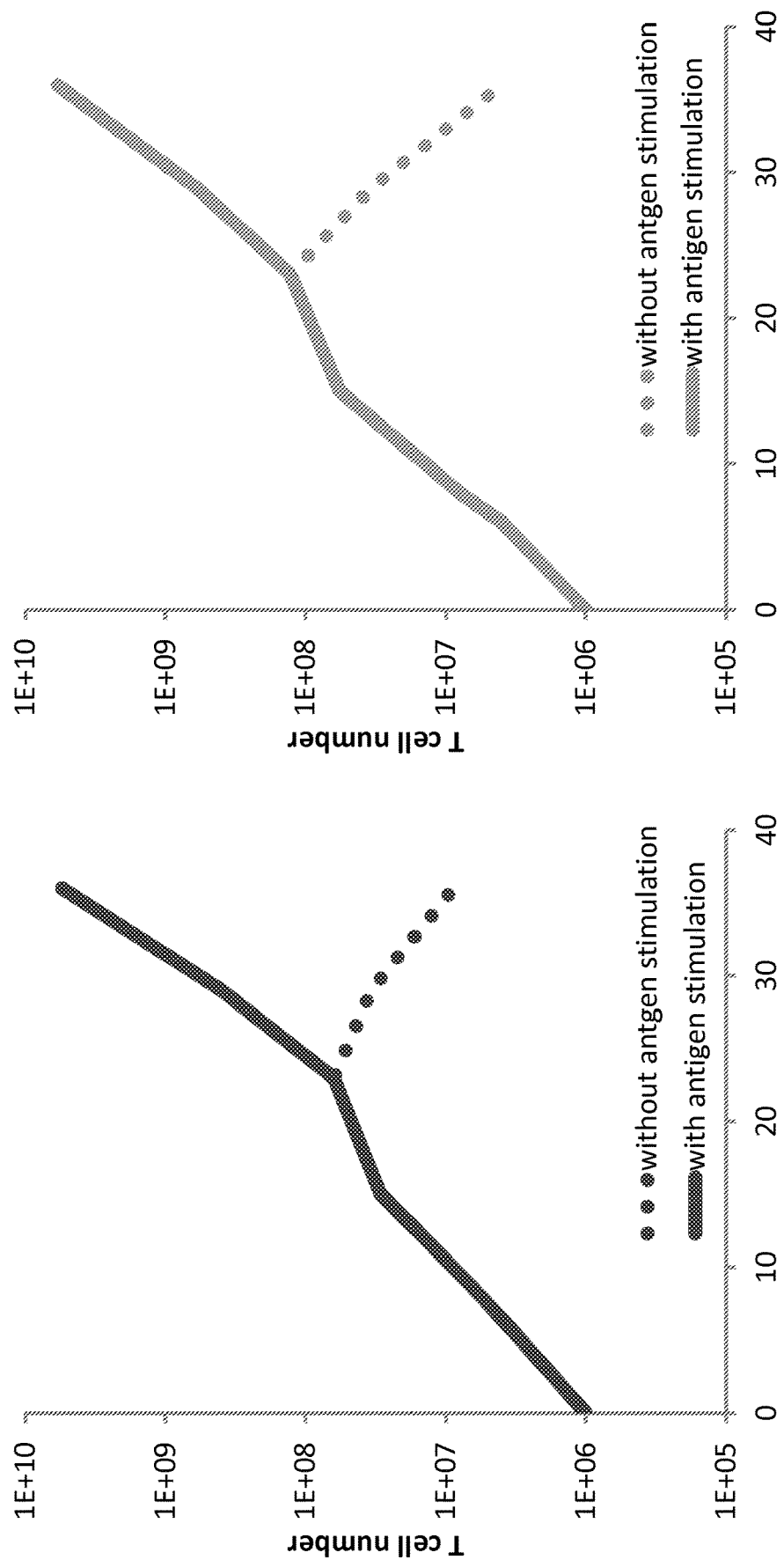
FIG. 8 demonstrates that CARPSCA.2G/RIID2 and /RIID4 T cells require antigen stimulation for their expansion.

FIG. 7 demonstrates that cells harboring the exemplary chimeric TGFβ receptors RIID2 and RIID4 are selected for in the presence of TGFβ1, and FIG. 8 demonstrates that the cells harboring RIID2 and RIID4 require antigen stimulation for their expansion. Therefore, in vivo when the cells are successful in reducing tumor load, their proliferation will decrease, in specific embodiments.

Figure 9:
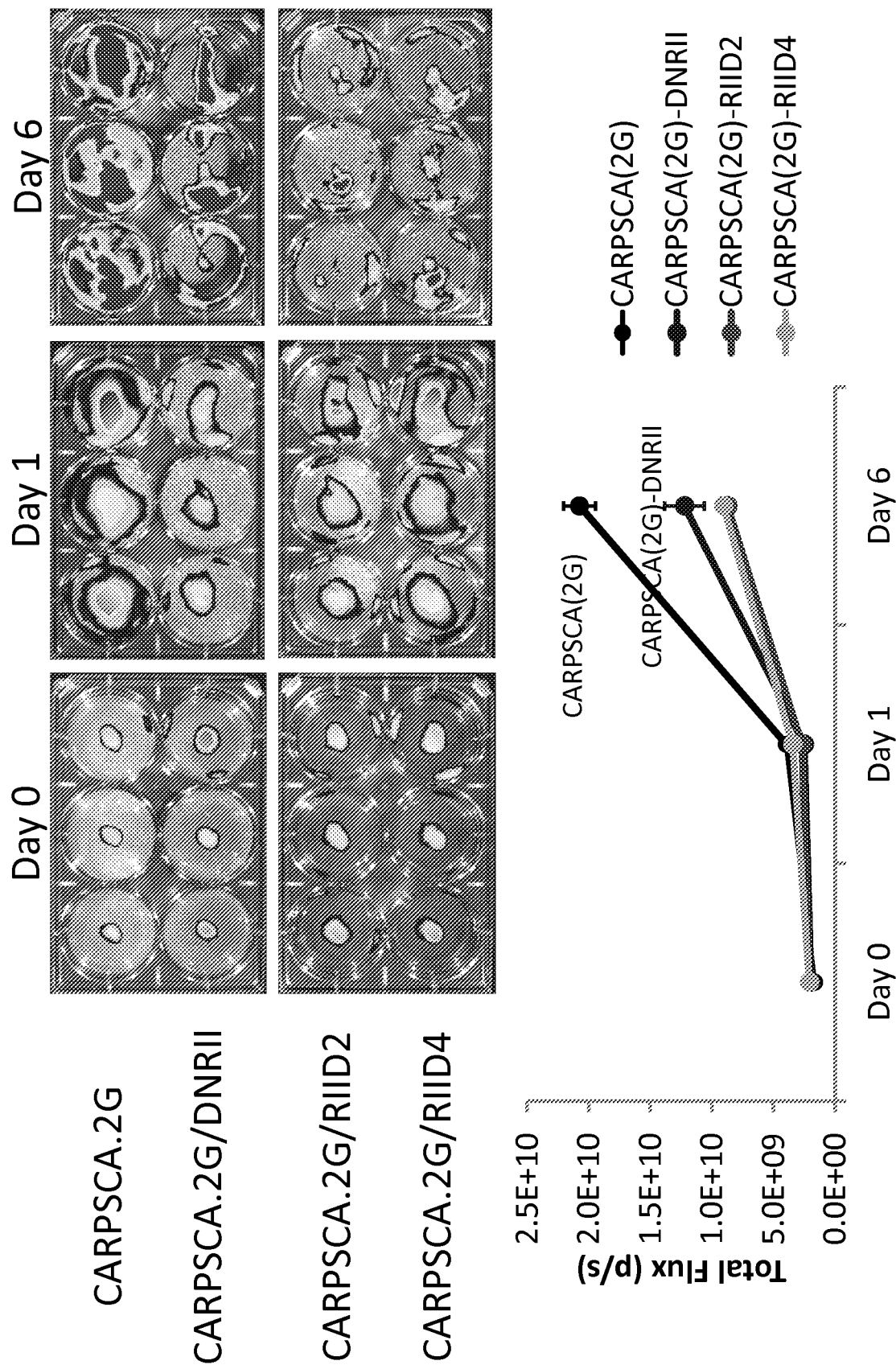
FIG. 9 provides that RIID2 and RIID4 enhance anti-tumor effect of CARPSCA.2G against DU145 cells.

FIG. 9 shows that RIID2 and RIID4 enhance the anti-tumor effect of the exemplary PSCA CAR against the exemplary DU145 prostate cancer cells.

Example 2

Immunosuppressive TGF-β Signal Converter

Chimeric antigen receptor (CAR)-transduced T cells are promising tools for the treatment of cancers. To extend this therapeutic modality to prostate cancer, the inventors generated a $2^{nd}$ generation CAR targeting the tumor antigen PSCA (2G.CAR-PSCA), which provides cells with the ability to kill PSCA+ prostate tumor cells (51.7±1.2% specific lysis of Du145 cells at 20:1 E:T). However, many tumors, including prostate cancer, secrete TGFβ, which inhibits in vivo T cell proliferation, activation and function. The present disclosure addresses this need in the art to overcome this in vivo limitation of T cells.

It has previously been demonstrated that adoptively-transferred T cells can be protected from the inhibitory effects of TGFβ through the transgenic expression of a truncated, dominant-negative receptor (DNRII), which blocks transmission of TGFβ signal. The inventors herein have extended this strategy by converting the inhibitory signal from TGFβ into an activation stimulus for T cells. The inventors generated a chimeric cytokine receptor expressing the exodomain of TGFβRII linked to the endodomain of the exemplary toll-like receptor (TLR) 4 and GFP (RIID4).

The inventors generated a chimeric cytokine receptor expressing the exodomain of TGFβRII linked to the endodomain of the exemplary toll-like receptor (TLR) 4 and GFP (RIID4). The inventors transduced primary T cells with RIID4 and obtained 69.3±6.0% transduction that was stable for >60 days of culture.

To address whether transgenic expression of RIID4 protected against TGFβ, the inventors modified 2G.CAR-PSCA T cells to co-express either the dominant negative DNRII or RIID4 receptors. These T cells were then stimulated weekly with PSCA+ tumor cells (K562-PSCA) with or without exogenous TGFβ1 (5 ng/mL). In the absence of TGFβ1, 2G.CAR-PSCA, 2G.CAR-PSCA(DNRII) or 2G.CAR-PSCA(RIID4) T cells proliferated at similar levels for 30 days ($6.4 \times 10^2$, $2.5 \times 10^3$, $5.9 \times 10^3$ fold, respectively). But, in the presence of TGFβ1, 2G.CAR-PSCA T cells did not expand, and cultures failed within 2 weeks. In contrast, transgenic expression of DNRII or RIID4 protected the cells from the inhibitory impact of this cytokine (7.4 and 21 fold at 2 weeks of culture, respectively). To determine whether there were long term differences between DNRII- and RIID4-modified cells, the inventors monitored cell expansion and found that only RIID4-modified T cells were able to expand for >60 days in the presence of TGFβ1 ($3.0 \times 10^5$ fold) while DNRII cells began to contract after 30 days in culture (0.72 fold). Administration of TGFβ1 also selected 2G. CAR-PSCA(RIID4) T cells, leading to an enrichment in this transgenic cell population over time (from 63.6% to 93.3%). This modification is safe, because the administration of TGFβ1 alone was insufficient to drive transgenic T cell proliferation (0.04 fold), and the withdrawal of antigenic stimulation resulted in T cell contraction (0.02 fold). Finally, to address whether this modification could improve the anti-tumor activity of CAR-T cells, the inventors co-cultured $1 \times 10^6$ firefly-luciferase-Du145 cells, which express PSCA and produce TGFβ1, with $1 \times 10^5$ 2 G.CAR-PSCA, 2G.CAR-PSCA(DNRII) or 2G.CAR-PSCA(RIID4) T cells. After 6 days there was superior control of tumor growth by RIID4-expressing T cells compared with DNRII or CAR alone conditions (Total Flux; $9\pm0.1\times10^9$, $10\pm1\times10^9$, $20\pm1\times10^9$ p/s, respectively). Therefore, RIID4 not only protects cells from the inhibitory effects TGFβ but converts this cytokine signal into one that is stimulant.

Example 3

Chimeric Cytokine Receptors in the Tumor Microenvironment

Figure 10:
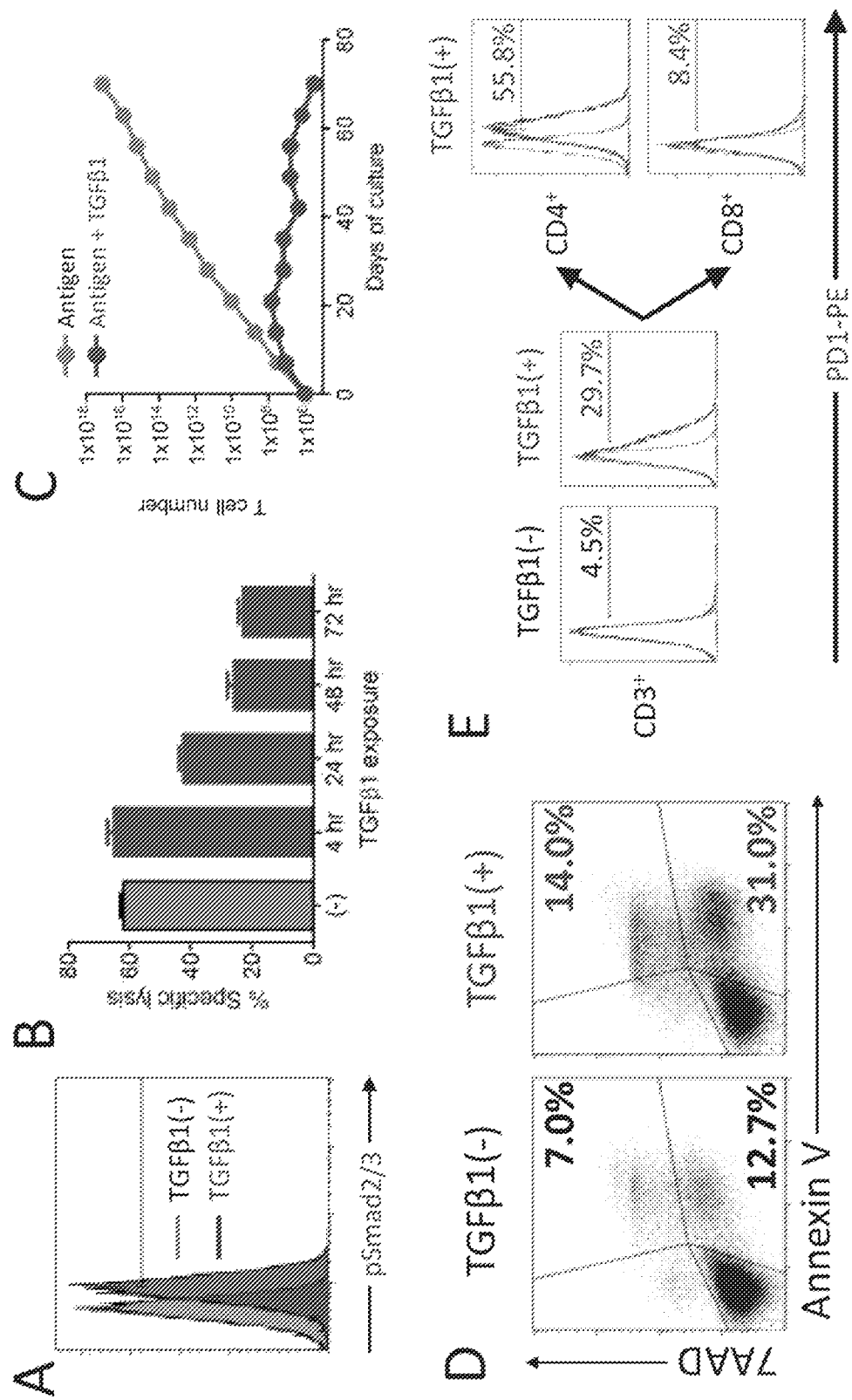
FIG. 10 shows the impact of TGFβ exposure on exemplary CAR T cells. A) signaling, B) cytolytic function, C) expansion, D) viability, and E) PD1 expression.
Figure 14:
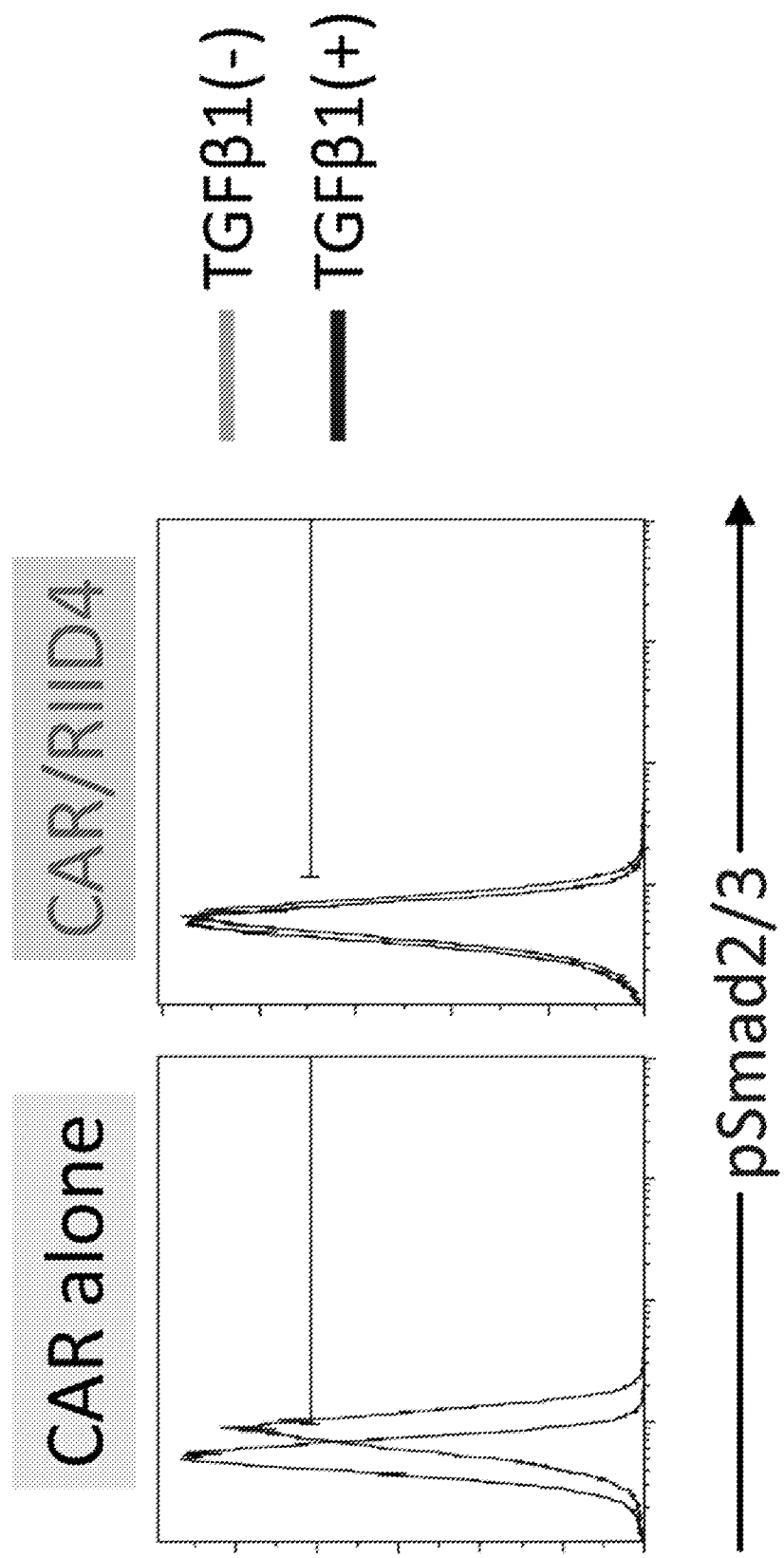
FIG. 14 demonstrates that TGFβ1 does not induce pSmad 2/3 in RIID4-modified T cells.

TGFβ has been detected at high levels in patients with cancer, including at least prostate cancer, where it acts by suppressing effector T cell function while promoting Treg development. Under wild type conditions, TGFβ engagement results in phosphorylation of Smad2/3, which triggers multiply inhibitory pathways (FIG. 10A). To evaluate the influence of TGFβ on tumor-specific T cells, CAR-PSCA T cells were cultured with TGFβ (5 ng/ml) and administered twice weekly. As expected, this resulted in phosphorylation of Smad2/3 and decreased cytolytic function in CAR-PSCA T cells (FIGS. 10A and 10B). In addition, TGFβ exposure resulted in a decrease in the expansion of CAR T cells, in part due to higher cell death (FIGS. 10C and 10D). Interestingly, exposure of CAR-PSCA T cells to TGFβ also resulted in the upregulation of PD1, suggesting T cell exhaustion (FIG. 10E). Interestingly, TGFβ1 does not induce pSmad2/3 in RIID4-modified T cells (FIG. 14).

Figure 11:
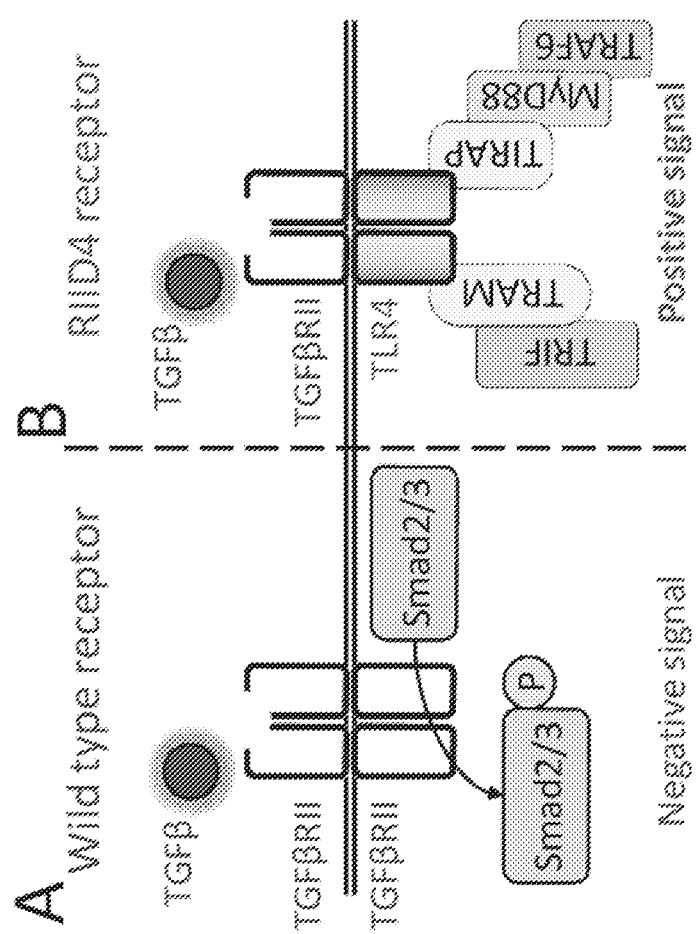
FIG. 11. illustrates A) wild type TGFβR, and B) RIID4 signaling.
Figure 12:
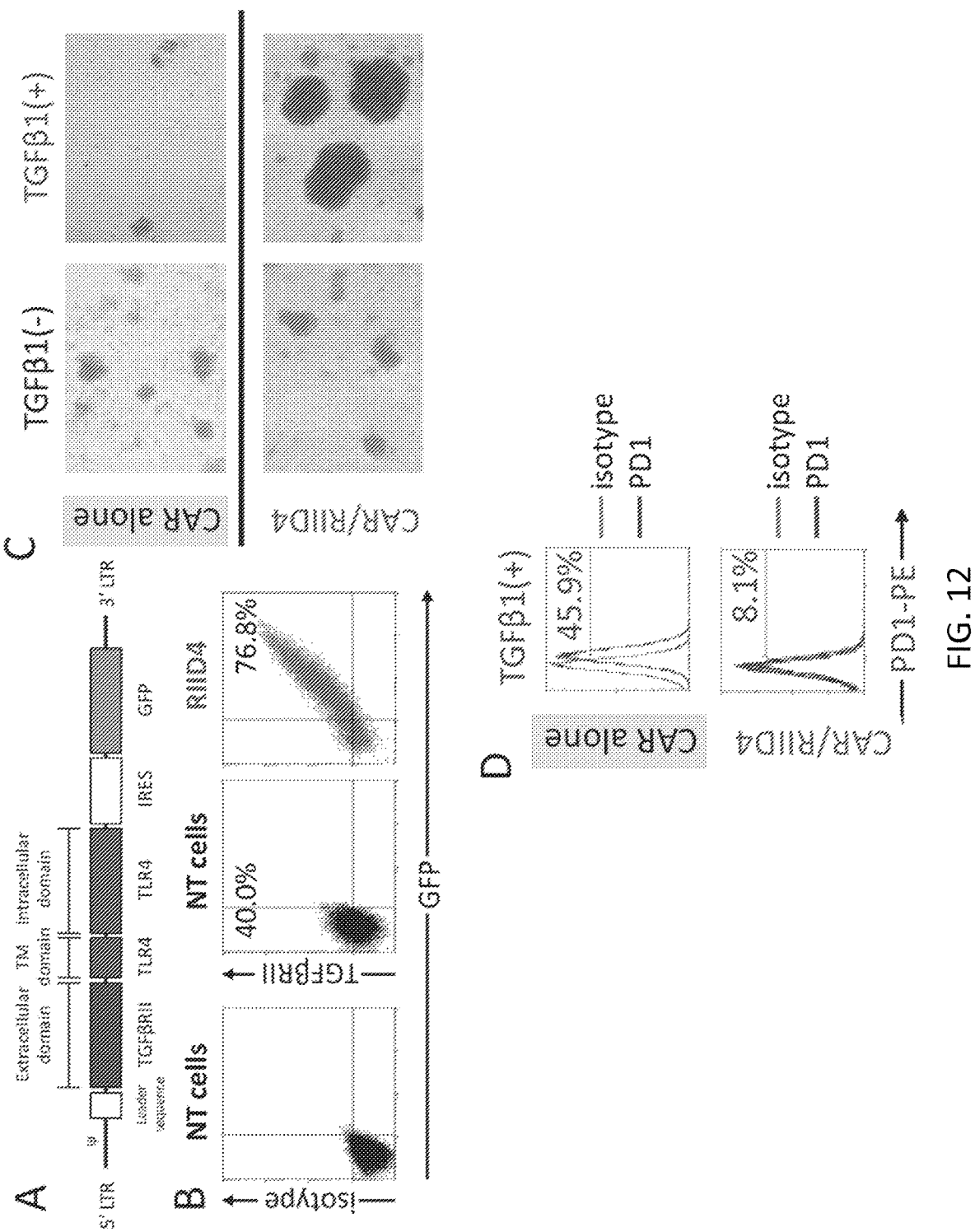
FIG. 12 illustrates A) the retroviral vector for an example of a RIID4 construct, B) expression of RIID4 on transduced cells, C) microscopic photographs of T cell cultures in presence or absence of TGFβ, and D) expression of PD1 in T cells as measured by flow.

Arming CAR-PSCA T cells against TGFβ: To determine whether Chimeric Cytokine Receptors could be utilized to protect tumor-specific T cells from the immunosuppressive effects of TGFβ, the TGFβ endodomain was substituted for that of an immunostimulatory molecule. One example of an endodomain derives from the Toll-like Receptor (TLR) family, which constitutes an important component of the innate immune response. In particular, TLR4 signaling in T cells has been demonstrated to improve T cell activation while decreasing the need for co-stimulation. Therefore, with the purpose of transforming the inhibitory signal of TGFβ into an immunostimulatory one, the TGFβR endodomain was substituted for the TLR4 endodomain (referred to herein as "RIID4") (FIGS. 11B and 12A).

RIID4 expression protects CAR T cells from TGFβ. To evaluate whether a Chimeric Cytokine Receptor could protect CAR T cells from TGFβ, a retroviral vector was generated expressing the extracellular component of TGFβR and the intracellular signaling domain of TLR4 (RIID4). This sequence was then linked with GFP using an IRES, allowing detection of the transgenic T cell population (FIG. 12A). Activated T cells were then transduced with the retroviral vector encoding for RIID4/GFP, as shown in FIG. 12B. RIID4 expression on T cells was stable as illustrated by a direct correlation of receptor expression with GFP. To evaluate the protective properties of the construct, there was co-expression of RIID4 on CAR-PSCA T cells and culturing of them in the presence of TGFβ. Importantly, only the CAR T cells expressing RIID4 were able to expand when co-cultured with TGFβ, as shown by the culture photographs in FIG. 12C. As expected, administering TGFβ to CAR T cells induced upregulation of PD1 expression. In contrast, T cells modified with the RIID4 construct did not express PD1, indicating the lack of exhaustion in these T cells (FIG. 12D).

Figure 13:
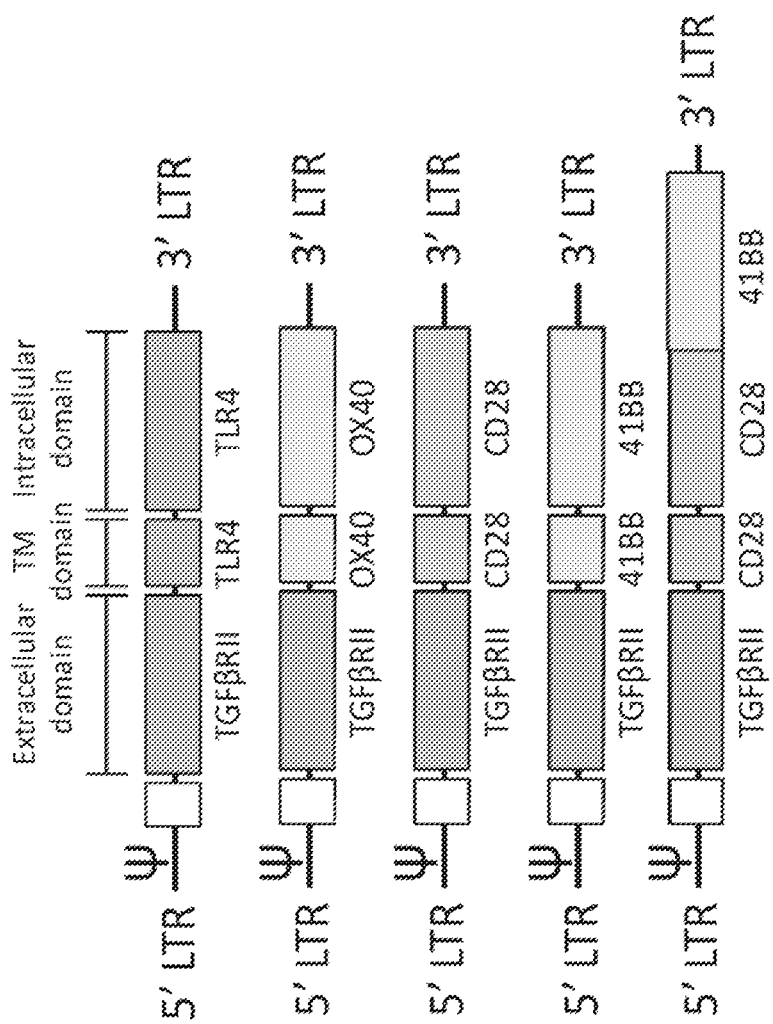
FIG. 13 illustrates exemplary chimeric cytokine retroviral receptors.

Embodiments of the disclosure extend the target range of chimeric cytokine receptors. Specific embodiments include an array of different permutations of chimeric cytokine receptors expressing the exodomain of TGFβ receptor with the endodomain of different co-stimulatory molecules as shown by example in FIG. 13. Next, one can identify which of these constructs is the most efficient in enhancing T cell function in the presence of TGFβ and determine whether the incorporation of such a modification could provide a positive bystander effect by decreasing the function of suppressive TGFβ-producing Tregs.

Vector Generation and assessment: A variety of different TGFβ/immunostimulatory endodomain constructs (TGFβR/Th1) may be generated by standard recombinant means in the art. An example of a retroviral vector expressing the exodomain of TGFβ receptor and the endodomain of TLR4, RIID4, is shown in FIG. 12A. Using this vector as an example of a template, one can subclone additional configurations by substituting the transmembrane domain and endodomain of TLR4 with OX40, CD28, 41BB, and CD28/41BB, for example. In specific embodiments the vectors may also co-express a marker, such as GFP. These different vectors may then be compared for expression and function in T cells.

Construct Assessment: To characterize the different constructs for suitability to reverse the inhibitory signaling of TGFβ, one can generate viral supernatant and transduce T cells. Protein expression can be assessed by flow cytometric analysis by correlating TGFβ receptor with GFP expression as shown in FIG. 12B. Transgenic function can be assessed by comparing T cell (i) expansion, (ii) cytokine production, (iii) phenotypic profile including expression of effector, memory and exhaustion markers and (iv) cytolytic function in the presence or absence of TGFβ, for example.

In specific embodiments, the different TGFβ cytokine receptor constructs can achieve a transduction efficiency of >60%. In specific embodiments, the constructs are stably expressed on the surface of T cells as detected by flow cytometry analysis. In general embodiments, permutations of the TGFβR/Th1 constructs exhibit superior T cell expansion, cytokine production, phenotypic profile and cytolytic function in the presence of TGFβ. However because of the difference in the co-stimulatory endodomains in certain embodiments the T cells modified with the CD28/41BB construct have a greater potential for expansion than cells expressing receptors containing a single endodomain. In certain aspects, this enhanced proliferative capacity leads to over-activation and cell exhaustion as measured by upregulation of PD1, TIM3 and LAG3, for example.

The in-vitro and in-vivo function of TGFβR/Th1 in dual-specific CTLs may be evaluated. These studies can show whether TGFβR/Th1 can be expressed by dual-specific CTLs, and whether transgenic CTLs maintain their proliferative capacity and anti-tumor activity even in the presence of TGFβ. One or more of the TGFβR/Th1 constructs may be included in a bicistronic retroviral vector. In a specific example, the bicistronic retroviral vector encodes CAR-PSCA and TGFβR/Th1.

One can confirm that CTLs maintain their function and anti-tumor activity in the presence of TGFβ by using IFNγ ELIspot with PSMA and PSCA pepmixes as stimulators, and by measuring killing using TRPC tumor as a target in the presence of TGFβ in short (4 hr $Cr^{51}$ assay), long-term (4 day co-culture) cytotoxicity assays and in TRPC tumor-bearing mice, for example.

In particular embodiments, dual-specific CTLs expressing the TGFβR/Th1 retain the antigen specificity against their respective targets (such as PSCA and PSMA). However in specific embodiments, only TGFβR/Th1 expressing T cells are functional in the presence of TGFβ resulting in a more potent in-vitro and in-vivo anti-tumor effect (Table 1).

TABLE 1

Expected Assessments of Dual-CTLs expressing Chimeric Cytokine Receptors

| | In-vitro assessment | | | | In-vivo assessment | |
|---|---|---|---|---|---|---|
| | Cell Signaling | | CTL expansion | | Tumor Growth | |
| | +IL2 | +TGFβ | +IL2 | +TGFβ | +IL2 | +TGFβ |
| Dual-CTL | Th1 | Th2 | +++ | – | (–/+) | (++++) |
| Dual-CTL-TGFβR/Th1 | Th1 | Th1 | +++ | +++ | (–/+) | (–) |

Assessing the bystander effect of TGFβR/Th1 One can evaluate the ability of TGFβR/Th1 to provide a positive bystander effect on the recipient immune system by depleting inhibitory cytokines from the tumor microenvironment. To assess this one can recapitulate the immunosuppressive tumor environment in an animal model by performing an autologous transfer of TGFβ-producing Tregs, which will deliver TGFβ at the tumor site. Experimental groups may be subdivided into two: (i) dual-CTLs-TGFβR/Th1 or (ii) dual-CTLs as a control. Two weeks after T cell treatment a cohort of mice can be sacrificed to evaluate intra-tumor levels of TGFβ as well as the number and function of the Tregs.

In specific embodiments, there is only a marginal anti-tumor response from Dual-CTLs (alone) in presence of Tregs (Table 2). In particular embodiments, and in contrast, treatment with dual-CTLs expressing the TGFβR/Th1 depletes the levels of TGFβ from the tumor microenvironment affecting the function and persistence of Tregs (Table 2), resulting in an overall enhanced anti-tumor response.

TABLE 2

Example of Outcome with Dual-CTLs comprising a Chimeric Cytokine Receptor

| | Tumor levels of TGFβ | Treg Function | Anti-tumor effect |
|---|---|---|---|
| Dual-CTLs | (++++) | (++++) | (+) |
| Dual-CTLs-TGFβR/Th1 | (–/+) | (+) | (++++) |

Figure 15:
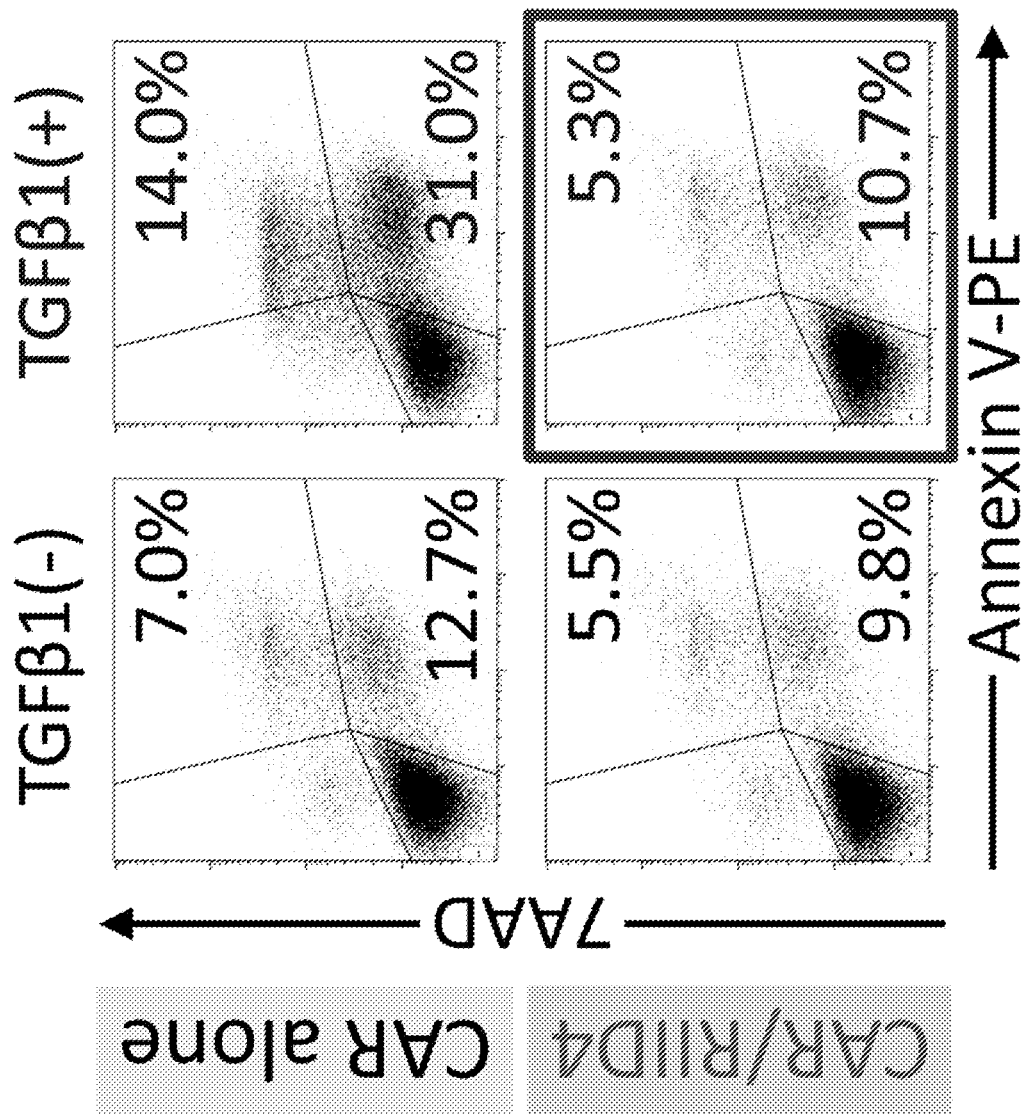
FIG. 15 shows protection by RIID4 of T cells from TGFβ1-induced apoptosis.
Figure 16:
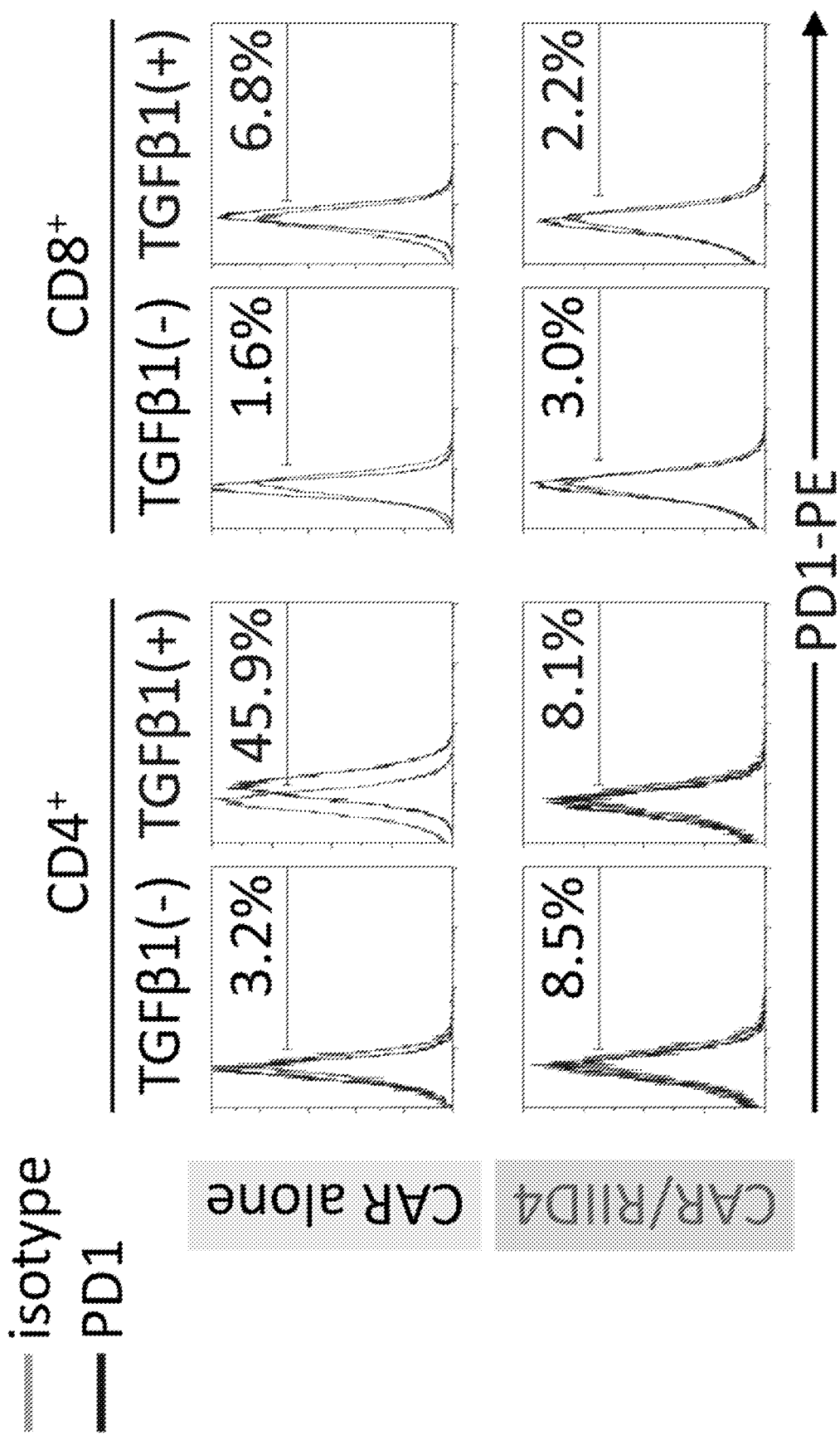
FIG. 16 demonstrates that RIID4 prevents PD1 upregulation.
Figure 17:
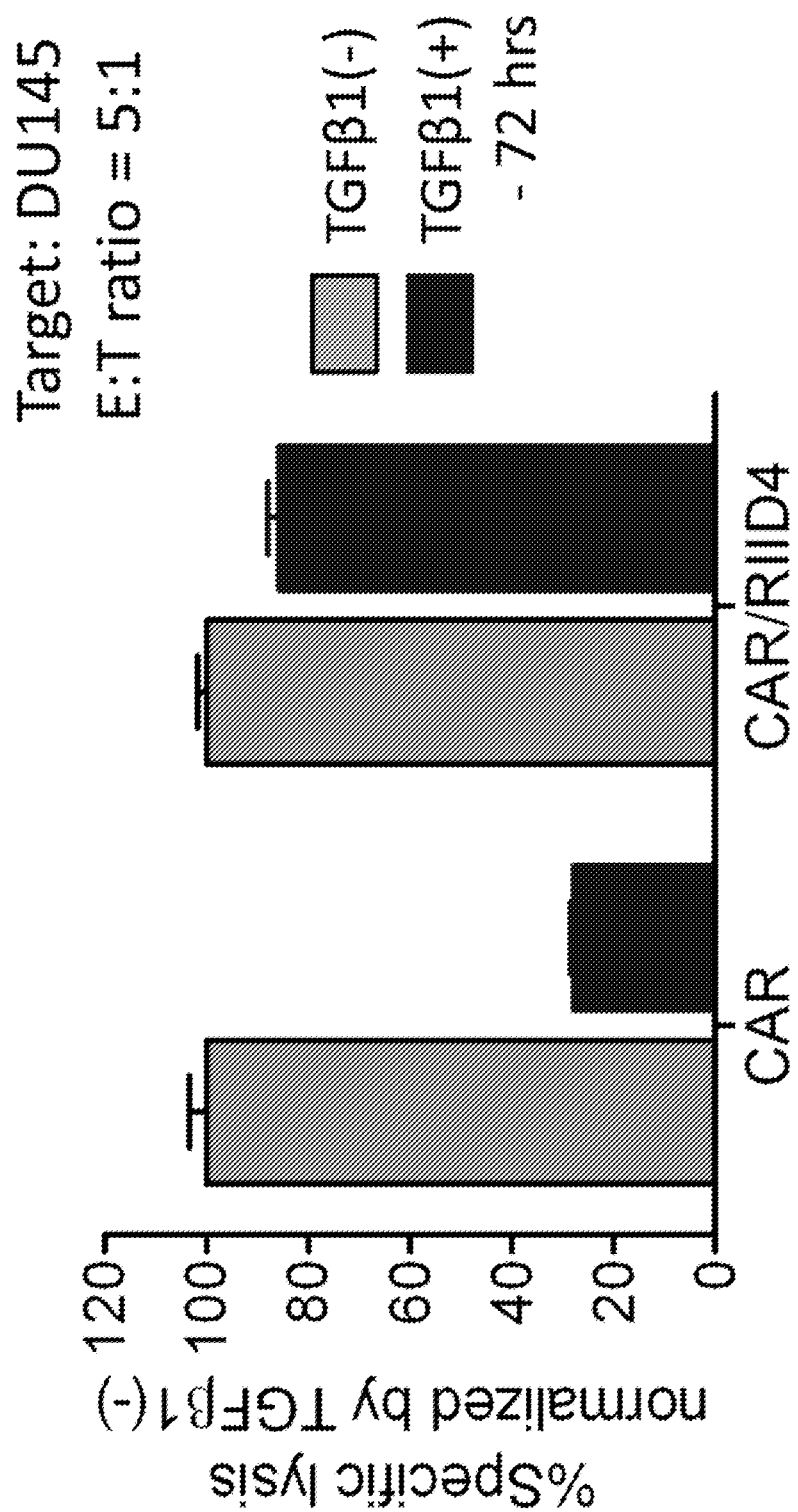
FIG. 17 demonstrates that RIID4 prevents TGFβ1-induced inhibition of cytolytic function.

T cells harboring RIID4 are protected from TGFβ1-induced apoptosis (FIG. 15); furthermore, RIID4 prevents PD1 upregulation (FIG. 16) and TGFβ1-induced inhibition of cytolytic function (FIG. 17).

Figure 18:
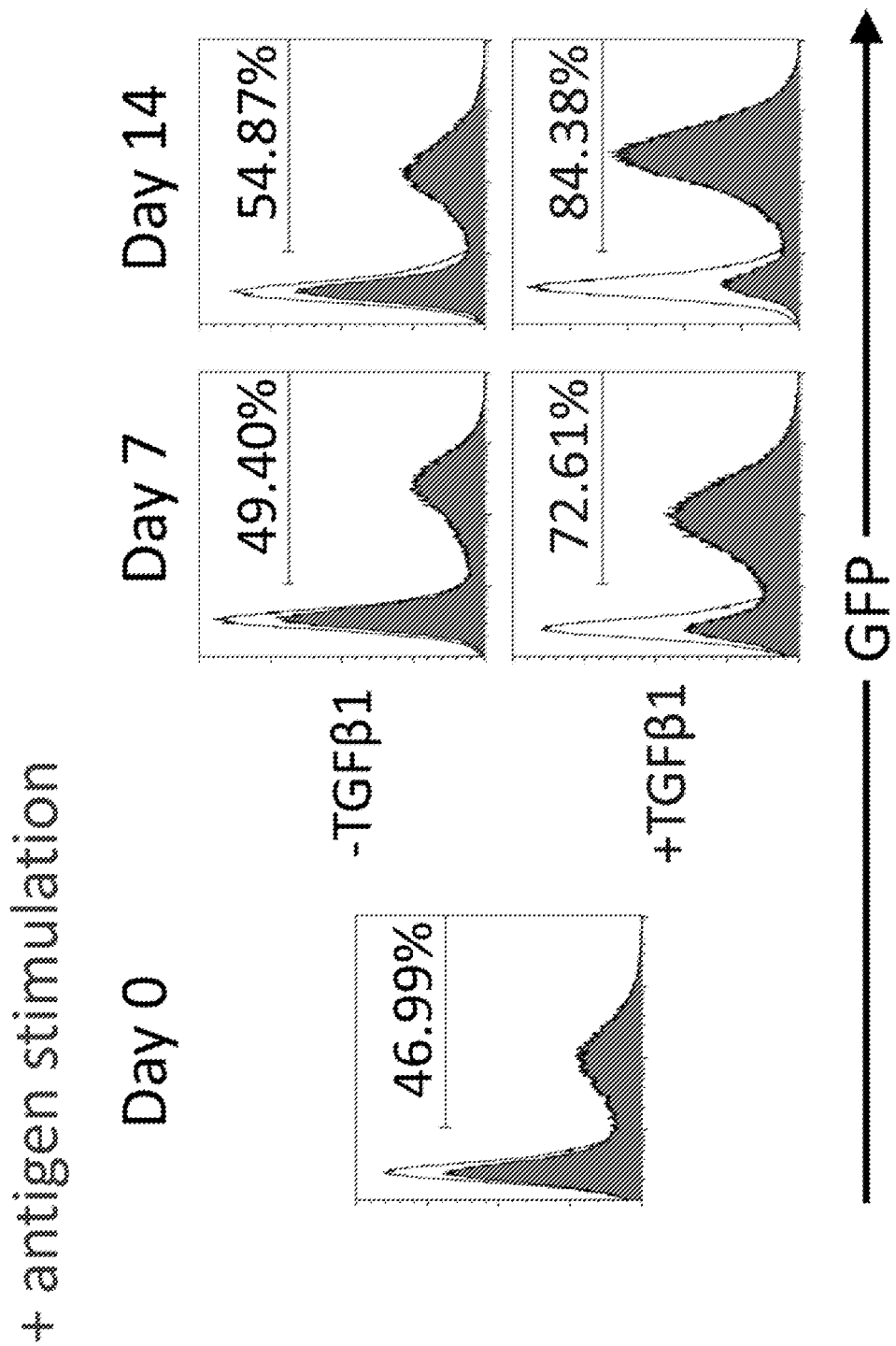
FIG. 18 shows that RIID4+ cells are selected by TGFβ1 exposure.
Figure 19:
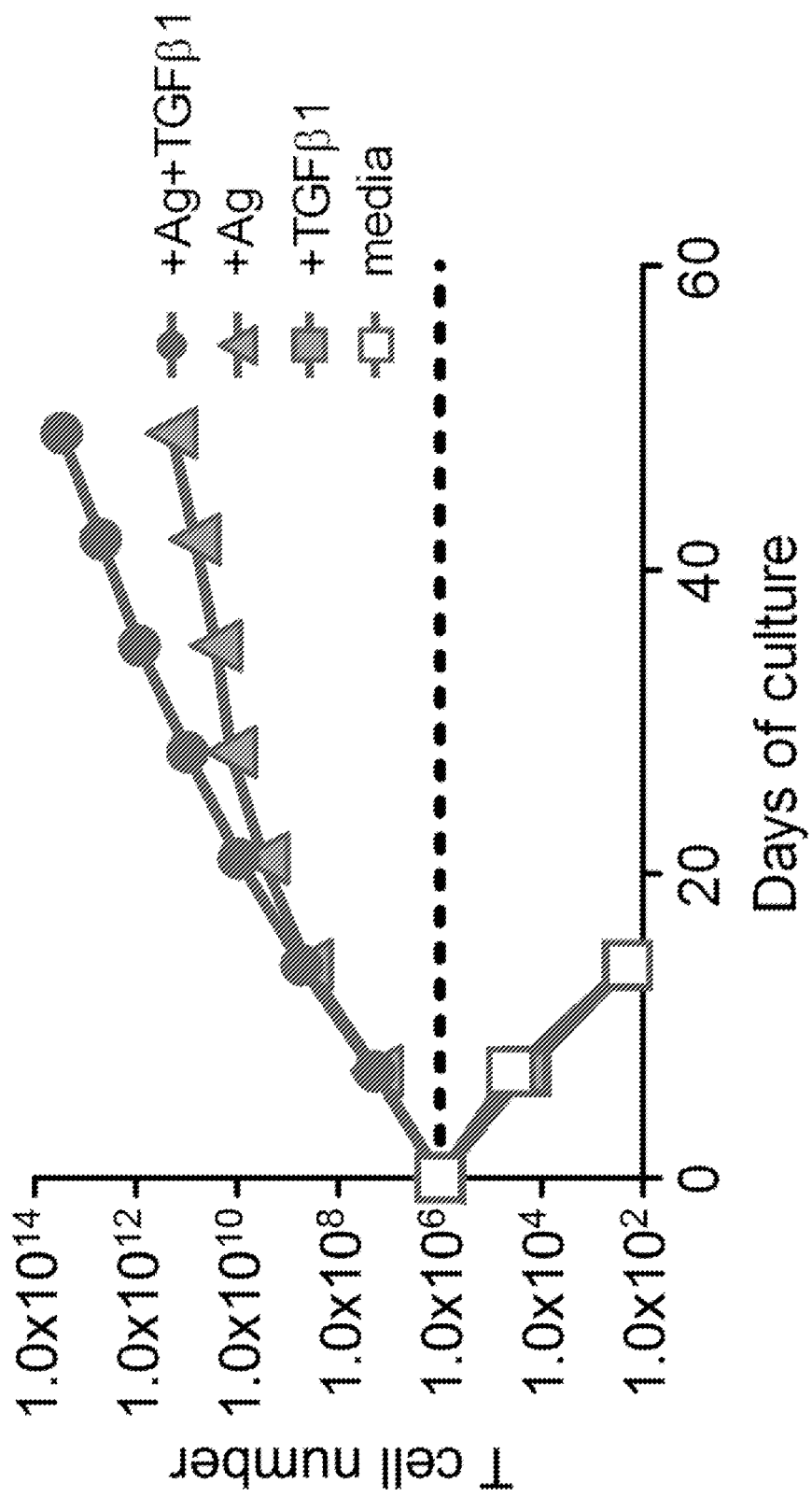
FIG. 19 demonstrates that withdrawal of antigen and TGFβ1 leads to culture failure.

FIG. 18 shows that RIID4+ cells are selected by TGFβ1 exposure, whereas withdrawal of antigen and TGFβ1 leads to culture failure (FIG. 19).

Figure 20:
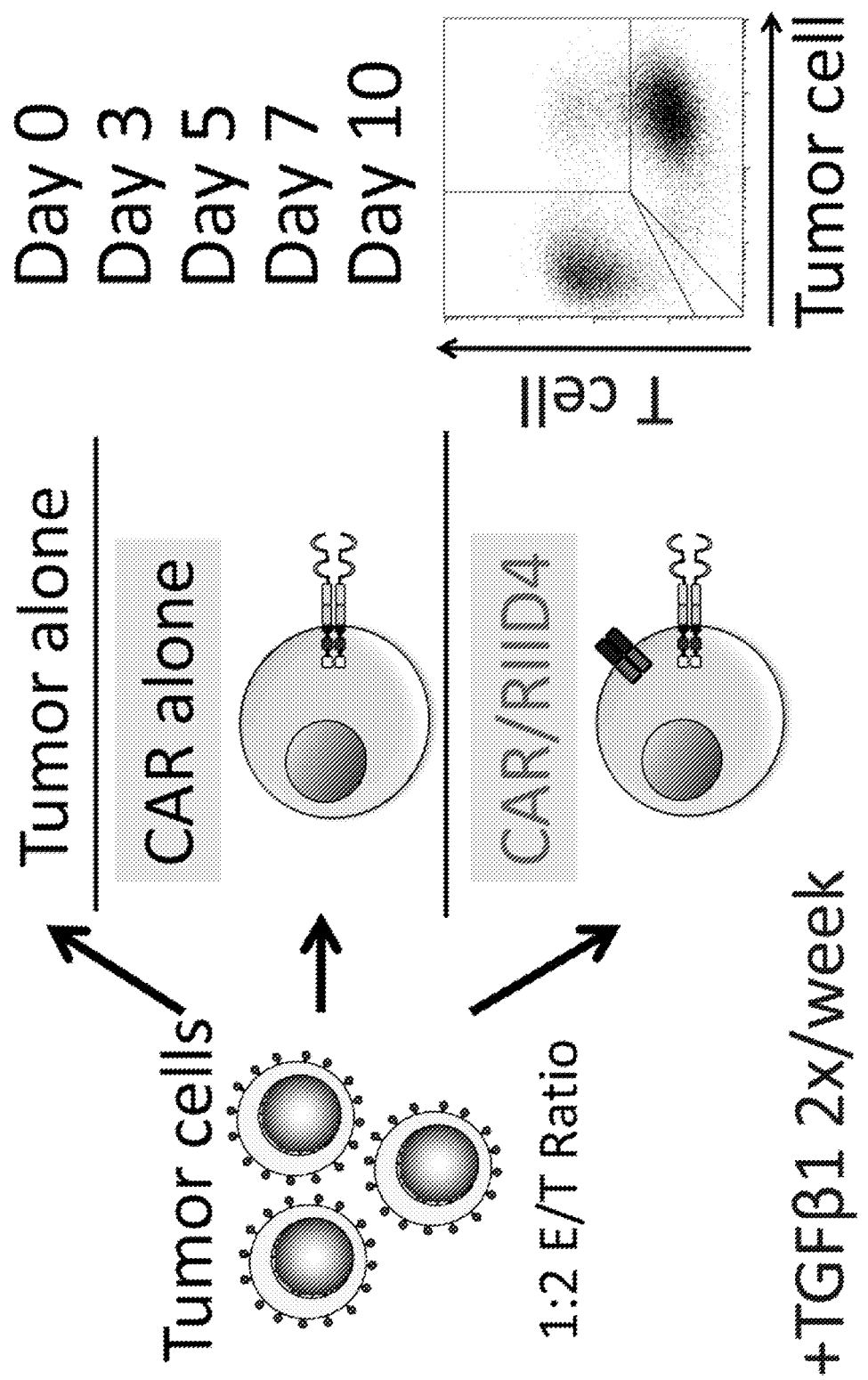
FIG. 20 illustrates an example of a co-culture experimental set-up.

FIG. 20 illustrates an example of a co-culture experimental set-up.

Figure 21:
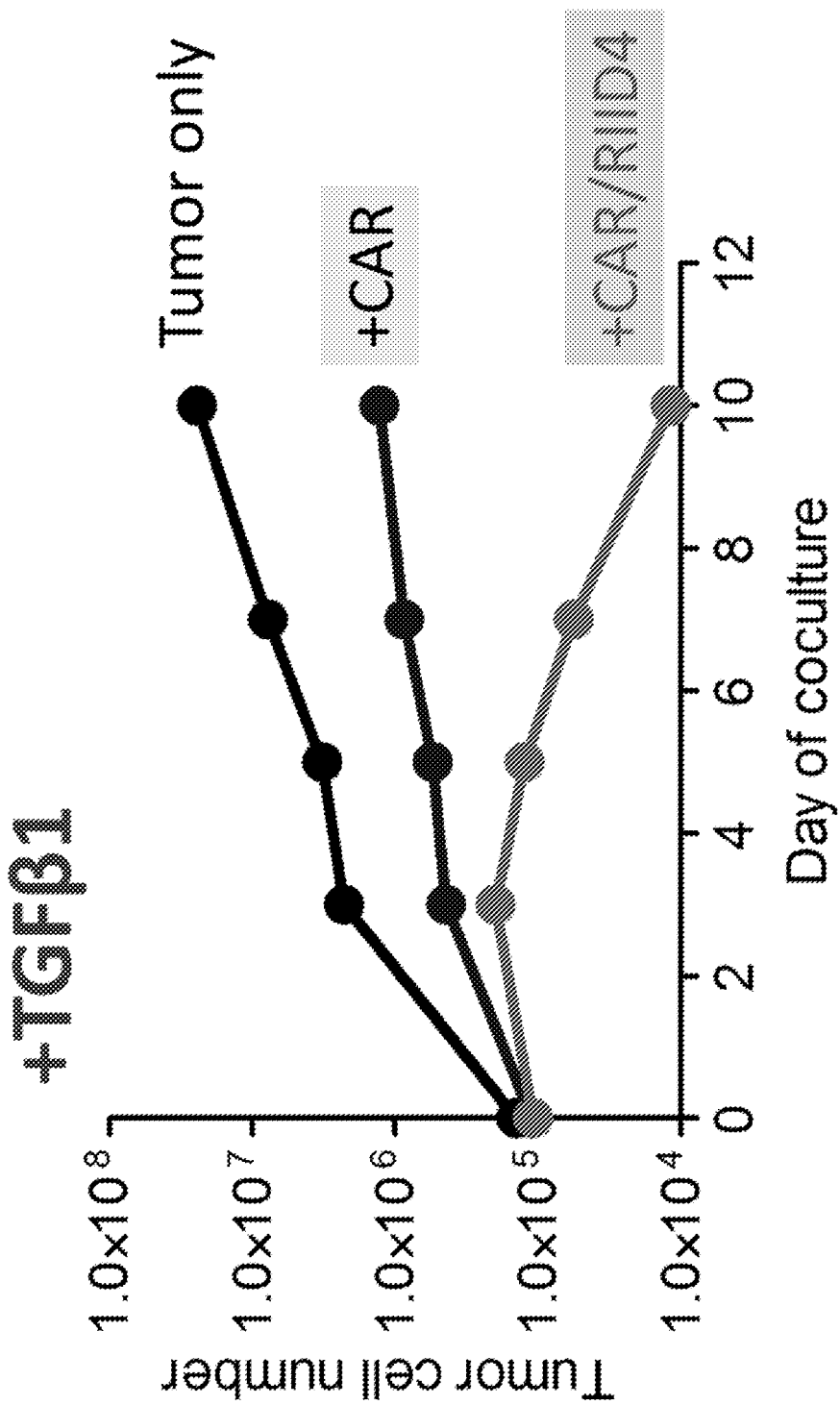
FIG. 21 provides evidence that 2G.CAR-PSCA/RIID4 cells eliminated tumors in the presence of TGFβ1.

FIG. 21 demonstrates that 2G.CAR-PSCA/RIID4 cells eliminated tumors in the presence of TGFβ1.

Figure 22:
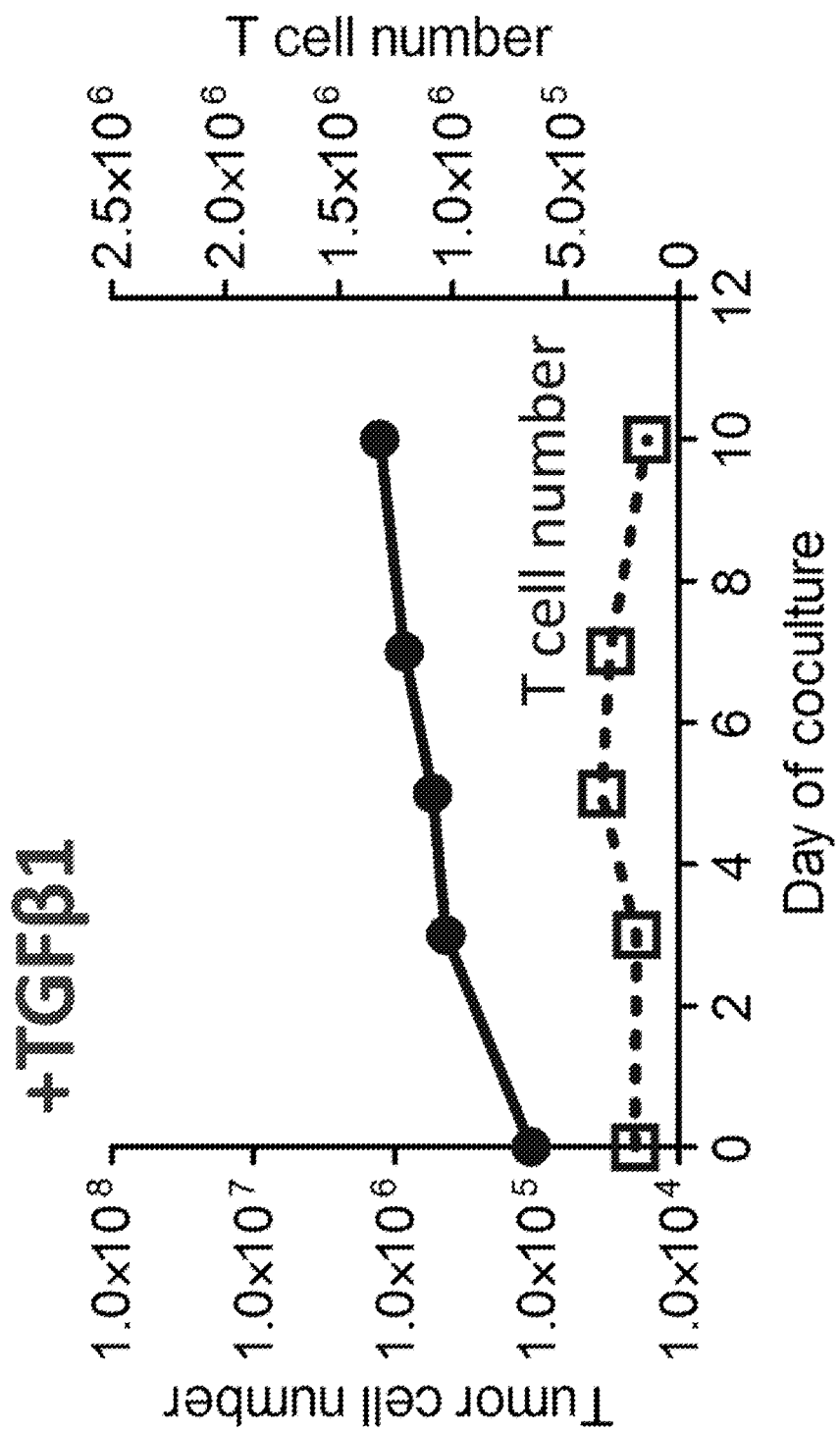
FIG. 22 shows that 2G.CAR-PSCA T cells did not proliferate in the presence of TGFβ1.

FIG. 22 shows that 2G.CAR-PSCA T cells did not proliferate in the presence of TGFβ1.

Figure 23:
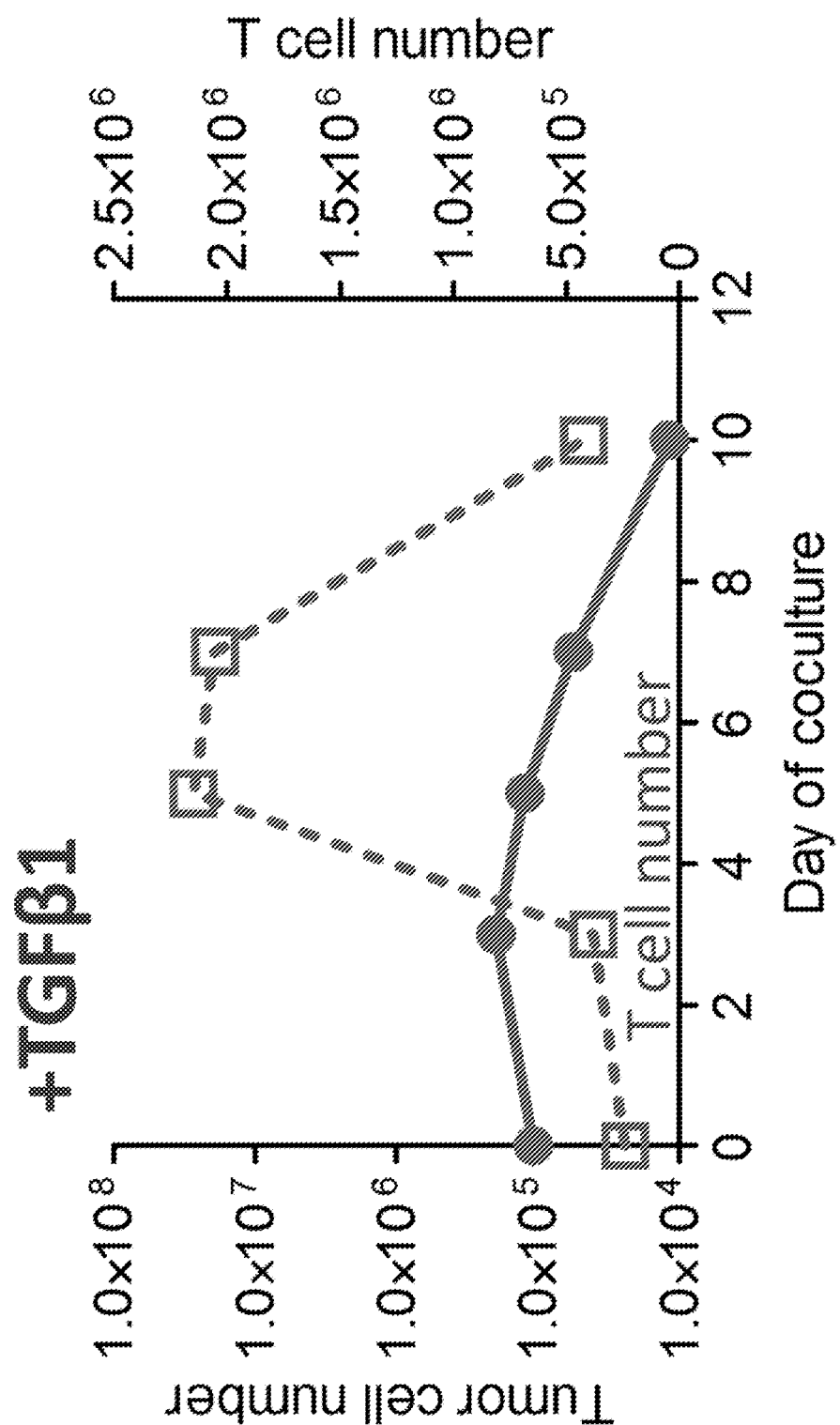
FIG. 23 demonstrates that 2G.CAR-PSCA/RIID4 cells were able to expand and that the cells depend on antigen existence.
Figure 24:
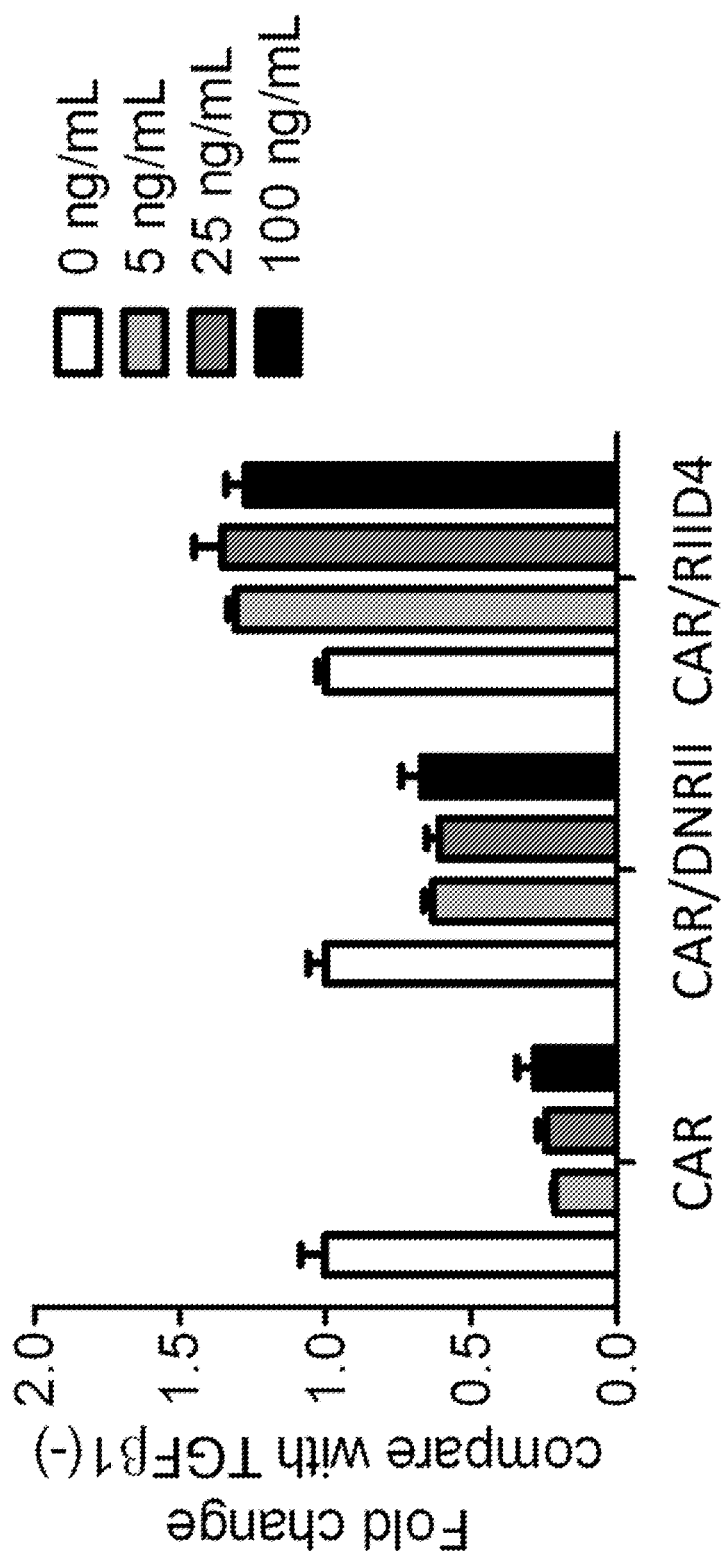
FIG. 24 illustrates that TGFβ1 administration promotes proliferation of 2G.CAR-PSCA/RIID4 T cells.

FIG. 23 demonstrates that 2G.CAR-PSCA/RIID4 cells were able to expand dependent upon antigen existence. FIG. 24 illustrates TGFβ1 administration promotes proliferation of 2G.CAR-PSCA/RIID4 T cells. Therefore, RIID4 modified T cells can use TGFβ1 for their proliferation.

In specific embodiments, the TGFβR/Th1 chimeric cytokine receptor may be used with another chimeric cytokine receptor. In specific embodiments, the TGFβR/Th1 chimeric cytokine receptor is used in the same cell as a IL4Rα/IL7R (4/7R) chimeric cytokine receptor. In specific embodiment, the TGFβR/Th1 chimeric cytokine receptor and the additional chimeric cytokine receptor results in cooperative signaling. Therefore in specific embodiments, there are provided dual-CTLs expressing the (i) 4/7R (ii) the TGFβR/Th1 or (iii) 4/7R and TGFβR/Th1. In certain embodiments, the use of both 4/7R and TGFβR/Th1 chimeric cytokine receptors results in a synergistic response.

Although the present disclosure and its advantages have been described in detail, it should be understood that various changes, substitutions and alterations can be made herein without departing from the spirit and scope of the disclosure as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present disclosure, processes, machines, manufacture, compositions of matter, means, methods, or steps, presently existing or later to be developed that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

---

What is claimed is:

1. A chimeric TGFβ receptor polypeptide, wherein the receptor comprises an exodomain of TGFβ receptor and an endodomain selected from the group consisting of the endodomain of TLR4, wherein said polypeptide is comprised in a T cell.

2. The polypeptide of claim 1, wherein the cell comprises a chimeric antigen receptor (CAR).

3. The polypeptide of claim 2, wherein the CAR is specific for an antigen selected from the group consisting of PSCA, HER2, CD19, CD20, CD22, Kappa or light chain, CD30, CD33, CD123, CD38, ROR1, ErbB3/4, EGFR, EGFRvIII, EphA2, FAP, carcinoembryonic antigen, EGP2, EGP40, mesothelin, TAG72, PSMA, NKG2D ligands, B7-H6, IL-13 receptor α2, IL-11 receptor Rα, MUC1, MUC16, CA9, GD2, GD3, HMW-MAA, CD171, Lewis Y, G250/CAIX, HLA-AI MAGE A1, HLA-A2NY-ESO-1, PSC1, folate receptor-α, CD44v7/8, 8H9, NCAM, VEGF receptors, 5T4, Fetal AchR, NKG2D ligands, CD44v6, TEM1, TEM8 and a combination thereof.

* * * * *